US007507579B2

(12) United States Patent
Boccazzi et al.

(10) Patent No.: US 7,507,579 B2
(45) Date of Patent: Mar. 24, 2009

(54) APPARATUS AND METHODS FOR SIMULTANEOUS OPERATION OF MINIATURIZED REACTORS

(75) Inventors: Paolo Boccazzi, Cambridge, MA (US); Angela Y. Chen, Cambridge, MA (US); Klavs F. Jensen, Lexington, MA (US); Nicolas Szita, Somerville, MA (US); Andrea Zanzotto, Somerville, MA (US); Zhiyu Zhang, Dorchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 615 days.

(21) Appl. No.: 10/816,046

(22) Filed: Apr. 1, 2004

(65) Prior Publication Data
US 2005/0089993 A1 Apr. 28, 2005

Related U.S. Application Data

(63) Continuation-in-part of application No. 10/427,373, filed on May 1, 2003, now abandoned.

(51) Int. Cl.
*C12M 1/12* (2006.01)
*C12M 1/34* (2006.01)
*C12M 3/00* (2006.01)
*C12M 1/00* (2006.01)
*G06K 9/00* (2006.01)

(52) U.S. Cl. ............... 435/297.5; 435/288.7; 435/809; 435/808; 435/303.1; 435/294.1; 435/287.5; 382/129; 382/133

(58) Field of Classification Search ........... 435/288.7, 435/303.1, 809, 808, 294.1, 297.5, 287.5; 382/129, 133
See application file for complete search history.

(56) References Cited

U.S. PATENT DOCUMENTS

| 5,401,465 | A | * | 3/1995 | Smethers et al. ............ 422/52 |
| 6,653,124 | B1 | * | 11/2003 | Freeman ................ 435/297.1 |
| 2002/0055102 | A1 | * | 5/2002 | Stern ........................... 435/6 |

(Continued)

*Primary Examiner*—William H Beisner
*Assistant Examiner*—Nathan A Bowers
(74) *Attorney, Agent, or Firm*—Choate Hall & Stewart LLP

(57) ABSTRACT

The present invention provides a variety of microscale bioreactors (microfermentors) and microscale bioreactor arrays for use in culturing cells. The microfermentors include a vessel for culturing cells and means for providing oxygen to the interior of the vessel at a concentration sufficient to support cell growth, e.g., growth of bacterial cells. Depending on the embodiment, the microfermentor vessel may have various interior volumes less than approximately 1 ml. The microfermentors may include an aeration membrane and optionally a variety of sensing devices. The invention further provides a chamber to contain the microfermentors and microfermentor arrays and to provide environmental control. Certain of the microfermentors include a second chamber that may be used, e.g., to provide oxygen, nutrients, pH control, etc., to the culture vessel and/or to remove metabolites, etc. Various methods of using the microfermentors, e.g., to select optimum cell strains or bioprocess parameters are provided. The invention provides microreactors having a variety of different designs, some of which incorporate active stirring and/or have the capability to operate in batch or fed-batch mode. The invention further provides an apparatus and methods for simultaneous operation of a plurality of microreactors, with monitoring of the individual microreactors during a run. The invention further provides methods of performing gene expression analysis on cells cultured in microreactors.

2 Claims, 45 Drawing Sheets

U.S. PATENT DOCUMENTS

2002/0076804 A1* 6/2002 Sheppard et al. .......... 435/287.1
2002/0197708 A1* 12/2002 Bachur, Jr. ............... 435/287.5
2003/0064507 A1* 4/2003 Gallagher et al. ......... 435/287.2

* cited by examiner

Robotic loading and sampling

Optical fiber, electronic and heating interfaces $1 = CH_3O(CH_2CH_2O)_{2,3}(CH_2)_{11}SiCl_3$ Microfermentor filled with phenol red Microfermentor PMMA
bulk PDMS
PDMS (100μm)
PMMA V ~ 150 μL Φ = 1cm Water evaporation Culture medium

A

B

APPARATUS AND METHODS FOR SIMULTANEOUS OPERATION OF MINIATURIZED REACTORS

CROSS-REFERENCE TO RELATED APPLICATION

This application is a continuation-in-part of U.S. patent application Ser. No. 10/427,373 filed May 1, 2003, now abandoned, which is herein incorporated by reference; and claims priority to U.S. Provisional Patent Application 60/376,711, filed May 1, 2002.

BACKGROUND OF THE INVENTION

A critical driving force behind research in bioprocess science and engineering continues to be the demand for fast and accurate analytical information that can be used, for example, to evaluate the interactions between biological systems and bioprocess operations. One significant challenge is to carry out large numbers of experiments rapidly and efficiently. This issue is of particular importance since many of the advances in molecular biology now lead to large numbers of potential biological systems that contain evolved biocatalysts, new pathway designs, and a variety of unique biological organisms from diverse sources.

Bioprocess development techniques have been unable to keep pace with the current rate of discovery and genetic manipulation in biological systems. Of the hundreds of thousands of genetic and process permutations that can now be designed, only a small fraction can be tested using standard bioprocess practices. Bench-scale bioreactors, with typical volumes of between 2 and 10 liters, are limiting for a number of reasons including the time required to obtain sufficient data for a biological system, the effort required to obtain the data, and the high cost of these systems. Currently the smallest bioreactors that are available commercially have working volumes of approximately 0.5 liters (Sixfors, Appropriate Technical Resources) and allow six parallel fermentations to be carried out.

There exists a need for systems that allow rapid testing, process development, and optimization to be carried out through parallel fermentations. In particular, there exists a need for microscale bioreactor systems that allow multiple experiments to be performed in parallel without an accompanying increase in cost. In addition, there exists a need for microscale bioreactor systems wherein experimental conditions and results obtained in the microscale bioreactor may be translated into predictable large-scale bioprocess operations.

The above needs are not limited to bioprocess development but extend more generally to other settings, e.g., any settings in which it is desired to test or optimize reaction conditions, substrates, etc.

SUMMARY OF THE INVENTION

The present invention encompasses the recognition that the ability to perform cell culture, e.g., for testing, strain optimization, bioprocess parameter optimization, etc., in bioreactors with small volumes offers significant advantages as compared with fermentations performed in traditional production scale or bench scale fermentors. Accordingly, the invention provides a variety of microscale bioreactors (microfermentors), microscale bioreactor arrays, and associated apparatus as well as methods for use thereof. The invention further encompasses the recognition that the use of small scale reactors in process development and optimization extends beyond the field of bioproduction. The testing and/or optimization of any type of chemical or biochemical reaction would benefit from the availability of small-scale reactors that could be operated in parallel. Thus any of the bioreactors, bioreactor arrays, and reactor operation units described herein may be used for chemical process development and/or optimization.

In one aspect, the invention provides a microscale bioreactor (microfermentor) comprising a vessel having an interior volume of less than 200 microliters and means for providing oxygen to the vessel at a concentration sufficient to support cell growth. Optionally, the microfermentor includes at least one channel extending from and in communication with the vessel and/or means for introducing a component into the vessel or removing a sample from the vessel via a channel. According to certain embodiments of the invention the means for providing oxygen comprises an aeration membrane, wherein oxygen diffuses through the membrane into the vessel. The membrane may comprise, for example, a fluoropolymer or a silicone.

In another aspect, the invention provides microscale bioreactors as described above and having means for quantification of biomass, e.g., by measuring the optical density of the culture medium, by measuring the concentration of a cell metabolite, etc. Optionally, the microscale bioreactors may include means for measuring dissolved oxygen within the culture vessel, and/or means for measuring at least one other parameter, which may be, e.g., temperature, pH, carbon dioxide concentration, carbon source concentration, concentration of an ionic species, and concentration of a cellular metabolite.

According to certain embodiments of the invention the means for measuring biomass and/or a bioprocess parameter comprises an optical sensor, e.g., an optical chemical sensor. In certain embodiments of the invention a waveguide sensor is used. According to certain embodiments of the invention Raman spectroscopy is used to measure one or more bioprocess parameters, e.g., concentrations of various organic compounds present in the medium.

In certain aspects of the invention the microscale bioreactors include means for controlling the temperature and/or pH in the culture vessel. The microscale bioreactor systems of the invention may also include means for delivering nutrients and/or for removing a cell product from the culture vessel.

In another aspect, the invention provides two-vessel microscale bioreactors that comprise a first vessel having an interior volume of 1 ml or less for culturing cells and a second vessel separated from the first vessel at least in part by a membrane permeable to oxygen and carbon dioxide. In certain embodiments of the invention the membrane is permeable to cell products and/or nutrients but not permeable to cells. These microscale bioreactor systems may further include means for flowing a liquid or gas through the second vessel.

In another aspect, the invention provides a microreactor comprising: (a) a first body layer that defines a vessel having an interior volume of less than 1 microliter; (b) a second body layer that defines a headspace located opposite the vessel; and (c) a gas-permeable membrane that separates the vessel interior from the second body layer. In certain embodiments of the invention the microreactor incorporates a miniature mixing stirbar. In certain embodiments of the invention the microreactor operates either in batch or fed-batch mode.

In another aspect, the invention provides a chamber sufficiently large to accommodate the microscale bioreactor or microscale bioreactor array, wherein the chamber provides means to control at least one environmental parameter such as temperature or humidity.

In another aspect, the invention provides an apparatus for parallel operation of a plurality of microreactors comprising (a) a chamber equipped with at least one element that supports or secures a microreactor tray inside the chamber, wherein the microreactor tray holds a plurality of microreactors; and (b) a supporting component that holds a signal transmission device, wherein the supporting component and microreactor tray are controllably movable with respect to one another. In certain embodiments of the invention the microreactor tray is removable. In certain embodiments of the invention the apparatus includes support structures that support or contain an actuating device. Any of a number of different microreactor trays can be mounted in the apparatus, and various different microreactor designs can be accommodated by the trays.

The invention further provides bioreactor assemblies (microfermentor arrays) for performing multiple fermentations in parallel. Such assemblies include a plurality of microscale bioreactors as described herein.

In other aspects, the invention includes a variety of methods for using the microscale bioreactors and microscale bioreactor arrays. For example, the invention provides a method of selecting a strain that produces a desired product or degrades an unwanted compound comprising steps of (a) culturing a plurality of different strains, each in an individual microscale bioreactor; (b) measuring the amount of the desired or unwanted product in each of the microscale bioreactors; and (c) selecting a strain that produces an optimum amount of a desired product or degrades a maximum amount of the unwanted compound. The invention further provides a method of selecting a bioprocess parameter comprising steps of (a) culturing an organism type in a plurality of microscale bioreactors, wherein the microscale bioreactors are operated under conditions in which the value of the bioprocess parameter varies and wherein the organism produces a product or degrades a compound; (c) monitoring biomass in each of the microscale bioreactors; and (d) identifying the value of the bioprocess parameter that results in optimum biomass, optimum product formation, or optimum compound degradation. In addition to biomass, other bioprocess parameters may also be monitored, and multiple parameters may be varied. According to certain embodiments of the invention the bioprocess parameter or parameters are actively controlled. The above methods can conveniently be practiced with the apparatus for parallel operation of a plurality of microreactors provided herein.

In another aspect, the invention provides a method of monitoring gene expression comprising: (a) culturing cells in a microbioreactor, wherein the microbioreactor comprises a vessel with an interior volume of 200 µl or less and means for providing oxygen to the interior of the vessel; (b) harvesting some or all of the cells; (c) contacting RNA obtained from the cells, or a nucleic acid transcription product of such nucleic acid, with a microarray comprising probes for a plurality of genes under conditions such that hybridization occurs; and (d) collecting a signal from the microarray, wherein the signal is indicative of the expression level of at least one gene.

The contents of all papers, books, patents, etc., mentioned in this application are incorporated herein by reference.

BRIEF DESCRIPTION OF THE DRAWINGS

FIG. 3 (lower portion) shows a schematic of a microfermentor array of the microfermentors depicted in the upper portion of the figure.

FIG. 25A shows an expanded view of the layer structure of the microreactor. FIG. 25B shows a longitudinal section of the microreactor with channels and integrated magnetic stirbar. FIG. 25C illustrates the principle of passive delivery of a liquid to the microreactor vessel.

FIG. 26A shows a photograph of the empty vessel of the microreactor. The stirbar and fluorescent sensor for DO (black spot) are visible. FIG. 26B shows the microreactor vessel at the end of a fermentation run. Turbidity of the cell culture obscures the stirbar and the DO sensor.

FIG. 32A shows a solid perspective view of the chamber itself and the supporting component. A tubular sheath suitable for holding an optical fiber cable is mounted in the supporting component. The microreactor tray is not shown. FIG. 32B depicts one embodiment of a supporting component of the invention in more detail. FIG. 32C shows a schematic diagram of an upper view of a tubular sheath with a small ring. FIG. 32D shows a solid perspective view of a plate that contains means for mounting a microreactor tray thereon and also contains a plurality of support structures. FIG. 32E shows a cross-sectional top view of a supporting component. As elsewhere herein, dimensions are for representative purposes and are not intended to be limiting.

FIG. 35A shows the apparatus with the supporting component for a signal transmission device in starting position, prior to the beginning of a measurement cycle. FIG. 35B shows the supporting component after pushing a support structure for an actuating device out of the way so that the signal transmission device can gain access to a microreactor mounted in the reactor tray. In order to more clearly illustrate the pushing action of the supporting component, the microreactor tray and microreactors are not shown.

FIGS. 38A and 38B show cross-sectional views from two angles. FIG. 38C shows an external view.

FIG. 42A shows a schematic perspective diagram of a microbioreactor with integrated sensors mounted on a glass substrate. FIG. 42B shows a photograph of the microbioreactor.

FIGS. 43A and 43B show optical density in microbioreactors and bench-scale bioreactors respectively. FIGS. 43A and 43B show % dissolved oxygen in microbioreactors and bench-scale bioreactors respectively. FIGS. 43A and 43B show pH in microbioreactors and bench-scale bioreactors respectively. Each curve represents an individual bioreactor run.

44C), and lactate (FIG. 44D) in a microbioreactor and a bench-scale bioreactor monitored over time.

Figure 45:
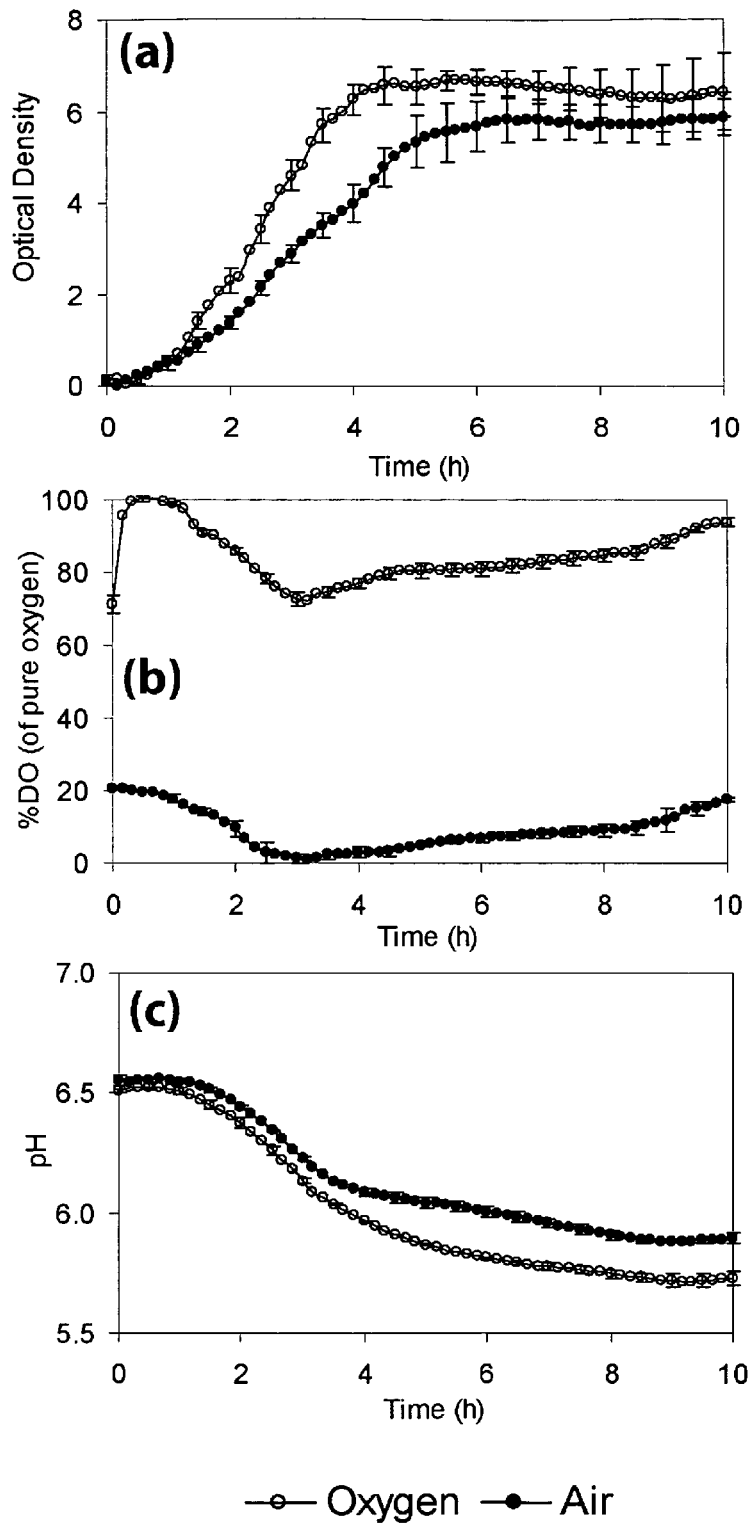

FIGS. 45A-45C are graphs showing values for optical density (FIG. 45A), % dissolved oxygen (FIG. 45B), and pH (FIG. 45C) for cells cultured in microbioreactors with pure oxygen (open circles) or air (closed circles).

Figure 46A:
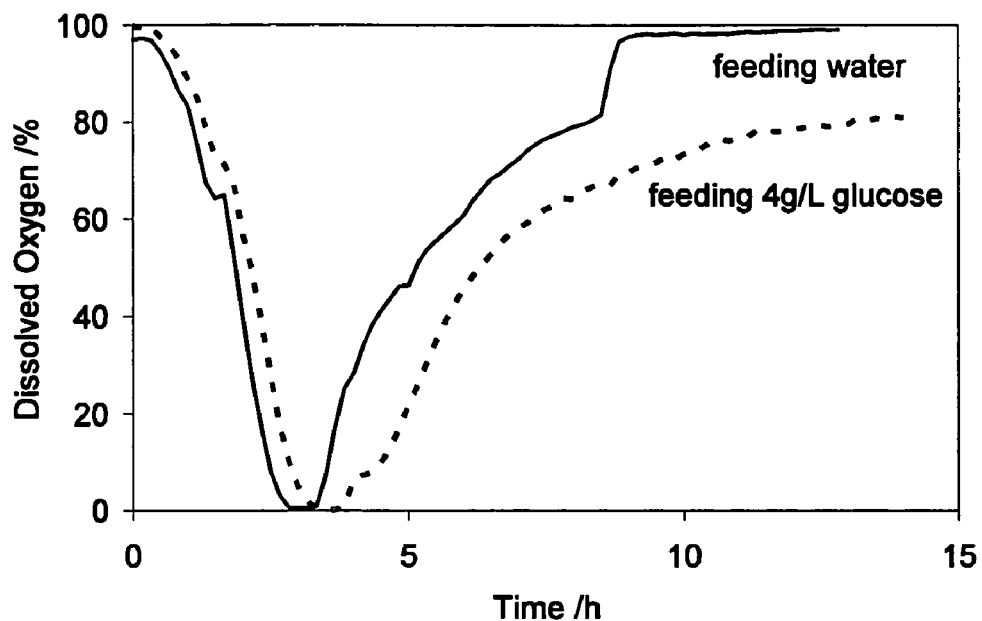
Figure 46B:
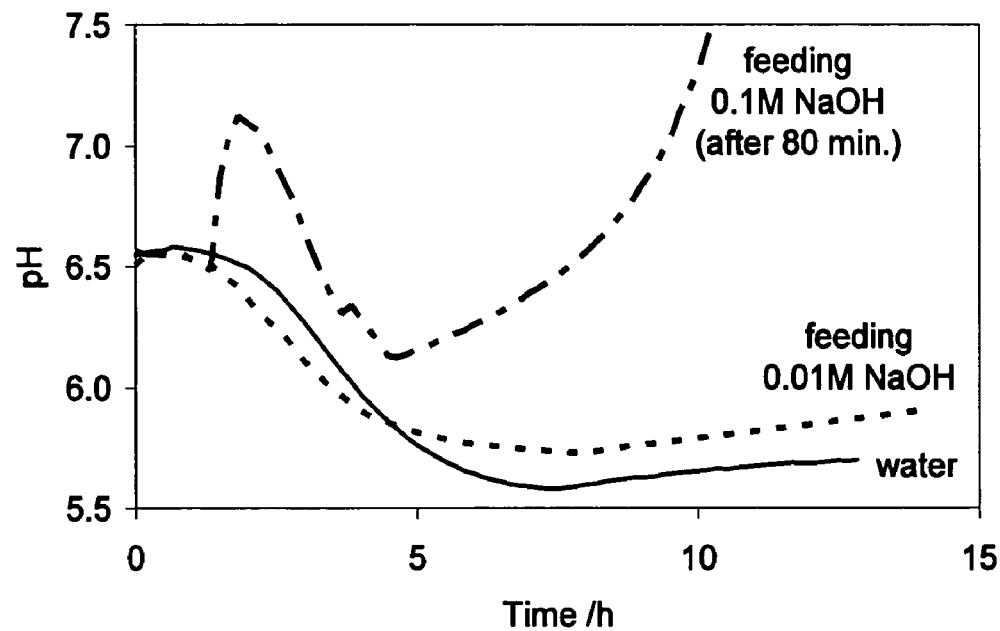

FIGS. 46A-46B show results comparing operation of batch and fed-batch fermentation runs in a microreactor capable of operating in fed-batch mode. FIG. 46A is a graph showing dissolved oxygen concentration over time in a fed-batch fermentation in which the culture (E. coli) was supplied with 4 g/L glucose (dashed line) and in a batch fermentation in which the culture was supplied only with water (solid line). FIG. 46B is a graph showing pH over time in two fed-batch fermentations in which the cultures (E. coli) were supplied with 0.1 M NaOH (dot-dash line) or 0.01 M NaOH (dashed line) and in a batch fermentation in which the culture was supplied only with water (solid line).

Figure 47A:
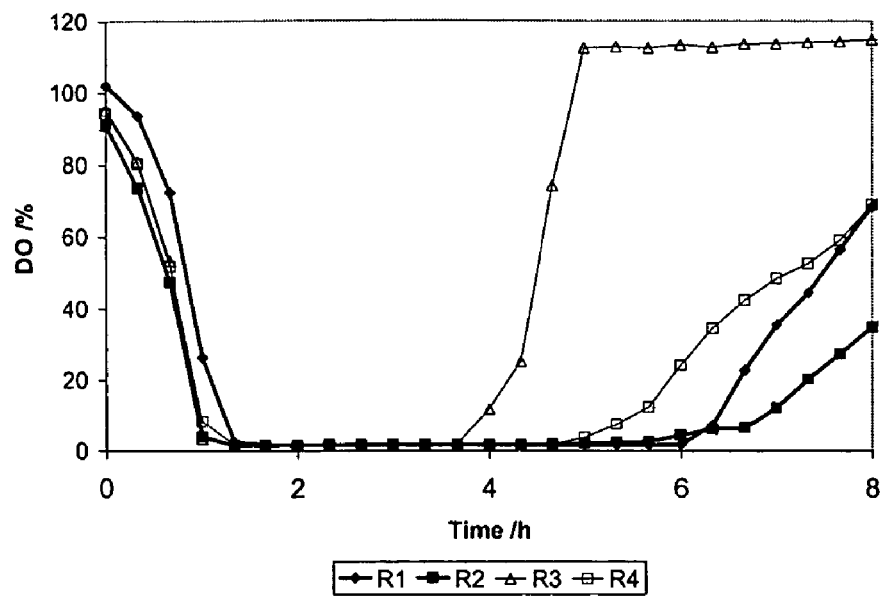
Figure 47B:
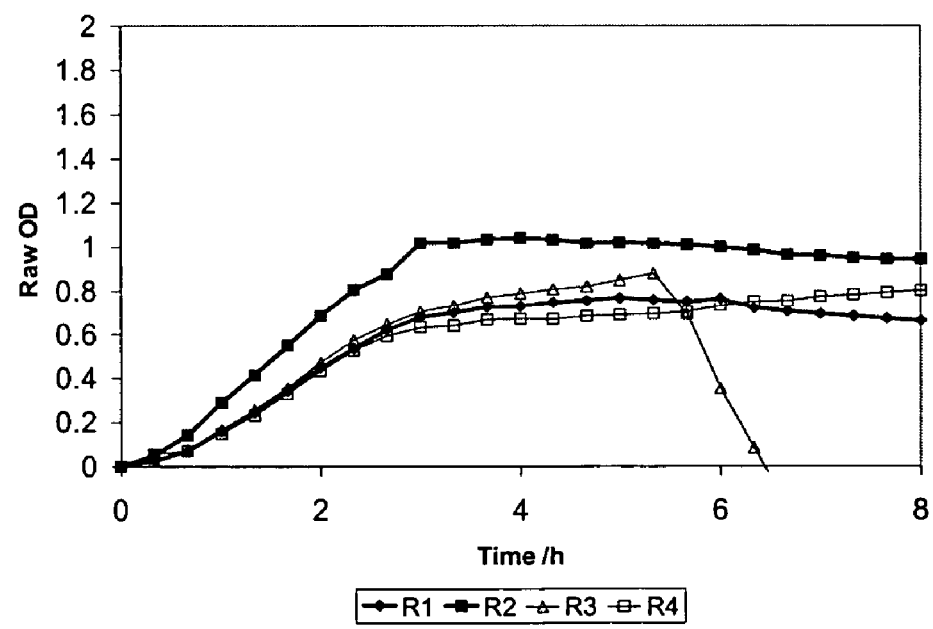
Figure 47C:
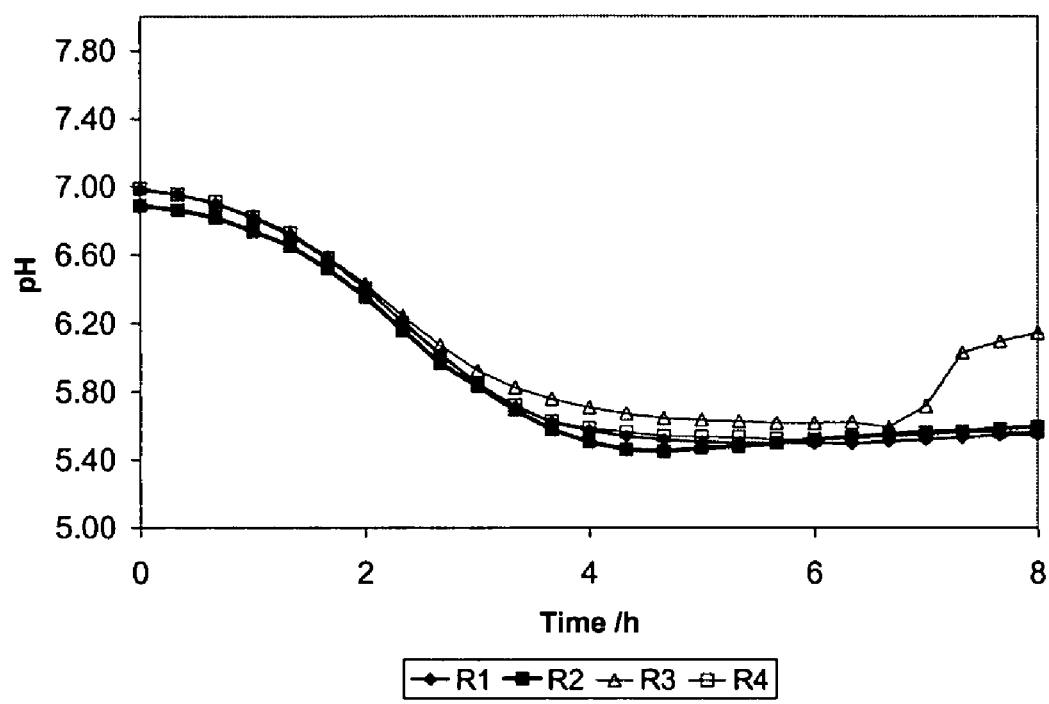

FIGS. 47A-47C show graphs of dissolved oxygen (DO), raw optical density (OD), and pH for four microreactors operating in parallel in an apparatus of the invention.

Figure 48A:
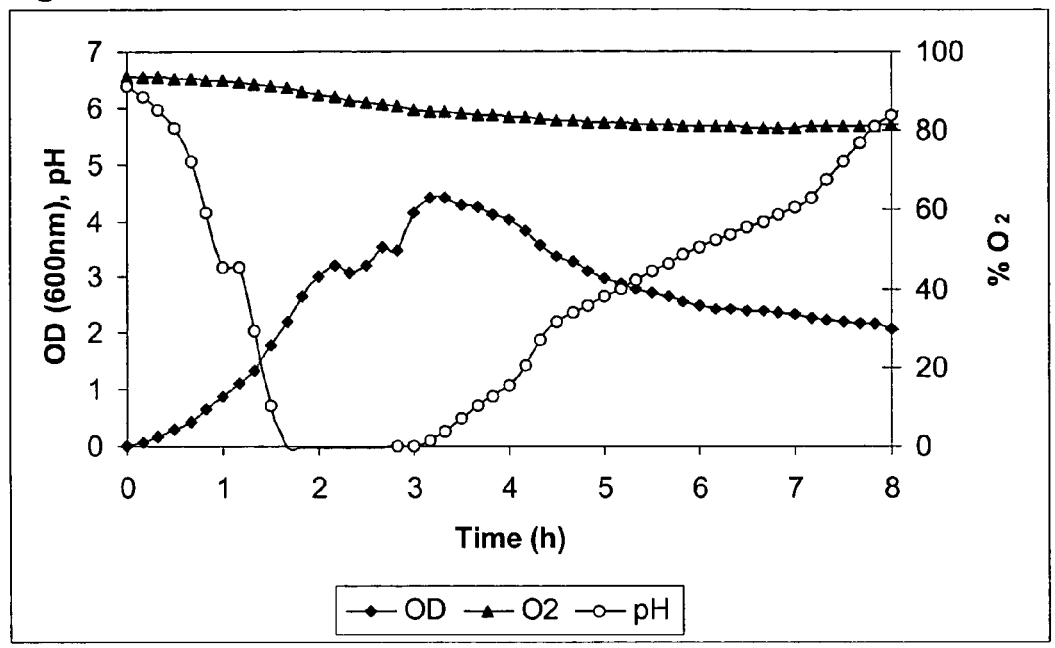
Figure 48B:
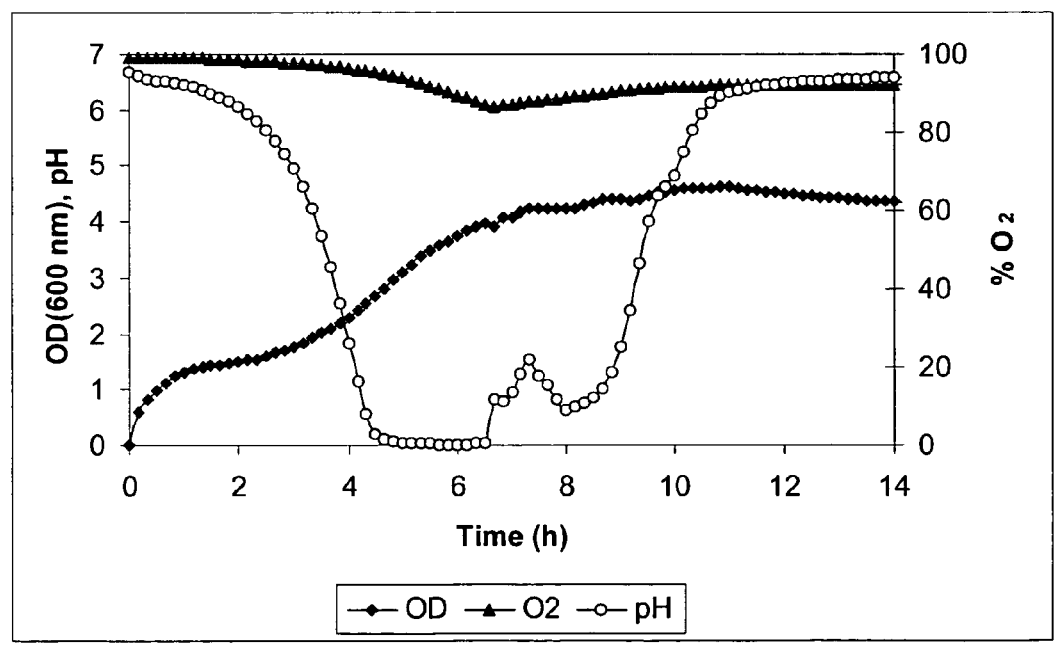

FIGS. 48A and 48B show graphs of optical density (OD), dissolved oxygen (DO) and pH of E. coli FB21591 grown in 50ut microbioreactors in LB plus 0.8% glucose (A) and defined medium containing 0.8% glucose (B).

DETAILED DESCRIPTION OF CERTAIN EMBODIMENTS

I. Overview

The present invention encompasses the recognition that microscale bioreactors (microfermentors) offer a means of addressing the continuing demand in bioprocess science and engineering for fast and accurate analytical information that can be used to rapidly evaluate the interactions between biological systems and bioprocess operations. In addition, such systems provide a platform for efficiently incorporating modern tools of biology (e.g., genetics, enzymology, molecular biology, and bioinformatics) to improve bioprocess screening and development. For example, microscale bioreactors allow the rapid screening of strains and metabolic pathways for applications ranging from synthesis of natural products to bioremediation. Bioprocess technology has been instrumental in the development and large-scale production of numerous pharmaceuticals and vaccines. In addition, bioprocesses are employed in the food industry, waste treatment, etc.

Metabolic pathway engineering is making a profound impact in areas as diverse as drug discovery (e.g., through the synthesis of novel natural products (2)), commodity chemicals (e.g., the synthesis of ascorbic and lactic acids (3) 1,3-propanediol (4)), and the biodegradation of toxic pollutants (5). Metabolic engineering encompasses the targeted improvement of product formation or cell properties through the modification of biochemical reactions. Hence, metabolic engineering focuses on determining the enzymes that offer the greatest amount of control over the rate of production of a certain metabolite (metabolic control analysis or MCA), then altering the activity of those enzymes (e.g., via molecular biology) and/or altering relevant reaction conditions to manipulate product yields. MCA can involve making mathematical models, carbon tracing, and developing assays for obscure metabolites and aids in the understanding of metabolic fluxes. The alteration of enzyme activities can involve polymerase chain reaction (PCR) techniques, genetic library construction, screening, cloning, and other molecular biology tools. Microfermentor technology will have a significant impact both on how bioprocess development and metabolic engineering research are carried out and also on how rapidly research can be translated into improvements into bioprocesses.

The invention provides microscale bioreactors that include a vessel for culturing cells having a interior volume of less than 200 μl and means for providing oxygen to the interior of the vessel so as to support the growth of cells. The terms "interior volume" and "working volume" are used interchangeably herein. In addition, the invention provides a microscale bioreactor system including a microscale bioreactor and a chamber that provides environmental control. The invention also provides a bioreactor assembly including an array of microscale bioreactors, which may be operated in parallel. The availability of a large number of bioreactors operating in parallel offers a number of unique advantages. For example, the microfermentor array makes it possible to (i) systematically evaluate the effects of varying one or more of a large number of parameters (e.g., temperature, nutrient composition, pH, etc.) on any phenotypic characteristic of interest, e.g., growth rate, metabolite production or compound biotransformation ability, etc., of a particular strain or (ii) systematically evaluate the characteristics (e.g., metabolite production) of a large number of different strains while holding environmental conditions constant.

Developing microscale bioreactors requires more than merely scaling down from currently available fermentor technology. For example, the large volumes employed in traditional fermentors makes it possible to monitor parameters such as oxygen concentration, biomass, etc., by removing samples from the fermentor at appropriate times. Sequential sampling may be impractical in the context of a microscale bioreactor or may need to be performed differently and on a smaller scale. Large indwelling sensor devices are not practical in the context of a microfermentor. Thus accurate monitoring of bioprocess parameters, a requirement for many applications, requires the development of alternative methods. Furthermore, oxygenation using traditional techniques such as sparging and/or stirring may be problematic in small volumes.

In addition to the challenges discussed above, use of fermentors with small volumes offers a number of potential advantages. For example, microfabrication technologies can be used to efficiently produce a large number of identical microfermentors. Microfabrication also allows integration of sensing devices into the structural components of the bioreactor, which enhances the possibilities for acquiring large amounts of data in an efficient manner. Thus in preferred embodiments of the invention at least one sensing device is integrated into a structural component of the microfermentor.

Miniaturization of fermentation processes to microliter scale represents a significant departure from conventional procedures. The inventors have recognized the need to address the following significant issues: (i) design and fabrication techniques, including materials selection and surface modification; (ii) bioprocess parameter control; (iii) selection, development, and integration of sensor technology; and (iv) appropriately sensitive analytical devices. In addition, the inventors have recognized the importance of utilizing appropriate biological systems for evaluating performance of the microfermentors and for comparing microfermentors with traditional bioprocessing methodologies. Significant differences between traditional fermentors and microfermentors include, for example (i) the ratio of wall surface area to volume; (ii) more significant evaporative losses in microfermentors; (iii) incompatibility of microfermentors with conventional oxygenation methods.

As described in more detail in the Examples, the inventors have constructed a microscale bioreactor with a working volume of 5 µl and have shown that it can support the growth of bacterial cells. The inventors have demonstrated successful delivery of oxygen to the microfermentor interior and lack of toxicity over a period of 10 hours.

Non-invasive online monitoring of dissolved oxygen, optical density, and pH during the culture period was achieved using integrated optical sensors. Results indicate that cell growth and various additional bioprocess parameters including dissolved oxygen profile and pH profile within the vessel over time, final number of cells, and cell morphology in the microfermentor are comparable to that in a conventional fermentor. Values of additional parameters including organic acid production and substrate utilization also closely resemble those obtained in larger fermentation vessels.

The inventors have constructed a number of additional microreactors having working volumes of less than 200 µl, including embodiments with magnetic mixers, and successfully employed them to monitor growth of microorganisms cultured in the microreactor vessels. In addition, the inventors have demonstrated a fed-batch system in which a solution of interest is added continuously to a microreactor during the culture period. Effects on cell growth were observed, demonstrating active control over bioprocess parameters. The inventors have also developed methods for measuring gene expression using the small growth volumes available from the microreactors of the invention.

In addition, the inventors have constructed an apparatus that supports simultaneous operation of multiple microreactors and allows non-invasive online monitoring of bioprocess parameters. The apparatus can support a wide variety of microreactor configurations and detection methods and optionally includes various actuators that drive motion or activity of additional devices located within the microreactor vessels.

The following sections provide relevant definitions, describe the manner in which the invention addresses the foregoing concerns and others, and describe methods for making and using the microreactors, microreactor arrays, apparatus for simultaneous operation of multiple microreactors, and other aspects of the invention.

II. Definitions

Actuating device (also referred to as an actuator): An "actuating device" or "actuator" refers to a device that puts another device or element of a system into action or motion.

Bioreactor Operation Strategies: In accordance with the terminology as commonly accepted in the art and described in (54), bioreactor operation strategies can be classified into one of three general modes, i.e., batch or fed-batch operations, the semi-continuous or cut-and-feed strategy (which may also be referred to as semi-batch), and perfusion culture. Batch culture is usually performed using suspension culture cells in a stirred tank bioreactor, although in the case of a microreactor as described herein, stirring may or may not be performed. Product is harvested from the medium at the end of the batch cycle. Fed-batch culture differs from batch culture in that nutrients (or solutions of interest such as reactants, buffers, etc.) are added either continuously or periodically during the batch cycle. The semi-continuous or cut-and-feed strategy also typically employs stirred tank, homogeneously mixed bioreactors. In this operating strategy a bioreactor is inoculated with cells, which are then allowed to grow for a period of time, often until the culture is approaching early stationary phase. A large fraction of the cell culture broth is then harvested, usually on the order of 70-90%, and the bioreactor replenished with fresh medium. The cycle is then repeated. Perfusion operations retain cells within the reactor while allowing a cell-free sidestream to be removed; they can be subdivided into two categories, the homogeneous systems such as the perfusion chemostat or heterogeneous systems like hollow fiber or fluidized bed bioreactors. It is to be understood that these definitions are not intended to limit the invention or its modes of operation in any way and that they are to be interpreted as appropriate in the context of microfermentors as described herein.

Channel: The term "channel" refers to a hole of constant or systematically varied cross-sectional area through a material. Generally a channel has a defined cross-sectional geometry, which may be rectangular, ovoid, circular, or one of these geometries with an imposed finer feature, such as indentations, etc. A "microfluidic channel" has at least one dimension of less than 1000 microns.

Fermentation: The terms "ferment", "fermentation", etc., are to be understood broadly as indicating culture of cells in general. The terms do not imply any particular environmental conditions or metabolic processes. While typically these terms refer to culture of bacterial cells (e.g., eubacteria), they may also apply to archaebacteria or eukaryotic cells (e.g., yeast or mammalian cells). As a noun, a "fermentation" or "fermentation run" or "fermentor run" refers to a period of time during which cells are cultured in a fermentor.

Microreactor: As used herein, the term "microreactor" refers to a reactor, i.e., a device that contains a space in which a chemical or biochemical process (e.g., the growth of cells) is conducted, having an interior volume of less than 1 ml. Microreactors include microscale bioreactors, also referred to as microbioreactors.

Microscale bioreactor: As used herein the term "microscale bioreactor" is used to describe a bioreactor (i.e., an apparatus for culturing cells) having an interior volume of less than 1 ml. The terms "microscale bioreactor" and "microfermentor" are used interchangeably herein.

Parallel: Reaction runs, including but not limited to, fermentor runs are performed "in parallel" when the run times of the runs overlap. The runs may, but need not be, started and/or terminated at substantially the same time. The runs may last for the same length of time or for different lengths of time.

Strain: In a broad sense, cells or viruses may be considered to be of different strains if they differ from each other in one or more phenotypic or genotypic characteristic. In general, a "strain" is a population of organisms descended from a single cell and maintaining the phenotypic and genotypic characteristics of that cell. Although frequently used to refer to microbes (i.e., microscopic organisms), the term may be used herein to refer to cells of any type.

III. Design and Fabrication of Microscale Bioreactor

A. Design

In certain embodiments of the invention the microscale bioreactor comprises a vessel for culturing cells and a means for providing oxygen to the vessel at a concentration sufficient to support cell growth. In certain embodiments of the invention the vessel has an interior volume of less than 1 ml. In certain embodiments of the invention the vessel has an interior volume of less than 200 µl. In certain preferred embodiments of the invention the working volume is between 50 µl and 100 µl inclusive. In certain preferred embodiments of the invention the working volume is between 5 µl and 50 µl, inclusive. In certain preferred embodiments of the invention the working volume is between 5 µl and 10 µl, inclusive. In certain preferred embodiments of the invention the working volume is approximately 7.5 µl or approximately 10 µl. In certain preferred embodiments of the invention the working volume is approximately 5 µl. (Generally the term "approximately" as used herein will indicate that a number may vary by ±1%, ±5%, ±10%, depending upon the context.) Small working volumes offer a number of advantages. For example, they permit efficient gas-liquid contacting to control the level of dissolved oxygen (DO). Small working volumes also imply smaller diffusion times, which aids in exchange of gases. In addition, microscale bioreactors having working volumes in the range of between 5 µl and 50 µl or between 50 µl and 100 µl may be more easily produced using microfabrication than those with larger working volumes. Microfabrication facilitates the production of microfermentor arrays with a very high density of individual microfermentors. In addition, microfabrication allows for configurations with very large specific gas-liquid interfaces. Particularly in the context of microscale bioreactors employing active aeration, microfabrication allows one to achieve a large mass trans coefficient ($k_L a$). For example, the inventors have achieved a greater than two orders of magnitude increase in mass transfer coefficients for gas-liquid-solid reaction systems by precise design of the contacting scheme (8). Moreover, small system dimensions imply faster diffusion across the vessel volume and thus more uniform conditions within. Furthermore, smaller dimensions (e.g., dimensions resulting in an interior volume of less than approximately 100 µl) may be desirable to ensure adequate support for an aeration membrane that forms the top of the culture vessel.

Figure 1A:
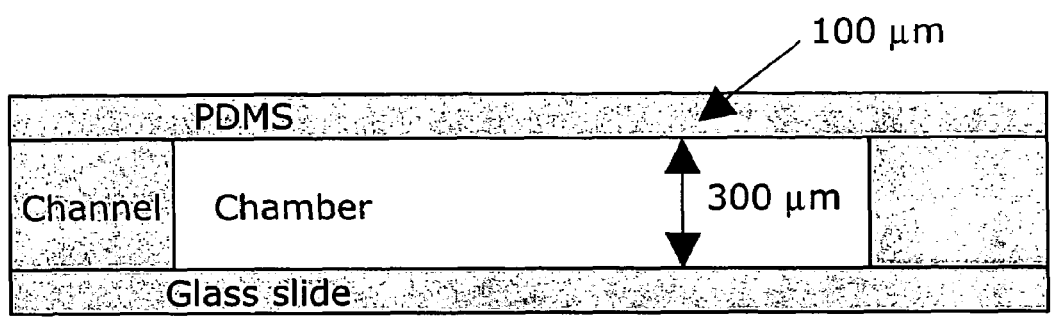
FIGS. 1A and 1B show top and side views of the design of one embodiment of a microfermentor of the invention.
Figure 1B:
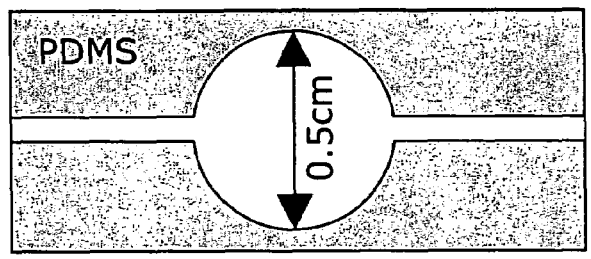

FIGS. 1A and 1B show top and side views of the design of one embodiment of a microfermentor of the invention. As seen in FIG. 1A, in this embodiment of the invention the vessel has a round cross-section in the horizontal dimension with an overall cylindrical configuration. The bottom of the microfermentor is formed from a rigid substrate (e.g., silicon, glass, plastics such as polycarbonate, plexiglass, etc.), sufficiently strong to support and stabilize the remaining portions of the structure. In certain embodiments of the invention at least one wall (e.g., a side wall, top wall, or bottom wall) of the microfermentor comprises a transparent material to permit optical access. However, in certain embodiments of the invention use of a transparent material is not necessary as waveguides can be used to guide light in or out (see below).

As shown in FIG. 1, in preferred embodiments of the invention one or more channels extend from the vessel. For example, in those embodiments of the invention that operate in batch mode, the channels are used solely to introduce medium and inoculum (i.e., cells) to the vessel prior to the beginning of a fermentation. However, in certain embodiments of the invention such channels may be used for other purposes, e.g., to remove samples, to introduce additional components such as nutrients, buffers, etc., during the course of a fermentation. The channels may conveniently be used to interface with robotics, e.g., for introducing components into the vessel and/or for removing samples. Robotics may be used, for example, to interface microfermentors or microfermentor arrays with, for example, a microtiter plate from which materials may be transferred into the fermentor or into which samples may be placed. The channels may connect with pumps, reservoirs, etc. Microfluidics technology may be employed.

As described further below, the microfermentor includes means for delivering oxygen to the vessel. In preferred embodiments of the invention one or more walls of the microfermentor vessel consists at least in part of a gas-permeable membrane for oxygenation of the growing culture. The gas-permeable membrane may also aid in dispersal of gases produced during metabolism. In certain embodiments of the invention as described in Example 1, the membrane serves as both the aeration membrane and the structural material of the microfermentor. For example, as shown in FIG. 1, both the top and side walls of one embodiment of the microfermentor are made of the polymeric material poly(dimethylsiloxane) (PDMS). In certain embodiments of the invention the microfermentor includes multiple membranes. These membranes may be made from the same material or from different materials, e.g., materials having different properties such as gas diffusivity and solubility.

Since adequate oxygenation is a major consideration for cell growth, selection of appropriate microfermentor dimensions and membrane materials may be guided by an oxygen transport model that takes into account the properties of the oxygen delivery system. Use of such a model is described in more detail in Example 2. The calculations therein may readily be applied to any given material for which parameters such as oxygen diffusivity and solubility are known. In certain embodiments of the invention the permeability (i.e., product of diffusivity and solubility) of the membrane to oxygen is approximately equal to that of PDMS, i.e., 800 Barrer (1 Barrer=$10^{-10}$ cm$^3$(STP)·cm/cm$^2$·s·cm Hg) (44). In certain other embodiments of the invention the permeability of the membrane to oxygen is greater than 800 Barrer. In certain other embodiments of the invention the permeability of the membrane to oxygen is either between approximately 600 and 800 Barrer, between approximately 400 and 600 Barrer, between approximately 200 and 400 Barrer, or between approximately 80 and 200 Barrer.

The invention provides a variety of microscale bioreactor systems in which two vessels are separated by a membrane. A first vessel serves as a cell culture vessel while the second vessel contains a liquid that serves as a source of one or more components such as oxygen, nutrients, buffers, etc. A variety of different configurations are possible.

Figure 2A:
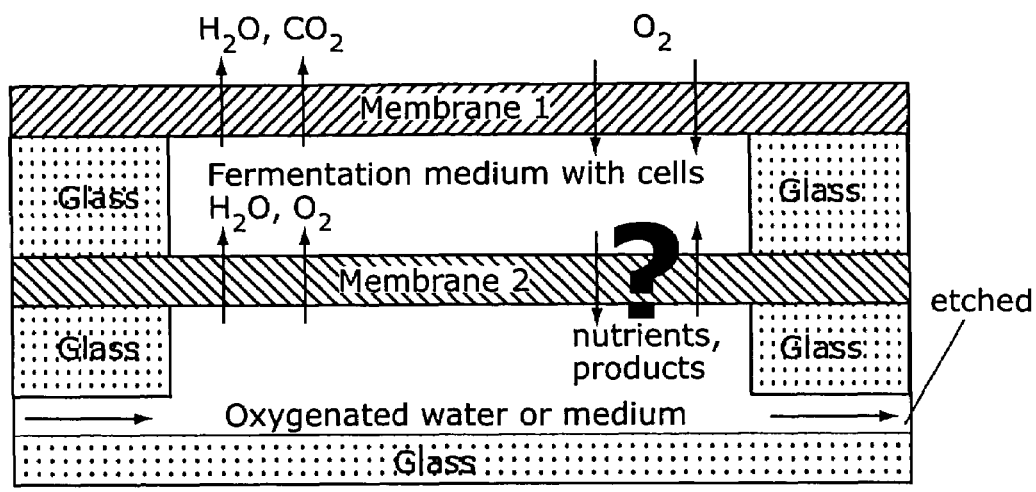
FIG. 2A shows a side view of an embodiment of a two vessel microfermentor in which the fermentation vessel is in contact with the external environment.

FIG. 2A shows a side view of one such embodiment of the invention in which the fermentation vessel is on top. The two vessels of the microscale bioreactor are separated by a membrane (Membrane 2) that allows free transport of water and oxygen into the top vessel. In certain embodiments of the invention this membrane prevents back-diffusion of nutrients, products, and/or salts while in other embodiments of the invention the membrane is permeable to these components. (The question mark in the figure indicates that nutrients, products, and salts may or may not diffuse through Membrane 2.) Membranes such as those typically used in desalination applications can be used for this purpose. A wide variety of membranes that may be used to control the transport of nutrients, products, salts, and cells is available from, e.g., Millipore Corp., Bedford, Mass. Factors such as pore size, surface characteristics such as hydrophobicity, and presence of channels for active or passive transport may be selected by one of ordinary skill in the art to achieve desired transport characteristics.

In the design depicted in FIG. 2A the top membrane (Membrane 1) allows diffusion of water and gases. Salts are not volatile so will not evaporate from the top membrane (Membrane 1), while most products are too large to diffuse readily through the top membrane. Channels in communication with the lower vessel allow oxygenated water to flow through the lower vessel, providing a continuous supply of oxygen and water to diffuse across Membrane 2. Circulation may be achieved using a pump. Since the liquid circulates and can be replenished, the volume of the lower vessel may be small relative to the volume of the upper vessel and may, in certain embodiments of the invention, consist merely of a chamber with similar height to that of the channels.

In certain embodiments of the invention rather than circulating liquid through a lower vessel as shown in FIG. 2A, a lower vessel with a volume that is large relative to the volume of the upper vessel (e.g., at least twice the volume of the upper vessel) is used, thus providing a reservoir of component(s). The contents of the reservoir may be replaced periodically. There may also be channels (not shown) in communication with the cell culture vessel, e.g., in order to allow introduction of cells and culture medium, removal of samples, etc.

This design offers the following features and advantages, among others: (1) Water losses from evaporation may be replaced by osmosis from bottom vessel; (2) Oxygenation may be provided from both the top and bottom (increases maximum allowable depth); (3) Contact with large reservoir of pH-neutral water or medium allows neutral pH to be maintained in the fermentor; (4) The process remains batch if only gases and water permeate membrane, while if the membrane allows nutrients, products, etc., to also permeate, process becomes semi-batch or continuous; (5) Since sensors may be integrated onto the glass or other material from which the microfermentor is fabricated, they are now separated from the fermentation medium. This allows separate calibration for sensors, and also eliminates need to sterilize sensors (e.g. some sensors are UV or temperature sensitive); (6) The design allows control of the oxygen gradient within the culture vessel by controlling oxygen content of water below, and atmosphere above, the culture vessel.

Figure 2B:
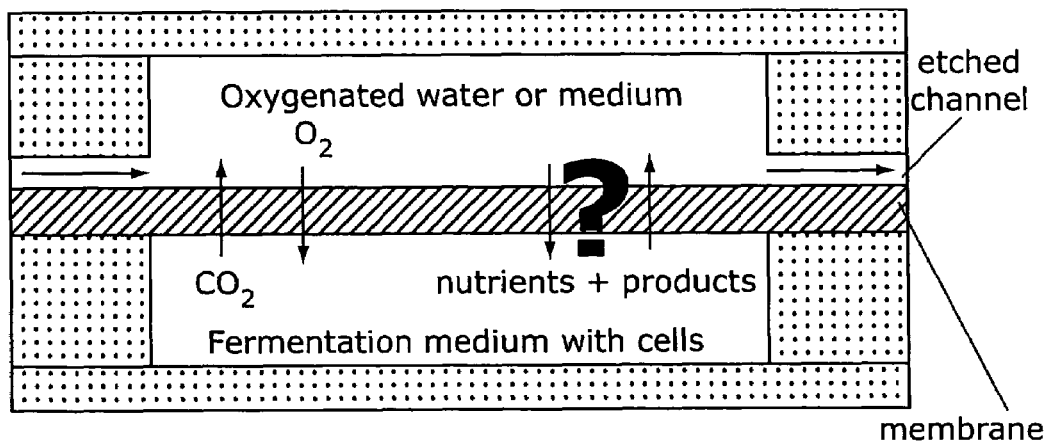
FIG. 2B shows a side view of an embodiment of a two vessel microfermentor in which the fermentation vessel is enclosed.

FIG. 2B shows another embodiment of a two-vessel microfermentor design. In this embodiment the culture vessel is not in contact with air. Instead, oxygen is provided via a membrane that separates the culture vessel from a second vessel that contains a reservoir of oxygenated liquid, e.g., water. The separating membrane allows free transport of water and oxygen into the culture vessel. In certain embodiments of the invention this membrane prevents back-diffusion of nutrients, products, and/or salts while in other embodiments of the invention the membrane is permeable to these components. (The question mark in the figure indicates that nutrients, products, and salts may or may not diffuse through the membrane.) Oxygenated liquid may be flowed through the upper vessel via channels as shown. In this design diffusion from the upper to the lower vessel takes place in the same direction as the gravitational forces.

This design offers the following features and advantages, among others: (1) Water losses from evaporation may be eliminated by contact with the water-filled vessel; (2) Contact with a large reservoir of pH-neutral water or medium allows neutral pH to be maintained in the fermentor; (3) The process remains batch if only gases and water permeate membrane, if the membrane allows nutrients, products, etc. to also permeate, process becomes semi-batch or continuous.

Although in FIGS. 2A and 2B the permeable membranes separating the two vessels have been depicted as structural components of the vessels, this need not be the case. The permeable membranes may instead form a portion of a separating layer made from a less permeable material.

In summary, the two-vessel designs address the potential problem of evaporative losses that may occur, e.g., in a non-humidified environment. In addition, these designs provide a second source of oxygen for the fermentation, and as a result a deeper culture vessel with a larger volume to surface ratio can be utilized. These designs also allow for control of pH, e.g., by allowing diffusion of protons and hydroxyl ions. In addition, pH control may be enhanced by providing appropriate buffers in the liquid that fills the second (non-culture) vessel.

Figure 3:
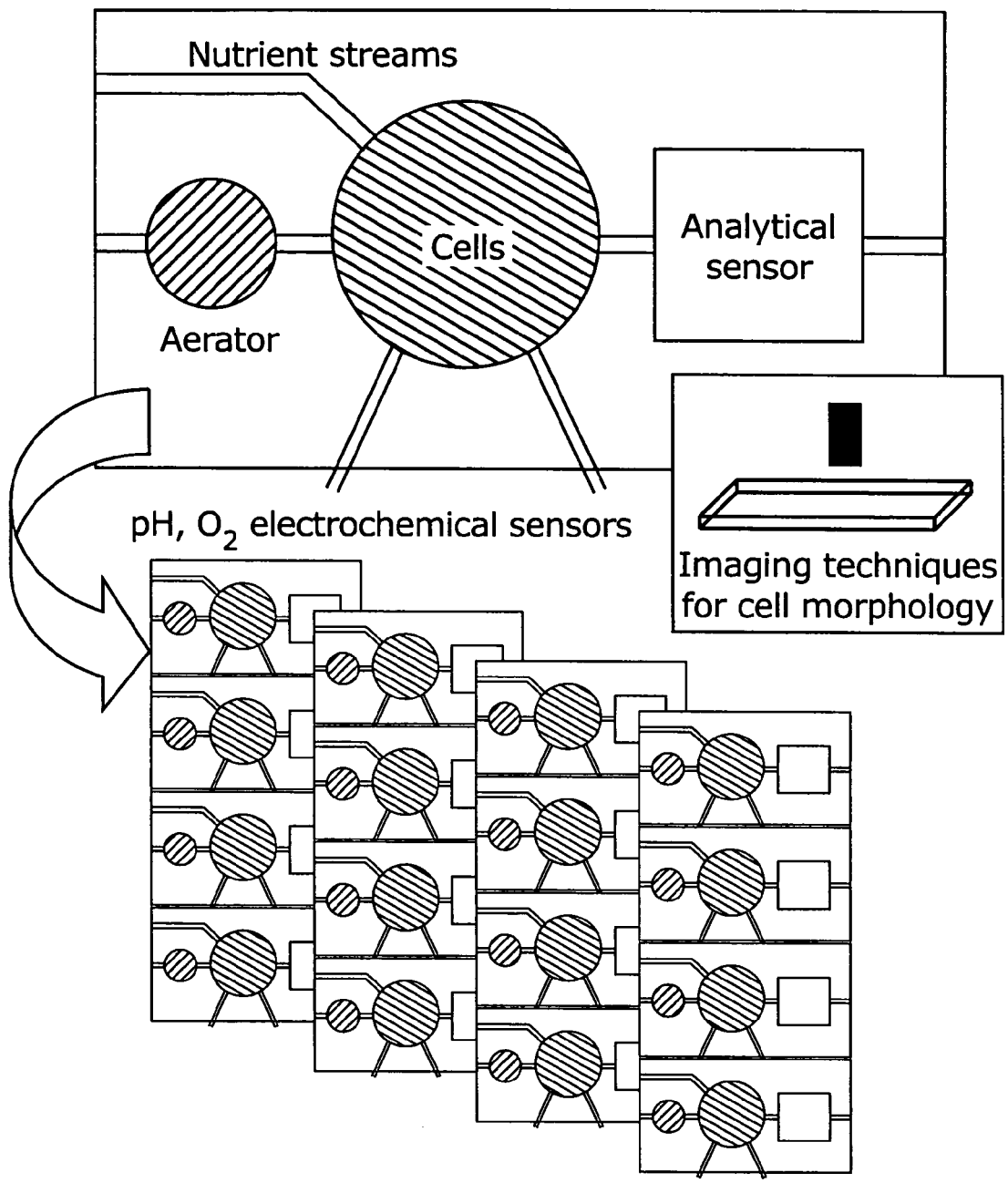
FIG. 3 (upper portion) shows a design of an embodiment of a microfermentor in which components are provided externally to the microfermentor vessel.

FIG. 3 shows a design of yet another embodiment of a microfermentor. The upper portion of FIG. 3 shows a single microfermentor unit. Each microfermentor includes a vessel in which cells are cultured and multiple channels extending from the vessel. The channels allow nutrient streams to enter the vessel and also provide means of contact between the interior of the vessel and various sensor devices. In this embodiment of the microfermentor, aeration is provided by means of a channel that allows communication between the microfermentor vessel interior and an external aeration chamber. This chamber may, for example, connect to a source of oxygen, may include a stirrer, etc. Multiple individual microfermentor units may be connected to a single aerator or each unit may have a dedicated aerator unit.

One of the goals of the invention is to provide an efficient platform in which multiple fermentations can be performed in parallel (e.g., simultaneously). Accordingly, the invention provides a system comprising a microfermentor array, by which is meant a plurality of physically connected microfermentors. The microfermentors are typically arranged in a regular geometry such as in mutually perpendicular rows, but this is not a requirement. Microfermentors are understood to be "physically connected" if they are arranged on or in a single substrate, attached to a common base, and/or connected to each other or to a central receptacle or chamber (e.g., via channels). The microfermentor arrays may include any number of individual microfermentor units. For example, in certain embodiments of the invention a microfermentor array includes at least 10 microfermentors. In certain embodiments of the invention a microfermentor array includes at least 100 microfermentors, at least 1000 microfermentors, or at least 10,000 microfermentors. The lower portion of FIG. 3 presents a sketch of an embodiment of a microfermentor array in which the individual microfermentor units shown in the upper portion of FIG. 3 are employed. (For illustrative purposes the columns are offset from one another.)

According to certain embodiments of the invention the system consists of multiple microfermentors, each with integrated bioanalytical devices, and operating in parallel. This system addresses the continuing demand in bioprocess science and engineering for fast and accurate analytical information that can be used to rapidly evaluate the interactions between biological systems and bioprocess operations. Moreover, the microfermentors provide the platforms for efficiently incorporating modern tools of biology (e.g., genetic profiling, enzyme catalysis, and bioinformatics) to improve bioprocess screening and development.

Figure 4A:
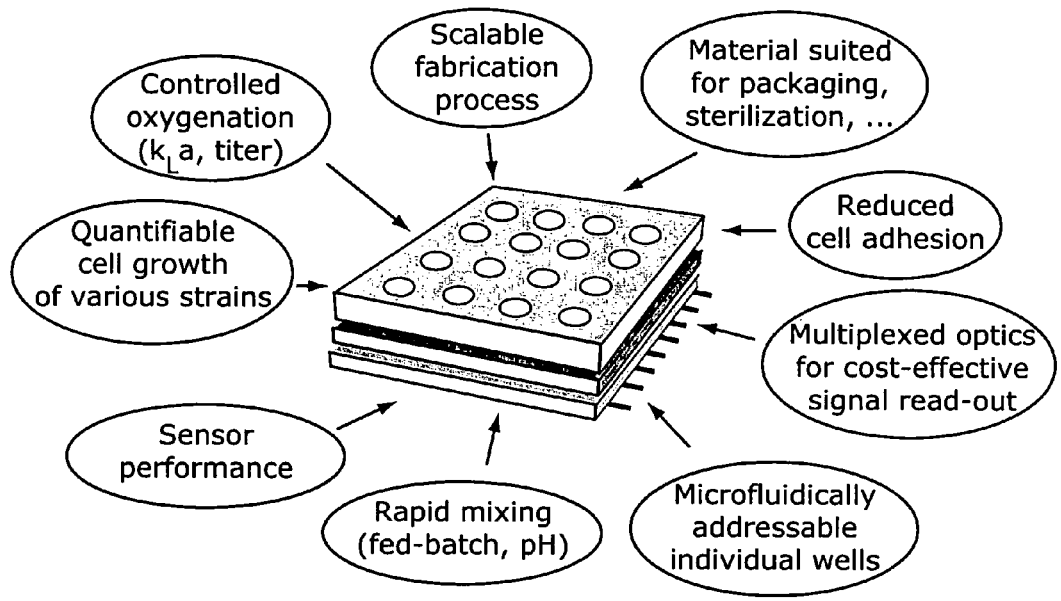
FIG. 4A shows a schematic of a platform for an integrated microfermentor array and associated system components.

FIG. 4A is a schematic diagram of a system comprising an array of microfermentors consisting of mutually perpendicular rows and columns of individual units. Any of the microfermentors described herein may be either placed within the wells of the plate depicted in FIG. 4A or the wells themselves may serve as individual microfermentor vessels. According to certain embodiments of the invention the system allows for integrating parallel operation of multiple microfermentors with fluid delivery and optical and electronic sensing elements. The microfermentors can be run in different modes including batch, fed batch, and continuous. According to certain embodiments of the invention the microfermentor units can be autoclaved and exchanged.

Figure 4B:
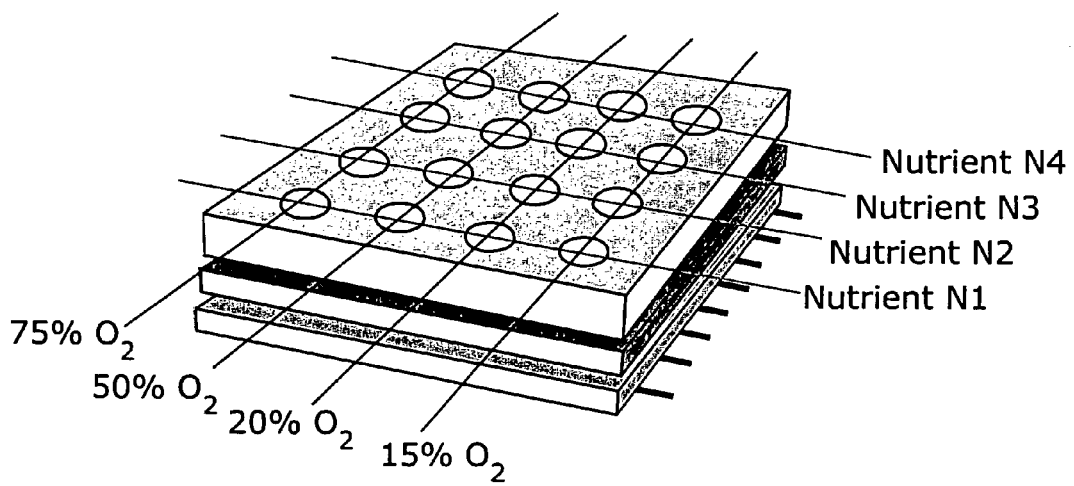
FIG. 4B shows a schematic of a platform for a microfermentor array and associated microfluidics in which bioprocess parameters are varied among the individual microfermentors.
Figure 4C:
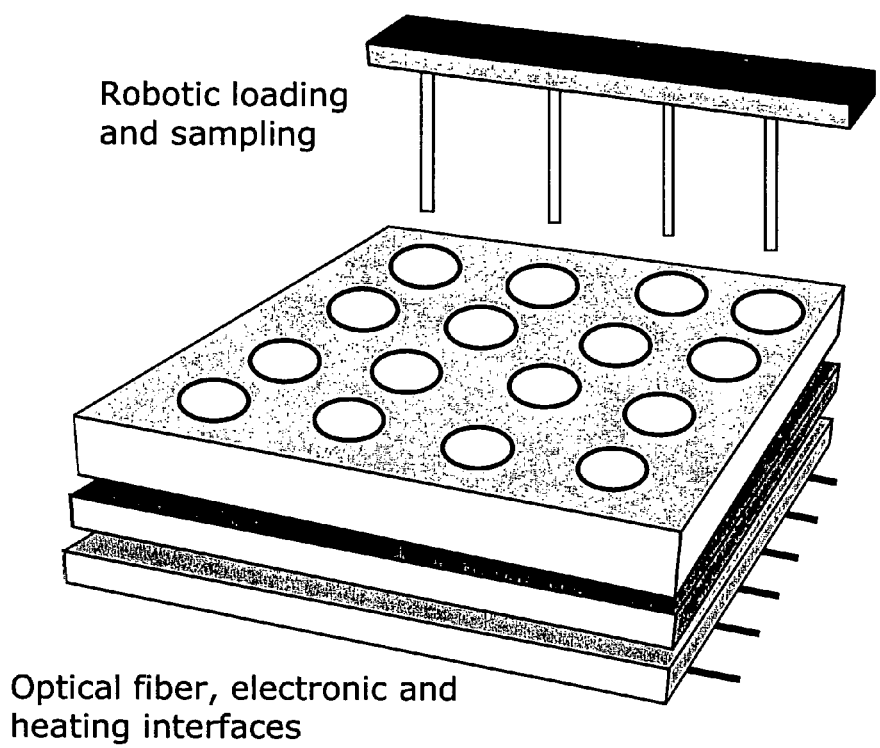
FIG. 4C shows a schematic of robotic loading and sampling of a microfermentor array.

The plate has chambers for multiple, parallel fermentation experiments. As shown in FIG. 4B, fluidic interface elements needed, for example, to inoculate the culture medium, to control pH, to add nutrient(s), or to remove portions of the cell culture may be integrated on the plate and in the system interface. This integration may be performed in such a way as to minimize mechanical manipulations and components needing sterilization. Elements present on or in the plate would typically include simple channels, valves, and connections to the system interface, etc. Other elements may also be included. Fluid control elements and delivery methods (e.g., pumps) may be housed in the system itself.

Similarly, according to certain embodiments of the invention reusable sensing elements are located elsewhere within the system whereas one-time use components are incorporated on or in the plate. For example, fluorescent dyes for dissolved oxygen and pH measurements may be incorporated into the plate, whereas optical fibers, lenses, and optical detection equipment may be situated in the system interface so that they could be used repeatedly for successive fermentation experiments. According to certain embodiments of the invention other means, e.g., optical means for measuring fluorescence and luminescence from biological species are incorporated into the system as described herein. Analogously, according to certain embodiments of the invention electronic sensing and automation means are incorporated into the system itself whereas simple actuator and sensing elements (e.g. electrochemical and capacitance) are incorporated into the plate.

According to certain embodiments of the invention the plate is packaged at the point of manufacture and may be pre-sterilized. When starting parallel fermentation, the plate is removed from the package and easily mounted in the system.

The plate and/or other system components can be manufactured by any of a number of standard microfabrication techniques, or combinations thereof, including but not limited to hot embossing, injection molding, electroplating, microelectrode discharge machining etc. According to various embodiments of the invention the plate is disposable or reusable depending, for example, on the particular application.

FIG. 4B is a schematic diagram of a system comprising a microfermentor array with microfluidic channels allowing control over parameters in individual microfermentors (see discussion of bioprocess control below). According to the approach depicted in FIG. 4B, by varying each of multiple parameters across different dimensions of the array, a combinatorial effect is achieved. For example, by employing four different values for dissolved oxygen and four different nutrient compositions across the two dimensions of the array, a total of 16 different culture conditions may be tested. According to various embodiments of the invention a single bioprocess parameter is varied across a single dimension of the array. According to certain other embodiments of the invention a plurality of bioprocess parameters are varied across one or more dimensions of the array.

Microfermentor arrays in which a plurality of substantially identical microfermentors operate in parallel offer a number of advantages. For example, it is possible to operate multiple microfermentors in parallel, terminate the fermentor run of one or more microfermentors at each time point of interest, and subject much or all of the contents of the microfermentor(s) to analysis. This offers an alternative to the approach of removing multiple samples from a single microfermentor, as would typically be done with a traditional bench-scale or industrial scale fermentor (although this approach may also be employed in the case of a microfermentor of the invention). The availability of multiple microfermentors operating in parallel thus offers higher flexibility for analysis.

The possibility of operating multiple microfermentors in parallel means that it will be possible to conveniently perform multiple substantially identical fermentation runs (e.g., multiple runs under identical or substantially identical conditions and/or in which the same organism is used) and to analyze the results of multiple such fermentation runs, which can greatly enhance confidence in the results. The degree to which conditions must be similar in order to be considered "substantially identical" may vary depending on the application and the particular condition under consideration. For example, two fermentation runs may be considered to occur under "substantially identical conditions" with respect to a particular parameter if the parameter varies between the two runs by less than approximately 20%, less than approximately 10%, less than approximately 5%, less than approximately 1%, or less than approximately 0.1%, depending, e.g., upon the particular parameter, the purpose of the fermentation run, etc. Rather than relying on results obtained from one or even a few large fermentations, the microfermentor arrays of the invention offer the possibility of obtaining data with increased statistical significance and of reliably identifying trends and variations, e.g., caused by different culture conditions.

In certain embodiments of the invention the microfermentor(s) and/or sensor(s) interface with standard laboratory robotics, with analytical equipment (e.g., HPLC, GC/MS, FTIR, etc.) and/or with data acquisition systems. In particular, in certain embodiments of the invention interfacing optical microscopy with the cell unit allows optical monitoring of cell morphology. In certain embodiments of the invention the microfermentors and microfermentor arrays are disposable.

The microfermentors, microfermentor arrays, and microfermentor systems of the invention may be mounted on or attached to a base and/or enclosed within appropriate housing. The housing may be provided with access ports, e.g., to allow entry and exit of wires, cables, tubes, etc. As used herein, according to various embodiments of the invention a "microfermentor system" includes one or more microfermentors or microfermentor arrays as described herein, optionally with associated microfluidic components, and one or more of the following: a plate or platform on or in which one more microfermentors or microfermentor arrays, optionally with associated microfluidics, may be mounted or housed; a chamber in which the microfermentors or microfermentor arrays, plates, or platforms may be enclosed; a pump; sensing and/or detection means; analytical equipment; robotics; software and computers, e.g., for data acquisition and/or bioprocess control; and any wires, cables, fibers, electronic components, etc., needed for operation of any of the foregoing system components. The system may include means for delivering energy to any component of the system, e.g., a power supply, and/or means for delivering excitation such as light, electromagnetic energy, or other forms of energy to the system.

Figure 25A:
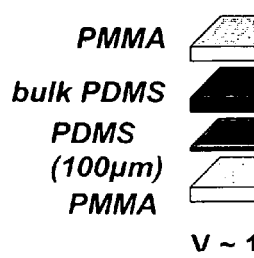
FIGS. 25A-25C show schematic diagrams of a microreactor of the invention that can be used for fed-batch fermentations.
Figure 25B:
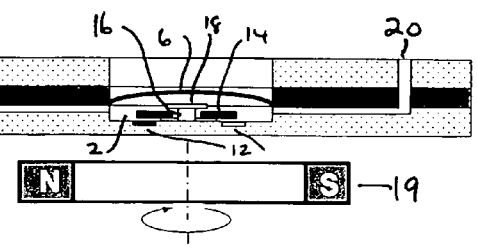

FIGS. 25B shows a schematic diagram in longitudinal section of the design of another microreactor of the invention, which can supply one or more reagents to the vessel during operation. FIG. 25A shows an expanded view of a layer structure that can be used to implement the microreactor. Alternate structures and implementation approaches resulting in the same overall configuration may also be employed. As shown in FIGS. 25A and 25B, a microreactor vessel 2 is housed in first body layer 4. As shown schematically, in this embodiment of the invention the vessel exists as a void in body layer 4 but other methods of implementing the vessel are within the scope of the invention. A gas-permeable membrane 6 is located between the first body layer and a second body layer 8. The membrane extends across the vessel. An optional third body layer 10 overlies the second body layer. Voids in the second and optional third body layers provide the gas-permeable membrane with access to the external environment. (By "external environment" is meant the environment immediately surrounding the structure from which the microreactor is fabricated. Thus if the microreactor is placed in a chamber, the external environment is the environment within the chamber.) In certain embodiments of the invention it may be desirable to construct the first body layer and, optionally, the second body layer, out of a material such as a rigid plastic and the second body layer out of a less rigid material, e.g., the same material as the gas-permeable membrane. Thus the outer body layers provide resistance to damage that may occur, e.g., during handling, and protect the more delicate membrane and second body layers. The first body layer may be supported by a substrate layer. Sensors (e.g., optical sensors) 12 may be mounted in depressions in the bottom of the microreactor vessel as shown in FIG. 25B or elsewhere in the vessel. The layers may be attached to one another using a number of different methods. They may be mechanically joined, e.g., using screws. Alternately, they may be bonded, e.g., using an adhesive or using thermal bonding. A combination of methods may be used.

Figure 30:
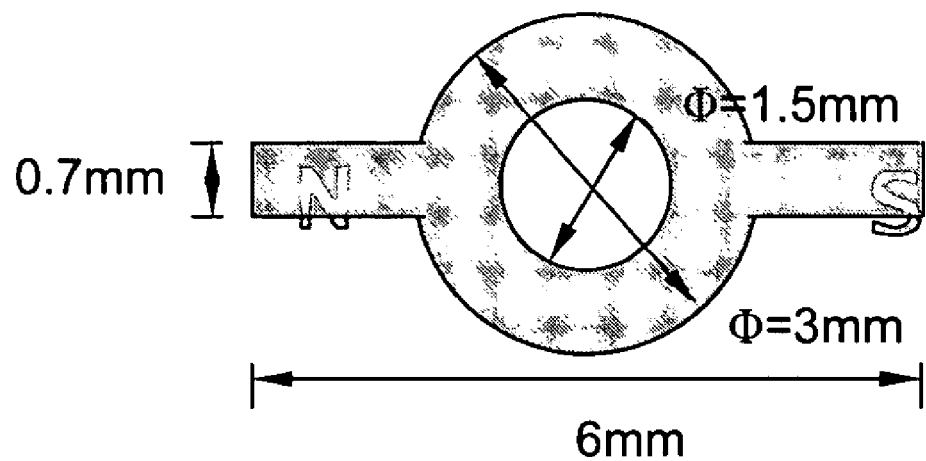
FIGS. 30A and 30B show a schematic diagram of top and side views of a miniature magnetic stirbar useful to provide active mixing for certain microreactors of the invention. Dimensions are included for representative purposes and may be varied depending, for example, on the size of the microreactor.

As shown in FIG. 25B, the microreactor optionally includes a miniature magnetic stirbar 14, also referred to as a spinbar. The stirbar may be mounted on a vertical post 16 that projects upward from the base of the microreactor vessel. The post may be made out of the same material as any the lower body layer or may be made out of a different material. FIGS. 30A and 30B show schematic diagrams of top (30A) and side (30B) views of a stirbar suitable for use in the microreactor. North and south poles of the magnet project outward from a collar that is used to mount the stirbar on the post. In certain embodiments of the invention the magnetic stirbar is made of a material having a particularly high magnetic strength such as neodymium, neodymium-iron, neodymium-iron-boron, etc. As depicted in FIG. 25B, a cap 18 retains the stirbar on the post. The stirbar sits on a shoulder that is elevated a small distance (e.g, approximately 100-200 µm) from the bottom of the reactor. The shoulder serves to elevate the stirbar in the reactor for better spinning, prevent it from scratching the reactor bottom and from scratching optical sensors. This structure is optional. As discussed further below, rotation of the stirbar may be achieved by use of a rotating magnetic field, depicted schematically as magnet 19 below the microreactor.

One or more channels 20 (e.g., microfluidic channels) extends from and communicates with the microreactor vessel. Such communication need not be continuous, e.g., there may be one or more valves located along the channel. The channels can be used to supply a variety of components to the microreactor vessel either before or during the microreactor run. For example, a first channel may be used to inoculate the culture with medium and cells (e.g., using a syringe). A second channel can be used to supply the vessel with a reagent during the run. Any of the channels may be blind in the sense of lacking an opening that communicates with the external environment following fabrication of the microreactor. Access to the channel may be gained by puncturing one or more body layers, e.g., with a needle. Certain materials will spontaneously reseal following withdrawal of the needle. Alternatively, it may be desirable to seal a channel using a material such as an adhesive. It may be desirable to include both types of channels, i.e., one or more channels that lacks a permanent communication with the external environment and one or more channels that includes a permanent communication with the external environment.

Figure 25C:
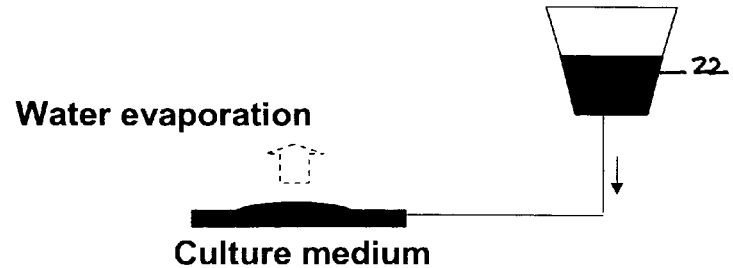

A variety of methods may be used to supply a reagent to the interior of the microreactor vessel, including both active and passive pumping strategies. FIG. 25C illustrates the principle of passive delivery of a liquid to the microreactor vessel. A reservoir 22 containing a liquid is provided and is connected to the vessel via a channel and appropriate tubing if necessary. Preferably the reservoir is located at an elevated position with respect to the vessel. Evaporation of water from the culture medium draws liquid from the reservoir into the channel and drives it into the vessel. The microreactor can be operated as a batch process when water is fed into the vessel from the reservoir or in a fed-batch mode when a reagent such as a nutrient (e.g., glucose), base, etc., is placed in the reservoir. This approach can be utilized for microreactors operating in parallel, in which case it may be desirable to provide a single reservoir connected by channels to the individual microreactor vessels.

Figures 26A, 26B:
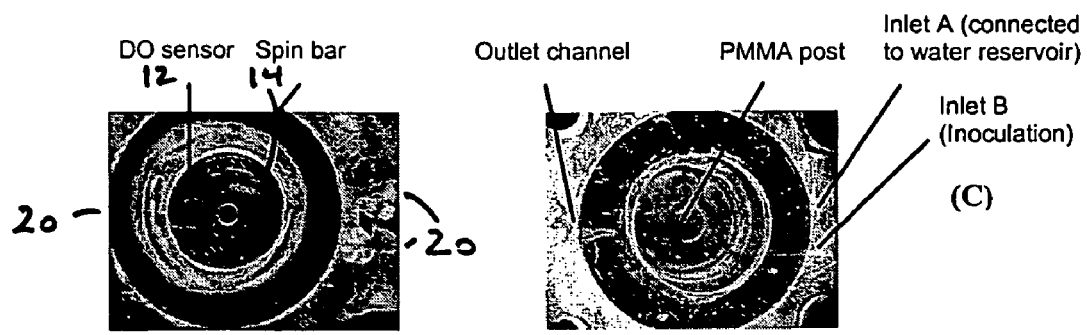
FIGS. 26A and 26B show photographs of a realized embodiment of the microreactor of FIGS. 25A-25C.

FIGS. 26A and 26B show photographs of a realized embodiment of the microreactor described above. FIG. 26A shows the microreactor with an empty vessel. A DO sensor 12 and stirbar 14 are visible as are three microfluidic channels 20. FIG. 26B shows the same microreactor, following a fermentation run. The channel inlets for connection to a reservoir and for inoculation are indicated. Turbidity of the culture obscures the sensor and stirbar.

Figures 27, 28A, 28B, 28C:
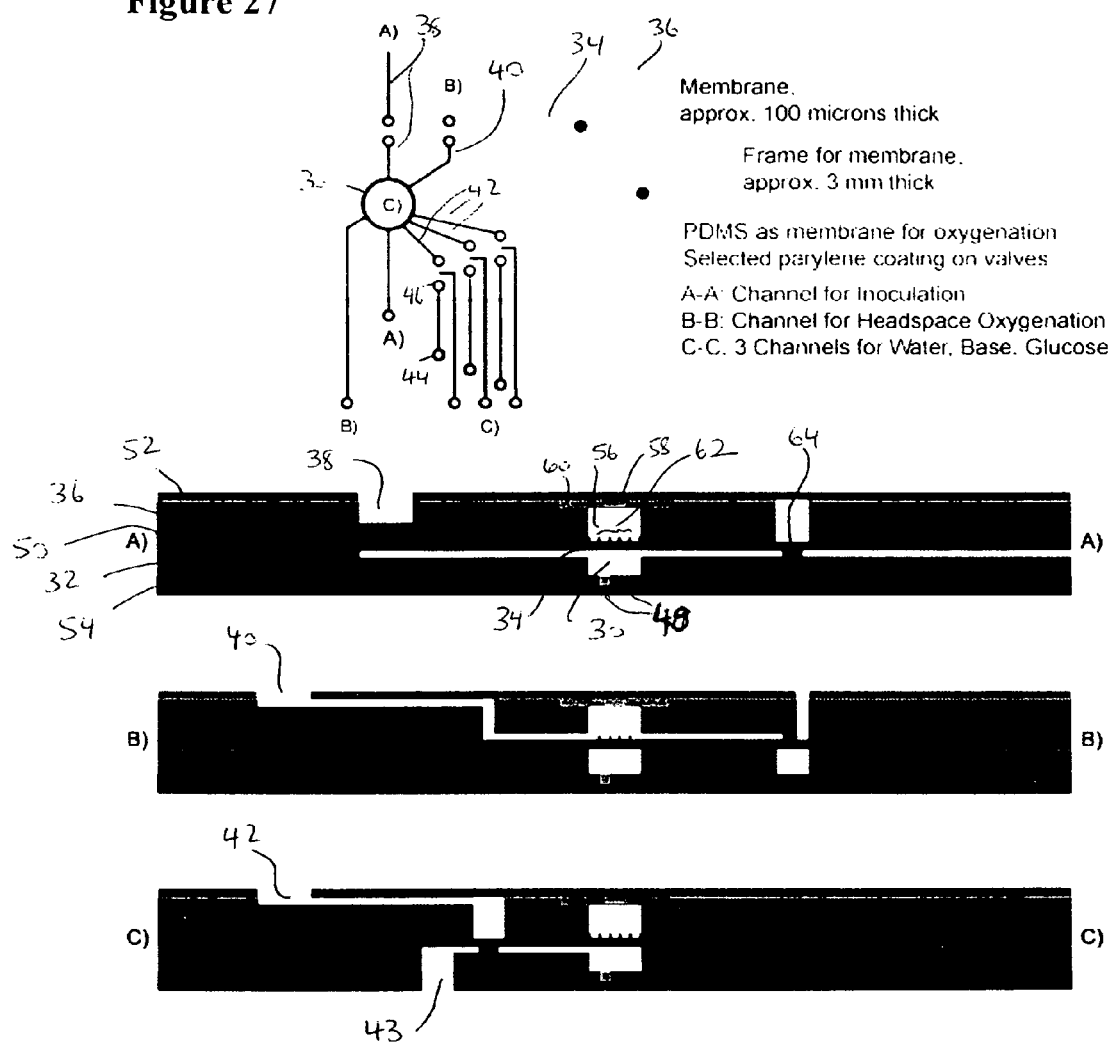
FIG. 27 shows a schematic diagram of a top view of a microreactor of the invention with a plurality of channels extending from and in communication with the microreactor vessel and additional channels in the body layers that define the microreactor vessel and headspace.
FIGS. 28A-28C show schematic diagrams of the layer structure and sensor locations of the microreactor of FIG. 27, illustrating the path taken by 3 different channels, labeled A-A, B-B, and C-C.

FIG. 27 shows a schematic diagram of a sectional view of another microreactor of the invention. The section is taken primarily in the plane of a gas-permeable membrane layer as described below, but certain elements such as the reactor vessel and channels, which are present in other layers are also depicted. The figure is color coded, with the colors representing elements that are present within different layers as shown in FIG. 28. For example, green represents elements in FIG. 27 that are present within the green layer in FIG. 28. FIGS. 27 and 28A-28C are most easily understood if considered together. In both figures, a plurality of channels communicate or potentially communicate with a microreactor vessel 30, which is housed in a body layer 32. A gas-permeable membrane 34 extends across the vessel. The membrane is optionally secured by another body layer 36, which serves as a frame or gasket for the membrane. The channels include channel 38, which extends from points marked A to A in FIG. 27, channel 40, which extends from points marked B to B in FIG. 27, and channels 42, which extend from points marked C to C in FIG. 27.

The open circles in FIG. 27 represent blind termini, which may be voids or holes in one or more layers of the structure. Access can be gained to channels connected to blind termini, or termini can be joined to one another, either by puncture with a needle or by opening a valve. The termini depicted in FIG. 27 may be located in different layers of the structure. For example, terminal 44 and terminal 46 are located in different layers, with terminal 44 located in a layer directly above the layer that contains terminal 46. A needle inserted at terminal 44 can be used to pierce through to terminal 44, thereby providing access to the vessel interior. It will be appreciated that when this method is used, the region to be pierced should be made out of a material that can be readily pierced.

FIGS. 28A-28C show 3 cross-sectional views of the layer structure of the microreactor of FIG. 27. The microreactor includes first body layer 32, gas-permeable membrane 34, second body layer 50, third body layer 36, a fourth layer 52 that overlies the second body layer, and optional substrate layer 54. Sensors 48 for measuring bioprocess parameters (e.g., oxygen, pH) in the vessel are embedded in the substrate layer but may be positioned elsewhere. The microreactor vessel is located within the first body layer. The third body layer serves as a gasket for the gas-permeable membrane. By "gasket" is meant a device used to retain fluids under pressure or seal out foreign matter, e.g., a seal made from a deformable material and compressed between plane surfaces. A void in the second body layer defines a headspace 56 for the microreactor vessel, by which is meant an empty space that does not contain liquid. A sensor 58 (e.g., a carbon dioxide or oxygen sensor) is located in communication with the headspace for sensing the contents thereof. The sensor may be embedded in a protective structure 60 (e.g., a Teflon ring surrounding the sensor). The fourth layer serves a protective function. The sensor may optionally be embedded in this layer. Sensors may also be placed within any of the channels. In order to prevent bulging of the gas-permeable membrane upwards into the headspace (which may occur if there is even a minor pressure difference as depicted schematically in FIG. 25B), an optional element 62 may be included. Element 62 may be, for example, a grid composed of the same material as body layer 50 or of a different material. The configuration of the element may vary, provided that it does not excessively prevent gas transfer across the gas-permeable membrane. It is generally desirable to reduce or minimize bulging of the membrane since such bulging can affect the accuracy of optical measurements. A variety of different methods can be used to reduce bulging.

FIG. 28A shows the path taken by channel 38 through the microreactor structure. Channel 38 may be used, for example, to inoculate the vessel with media containing cells. Starting near the left side of the figure, channel 38 enters the structure through voids in layers 52 and 50. The channel then encounters body layer 36, which must be pierced to allow access to the next portion of the channel. Continuing below, in body layer 32, the channel provides access to the microreactor vessel. The channel continues to the right of the vessel and comes to valve 64. The valve may be, for example, a portion of body layer 32 that projects upward into the channel. Pressure in the channel causes the overlying membrane to move upwards into void 66, thereby allowing fluid to flow beyond the valve into the rightmost portion of the channel. Valve 64 may be used to allow flushing of the microreactor vessel. Similar pressure-operable valves may be present elsewhere in the structure. Other types of valves may be used instead. It will be appreciated that a valve such as valve 64 can be actuated by applying pressure from either the left or right side of the valve.

FIG. 28B shows the path taken by channel 40 through the microreactor structure. Channel 40 may be used, for example, to supply oxygen to the headspace and/or to flush the headspace. Starting near the left side of the figure, channel 40 enters the structure through a voids in layers 52 and continues in layer 50. The channel extends down through layer 50 until encountering membrane 34. It continues leftward and enters the headspace. The channel exits the headspace on the opposite side and ends blindly. However, the portion of the membrane below the channel can act as a valve, being displaced downwards into the void below (in layer 32) when pressure is applied at the other end of the channel. Fluid may thus be forced through the channel, exiting through the void in layers 50 and 52 near the left end of the channel.

FIG. 28C similarly shows the paths taken by channels 42 and 43 through the microreactor structure. Channels 42 and 43 may be used, for example, to supply a reagent to the microreactor, e.g., during a fermentation run. As described above, displacement of portions of the gas-permeable membrane acts as a valve allowing fluid to enter the portion of the channel in direct communication with the interior of the microreactor vessel.

Figure 29:
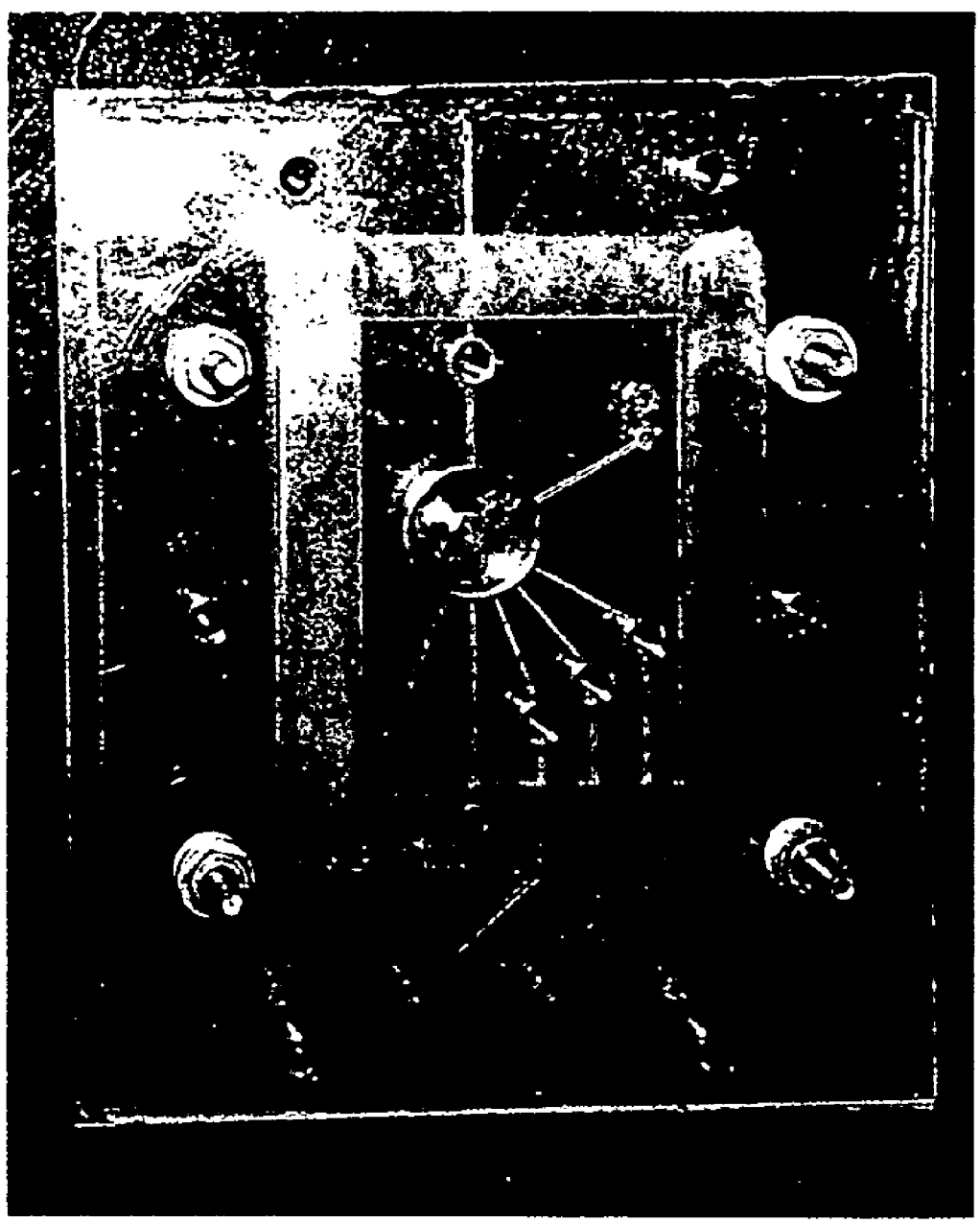
FIG. 29 shows a photograph of a realized embodiment of the microreactor illustrated schematically in FIG. 27 and 28A-28C.

FIG. 29 shows a photograph of a realized embodiment of the microreactor of FIGS. 27 and 28. The microreactor vessel, gasket layer and various channel elements are visible. The microreactor may optionally be provided with a stirbar as described above. Additional components such as reservoirs for feeding reagents, an oxygen supply, etc, may also be provided. The microreactor may be operated in a set-up such as that depicted in FIG. 31 A, which shows a microreactor structure with integrated stirbar and actuating magnet, connected fluidics that interface with one or more channels, and a syringe for inoculation. Optical elements for signal transmission, excitation, and detection are also depicted and are described in more detail elsewhere herein. Such elements may measure transmission, absorption, reflection, fluorescence, luminescence, etc.

In order to operate and monitor a plurality of microreactors in parallel, it is necessary to provide means for acquiring and analyzing data from multiple microreactor vessels. Rather than providing individual means for monitoring each microreactor (e.g., individual optical excitation and detection means, cameras, individual computing means, etc.) it desirable to efficiently utilize such relatively expensive components. In order to achieve this goal, it may be necessary to allow various components to move with respect to one another. The invention accordingly provides an apparatus for parallel operation of a plurality of microreactors comprising: (a) a chamber equipped with at least one element that removably supports or secures a microreactor tray inside the chamber, wherein the microreactor tray holds a plurality of microreactors; and (b) a supporting component that holds a signal transmission device, wherein the supporting component and microreactor tray are controllably movable with respect to one another. The microreactors may be, for example, any of the microreactors designed herein. FIG. 31B shows a schematic diagram of a set-up and instrumentation for operating a plurality of microreactors in parallel, as further described herein.

The microreactor tray provides support and appropriate positioning of the microreactors so that movement of the supporting component brings a signal transmission device into operably close proximity to at least a portion of the vessel of a microreactor held by the microreactor tray. By operably close proximity is meant a distance appropriate for effective functioning of a signal transmission device held by the supporting component. More generally, two components are in operably close proximity when the effective functioning of at least one of the components requires interaction with the other component (e.g., one component imparts force to the other, transmits a signal to the other, or acquires a signal from the other), and the components are positioned with respect to one another so that effective functioning can occur. The distance need not be optimal. In the case of a signal transmission device the distance between the components should allow for effective transmission of excitation energy from the relevant portion of the signal transmission device and/or effective collection of emitted or transmitted energy by the relevant portion of the signal transmission device (e.g., the portion of the device through which a signal is transmitted, such as an optical fiber face). For example, in the case of an optical signal transmission device used in contexts such as those described herein, operably close proximity will typically be a centimeter (cm) or less, i.e., the distance between the portion of the device through which the signal is transmitted and the component that emits or receives the signal will typically be a centimeter or less. In various embodiments of the invention operably close proximity is within 0.75 cm, within 0.5 cm, within 0.25 cm, within 0.1 cm, within 0.05 cm, or within an even smaller distance. Specifically, when an optical fiber is used to transmit excitation energy to and/or detect fluorescence from an optical sensor, such as the sensor foils described herein, the optical fiber face should be in operably close proximity to the sensor foil. When an optical fiber is used to transmit excitation energy to and/or detect transmitted energy from a microreactor, the optical fiber should be in operably close proximity to the portion of the microreactor into which the energy is transmitted or through which the transmitted energy is collected. It is noted that accurate movement of mechanical components to within such small distances is readily achievable by one or ordinary skill in the art using, for example, appropriate motors under microprocessor control.

The microreactor tray may be configured as a platform, i.e., a horizontal surface raised above another surface such as an adjacent area or floor (in this case the floor of the chamber). The microreactor tray can include locations such as apertures or depressions configured for mounting of a microreactor such as those described herein. In certain embodiments of the invention the locations are equidistant from one another. The microreactors or structures housing them may be mounted in or on the microreactor tray in any of a variety of ways and may optionally be secured to the tray. Various fasteners (i.e., mechanical connecting devices) can be used. For example, microreactors can be held with clips or spring-clamps or may be screwed into the tray (in which case the reactor tray contains appropriately threaded holes). Alternately, microreactors can be mounted on pins that project upwards from the surface of the microreactor tray or positioned within jackets that project upward from the surface of the tray. In general, any suitable means of mounting the microreactors can be used, provided they are mounted in a position and manner that permits the supporting component to bring a signal transmission device into operably close proximity to at least a portion of the vessel. Microreactor trays can be made out of numerous different materials, e.g., metals, plastics, etc.

The microreactor trays are flexible in that many different microreactor designs can be accommodated. In addition, in certain embodiments of the invention the microreactor trays can be removed from the apparatus, i.e., the trays can be removably mounted in the chamber. By removably mounted is meant that the trays can be conveniently removed from the interior of the chamber without causing structural damage to the chamber. Thus the trays are preferably not a contiguous part of a structural component of the chamber such as a side wall, base, etc. and are preferably not glued or adhered to the chamber. The chamber may include an element that engages a portion of the microreactor tray. Such an element contacts a portion of the tray or a matching element on the tray such that the two are reversibly attached to one another. Removable mounting means include, for example, screws, bolts, clips, tabs, slots, interlocking elements such a first element having a projection and a second element having a hollow space into which the projection is inserted, etc. The microreactor trays may thus be disposable. The invention therefore provides a disposable cassette comprising a microreactor tray configures to hold a plurality of microreactors. The microreactor tray is adapted for mounting in an apparatus of the invention. Preferably disposable microreactor trays are made of a light and inexpensive material, e.g., a light and inexpensive plastic.

Figures 32A, 32D:
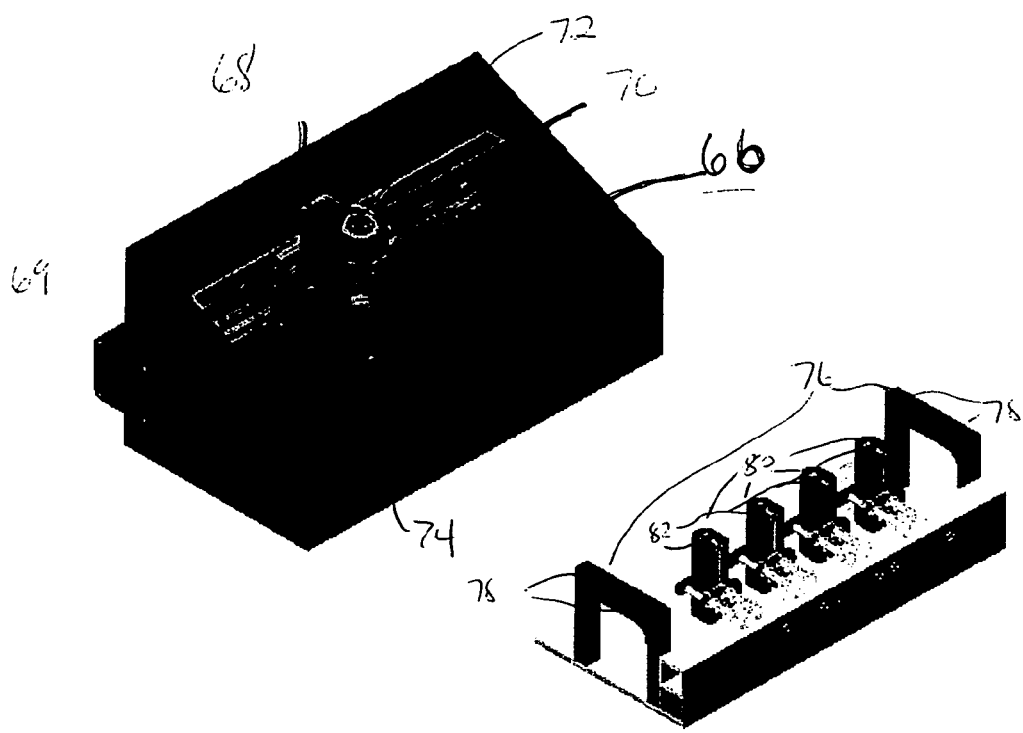
FIGS. 32A-32E show various views of and 32B show solid perspective views of portions of an apparatus for simultaneous operation of multiple microreactors.

FIG. 32A is a schematic diagram showing a solid perspective view of a chamber of the invention. Chamber 66 contains supporting component 68. The supporting component may resemble a bracket (e.g., a structure projecting from a wall or other vertical element for the purpose of providing support for another structural member), as shown in FIG. 32A. However, other configurations are also within the scope of the invention. Preferably the supporting component is stable enough to support the weight of a signal transmission device or portion thereof mounted in or on the component.

Supporting component 68 is attached to a horizontal threaded rod 70 that extends across a wall of the chamber. For purposes of description, this wall will be referred to as the back wall, and the wall opposite will be referred to as the front wall. The rod is attached to a motor via wires contained within housing 69. The motor causes rotation of the rod, thereby causing supporting component 68 to move along the rod. By causing the rod to rotate in either clockwise or counterclockwise directions, the supporting component can be made to move from left to right or from right to left in the chamber. Rotation of the rod and thus movement of the supporting component is under external control, i.e., is controlled by signals originating outside the chamber. For example, operation of the motor may be controlled via a controller, which may interface with a microprocessor that can be programmed so that the motor causes the supporting component to move at a predetermined speed and to stop at predetermined positions, e.g., opposite each of the mounted microreactors in sequence. The microprocessor may be housed in a computer, which may also be used to control transmission and collection of signals to and from the microreactors and/or to process the acquired data. A limit switch may be included to automatically stop motion of the supporting component at the ends of the rod.

Figure 32B:
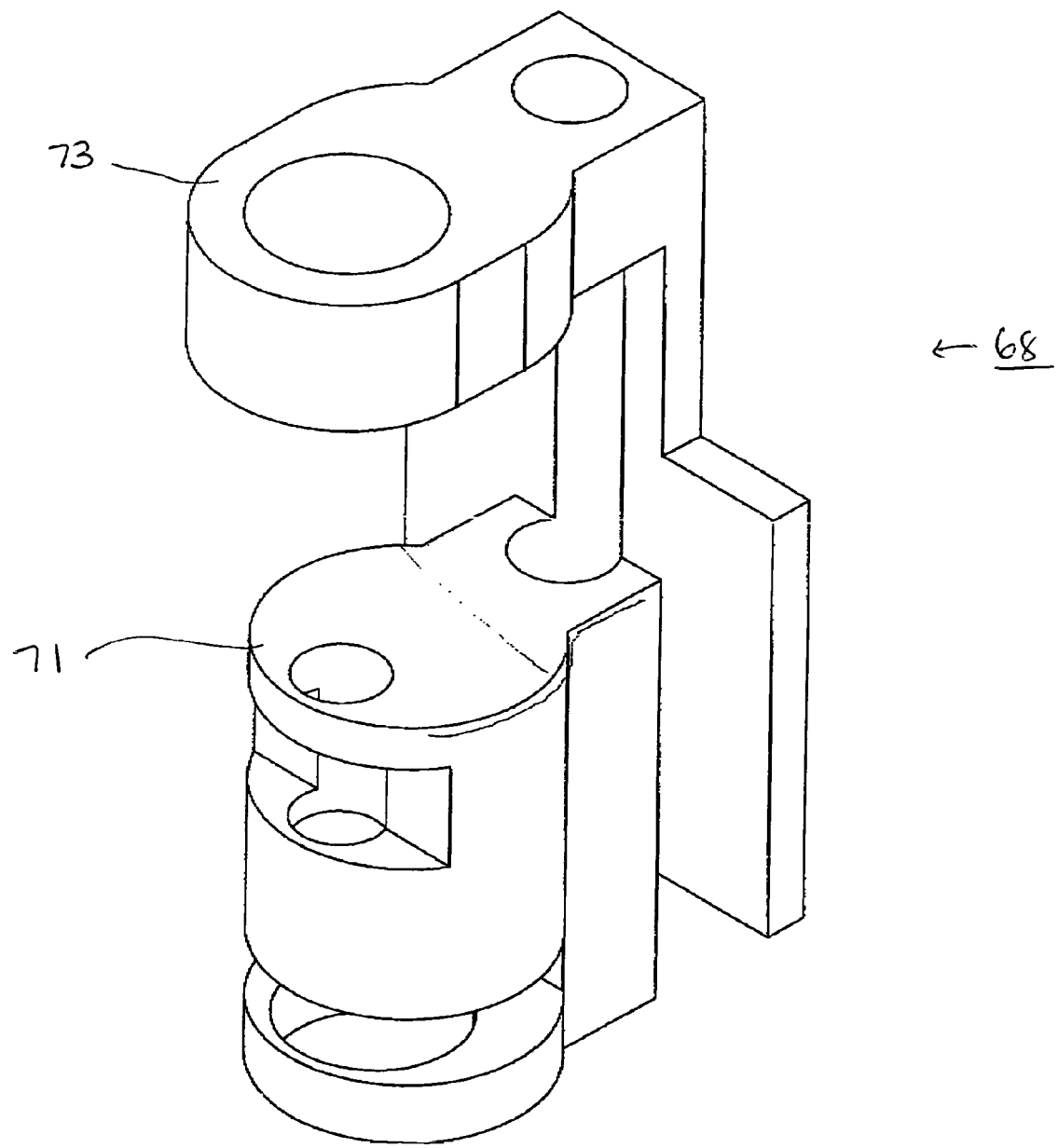
Figure 32C:
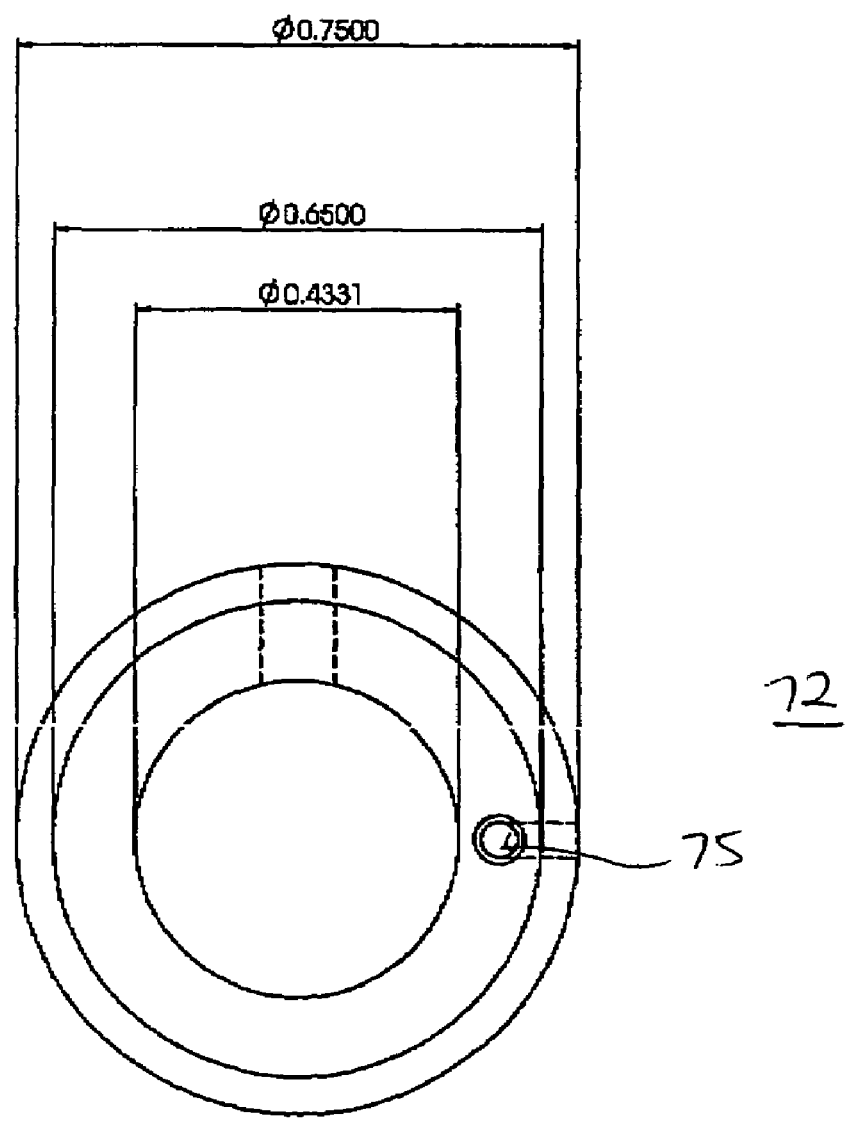

FIG. 32B depicts one embodiment of a supporting component of the invention in more detail. The supporting component includes lower portion 71 and upper portion 73, either or both of which (here both) may contain apertures in which a signal transmission device may be positioned. A removable tubular sheath is optionally mounted in the supporting component in either an upper portion of the supporting component or a in a lower portion of the supporting component or both, as shown in FIG. 32A. The sheath may be selected to structurally support a wide variety of signal transmission devices of interest. Removable sheath 72 has a relatively wide diameter and allows for passage and/or mounting of a variety of components. The interior of the sheath may contain structures such as rings projecting from the interior through which fibers or wires can be threaded. Removable sheath 74 contains an aperture with a relatively small diameter, suitable for threading of an optical fiber. FIG. 32C shows a schematic diagram of an upper view of a tubular sheath with a small ring 75 through which an optical fiber can be threaded. The sheath may contain various components either permanently or removably mounted therein. Among the devices that may be structurally supported using the supporting component (either within the sheath or elsewhere) are lenses, filters, mirrors, fiber optic cables, microscopes (or components thereof), and other image sensing devices (e.g., miniature cameras). A variety of suitable image sensing devices are known in the art. For example, CMOS image sensors such as the Agilent HDCS-1020 HDCS-2020 CMOS image sensors (Agilent Technologies, Palo Alto, Calif.), which include a highly sensitive active pixel photodiode array may be used. Charge coupled devices (CCDs) and intensified CCDs could also be used. Miniature cameras such as those available from Images SI, Inc., Staten Island, N.Y. are suitable. These ultra-miniature CCD cameras can be mounted on or in the supporting component to capture information about the state of the culture during a fermentation run. The invention therefore enables the acquisition of a wide range of physiological and/or biochemical information during an ongoing fermentation run. The use of cells that express fluorescent or luminescent proteins (e.g., green fluorescent protein (GFP) and numerous related proteins and variants, luciferase, etc.) can permit monitoring and visualization of a variety of cell processes.

Figure 33:
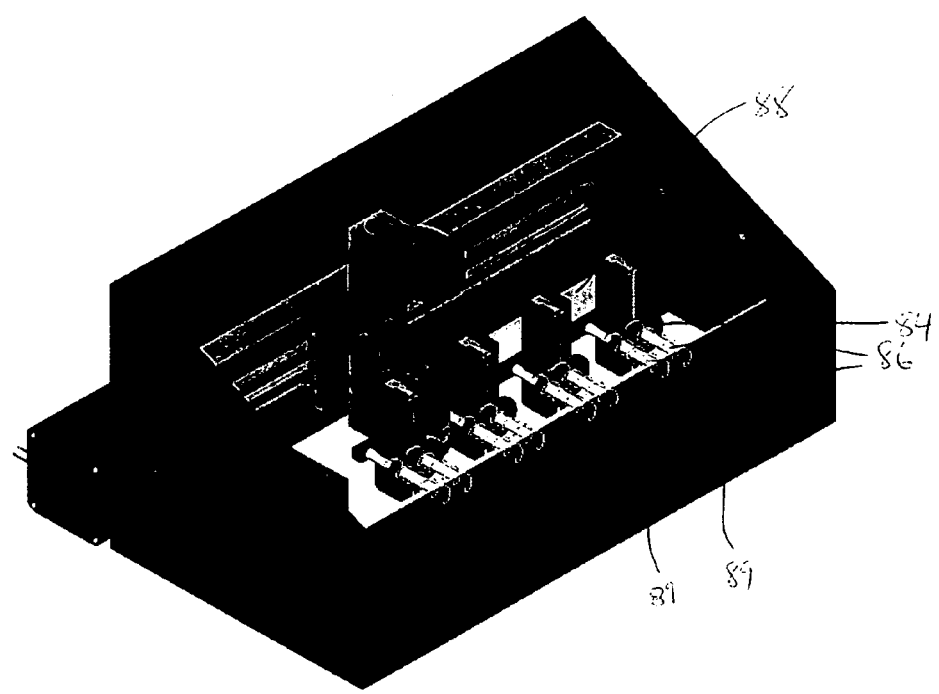
FIG. 33 shows a solid perspective view of an apparatus for simultaneous operation of multiple microreactors with the microreactor tray removed. Up to 4 microreactors may be operated simultaneously using the apparatus.

FIG. 32D is a schematic diagram showing a solid perspective view of a portion of the apparatus that has been removed from the chamber. When assembled, this portion is located in front of the supporting component, as illustrated in FIG. 33. FIG. 32D depicts posts 76 that are used to mount a microreactor tray. Holes 78 for the insertion of screws used to fasten the microreactor tray are indicated. However, a variety of other methods for either attaching the microreactor tray to the portion of the apparatus shown in FIG. 32D or to otherwise secure the microreactor tray within the chamber can also be used as mentioned above.

FIG. 32D also illustrates a plurality of support structures 80 for containing or supporting an actuating device. The height of the support structures is preferably selected so that an actuating device contained in or supported by a support structure is in operably close proximity to a microreactor mounted in the chamber. In other words, the height of the support structure is preferably selected so that an actuator will function appropriately to actuate another device located within a microreactor vessel in a microreactor mounted in the microreactor tray. The actuator may be, for example, a magnetic, electromagnetic, or a piezoelectric actuating device. Electromagnetic actuators include, for example, solenoids (with or without a core of magnetic material), electromagnets (e.g., cylindrical or coils with a core of magnetic material such as iron inside the coils), etc. One of ordinary skill in the art will appreciate that a great variety of electromagnetic actuators can be used. In certain embodiments of the invention the actuating device is a small solenoid or electromagnet that fits into pockets 82 of the support structure. Suitable electromagnets include miniature remote-controlled stirring devices available from Variomag (Daytona Beach, Fla.) referred to as the MINI or MINI P. These devices include an electromagnet and flexible foil cable that interfaces with an external controller (Telemodul 40C), which can in turn interface with a computer.

Figure 34A:
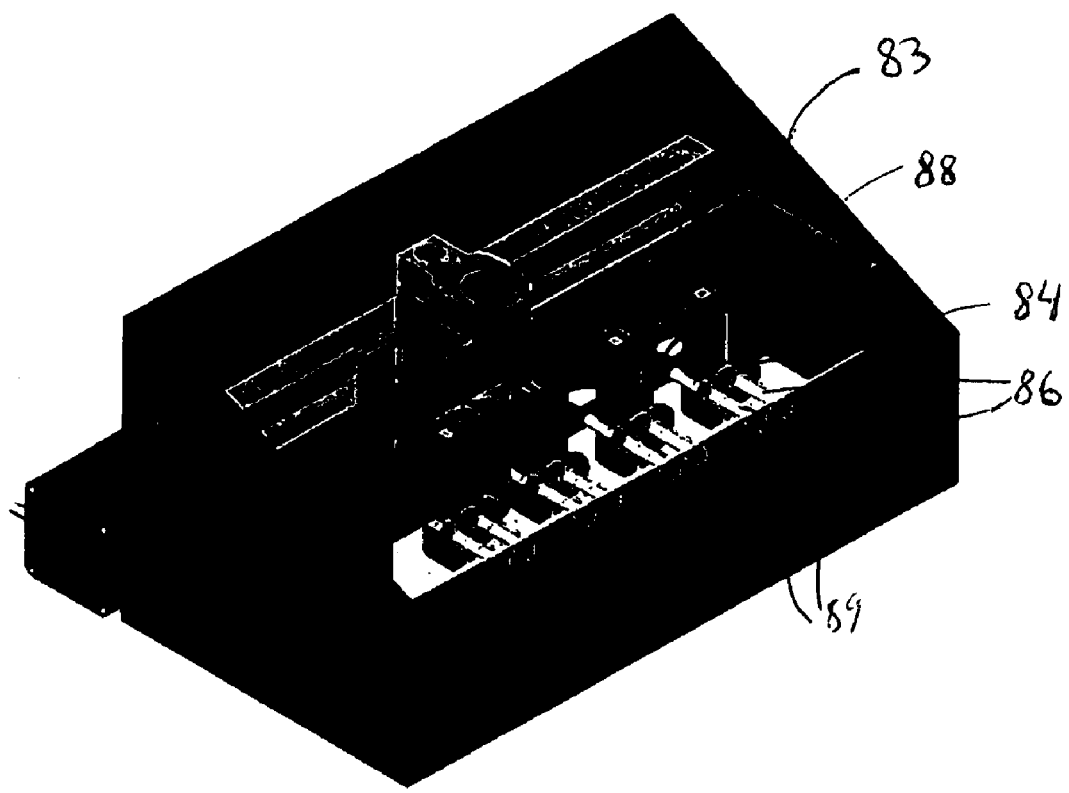
FIGS. 34A and 34B show solid perspective views of an apparatus for simultaneous operation of multiple microreactors with different microreactor trays mounted in position within the chamber.
Figure 34B:
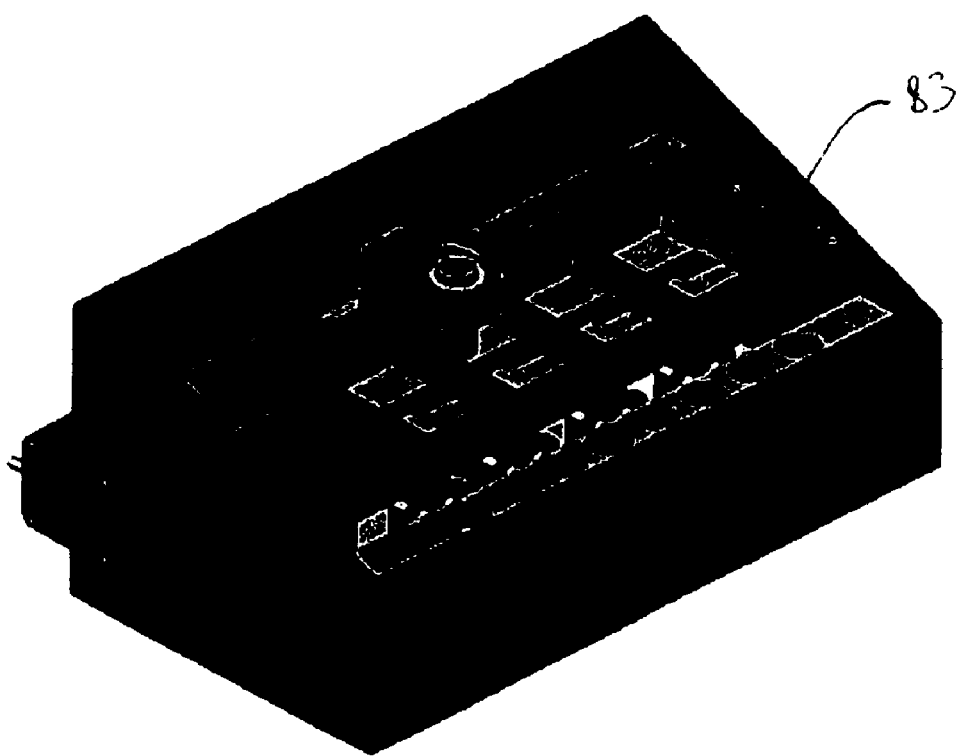

FIG. 33 illustrates the assembled apparatus. FIGS. 34A and 34B shows the assembled apparatus with different microreactor trays 83 mounted therein. (The tubular sheath mentioned above is not depicted.) In order to bring a signal transmission device into operably close proximity to a microreactor mounted in or on the microreactor tray, so that a signal may be transmitted to or received from the microreactor either from above or below the microreactor vessel, the portion of the supporting component in which the signal transmission device is held must be positioned appropriately with respect to the microreactors. However, this need can conflict with the requirement for positioning of the support structures for the actuators in those embodiments of the invention in which the support structures must be located underneath the microreactors. For example, to provide efficient stirring it is desirable to place a magnetic actuator directly under the stirbar. However, in order to obtain strong and reliable signals, e.g., optical signals, a signal transmission device such as an optical fiber should be positioned close to the optical sensors in the microreactor vessel.

Figure 32E:
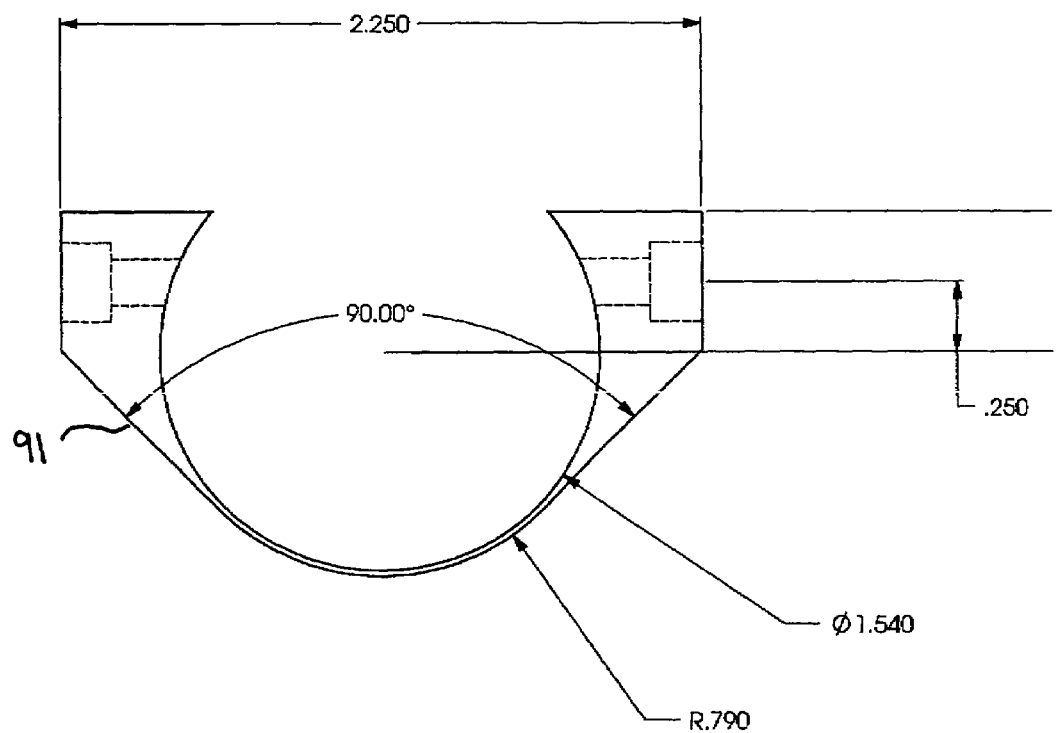

In the configuration pictured in FIGS. 33 and 34A-34B, the lower portion of the supporting component projects into the region occupied by the supporting structures. In order to accommodate both the supporting component and the support structures, in certain embodiments of the invention the support structures are slidably mounted on the floor of the chamber so that they may slide out of the way when the supporting component approaches. The sliding can be accomplished with a motor that is synchronized with the movement of the supporting component so that each support structure moves out of the way at the appropriate time. In other embodiments of the invention the supporting component itself exerts sufficient force on the support structure to force it to slide towards the front of the chamber. To this end, as shown in FIG. 33, the support structure may comprise an attaching element 84 containing holes on one or, preferably both, sides of the support structure. Rods 86 extend through the holes and are attached to the front of the chamber and also to a stopper bar 88 on the other side of the support structures. The rods are inserted through springs 89 that extend from the front of the chamber to the attaching elements. When the supporting component comes into contact with a support structure, it exerts force with a component directed towards the front of the chamber. The support structure slides forward, guided by the rods, and the springs are compressed. Compression of the springs generates a restoring force in the opposite direction to the compression. When the supporting component moves toward the next support structure such that the force component exerted by the supporting component in the direction of the front of the chamber is less than the restoring force exerted by the springs, the support structure moves back to its original position, guided again by the rods. The stopper bar prevents the support structures from moving too far in the direction of the back of the chamber. In this manner the supporting component can gain access to the microreactors when a measurement is to be made, while only temporarily interrupting operation of an actuating device held in or on the support structure corresponding to that microreactor. To facilitate sliding, the support structures may be mounted in a groove or track that minimizes friction, optionally with friction-reducing devices such as ball bearings. As shown in FIG. 32E, the supporting component may optionally contain an additional element 91 that is contoured so as to facilitate smooth contact and efficient force transmission between the supporting component and the support structure.

Figure 35A:
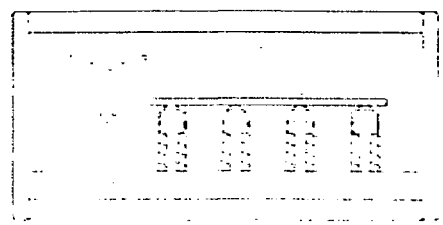
FIGS. 35A and 35B show sequential schematic diagrams of a top view of an apparatus for simultaneous operation of multiple microreactors during operation of the apparatus.
Figure 35B:
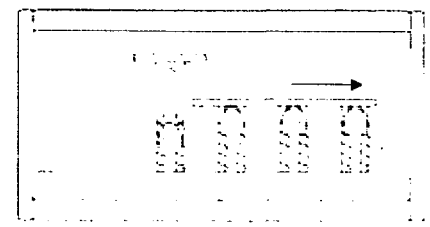

FIGS. 35A and 35B show schematic diagrams of the operation of an apparatus of the invention. In FIG. 35A, the supporting component is in its starting position at the left side of the chamber. Operation of the motor causes the supporting component to move to the right. As it encounters the leftmost support structure (FIG. 35B), it exerts a force on the support structure causing the support structure to move out of the way, toward the front of the chamber (which is downward as depicted in FIG. 35. When the supporting component moves further to the right, spring force restores the supporting component to its original position. The support structures are thus sequentially displaced by the supporting components and restored to their original position as the supporting component moves out of the way. This action may take place in both directions. In other embodiments of the invention the supporting component is moved toward the back of the chamber when being restored to its original position. At each microreactor position, movement of the supporting component may be halted for a sufficient period of time to allow transmission of and/or acquisition of a signal. Control of signal transmission and acquisition can be achieved using a microprocessor, optionally part of a computer. Different movement and signal transmission sequences can be selected by the user, as further discussed below.

Figure 36:
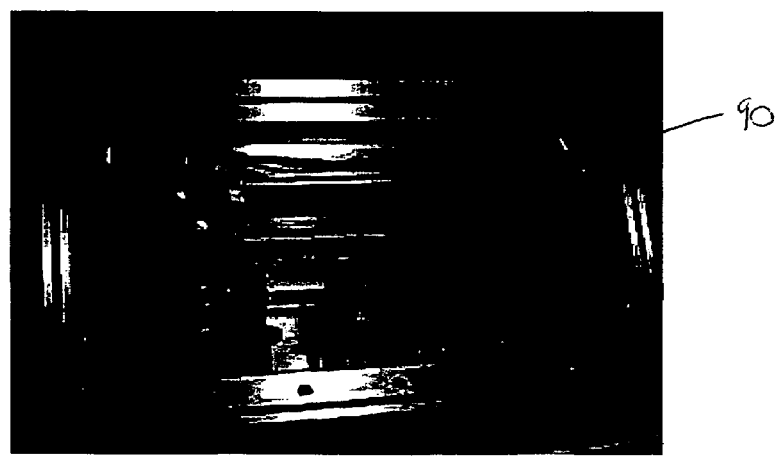
FIG. 36 shows a photograph of an apparatus for simultaneous operation of multiple microreactors with the microreactor tray removed.

FIG. 36 shows a photograph of a realized embodiment of the chamber described above with and depicted schematically in FIGS. 32-35. The supporting component, threaded rod, slidably movable support structures, attaching elements, rods, springs, stopper bar are numbered consistently with FIGS. 32-34. Electrical and optical cables are fed through the back wall as shown. The chamber is equipped with a gasket 90 that seals the chamber from the external environment when the lid (not shown) is applied.

Figure 37:
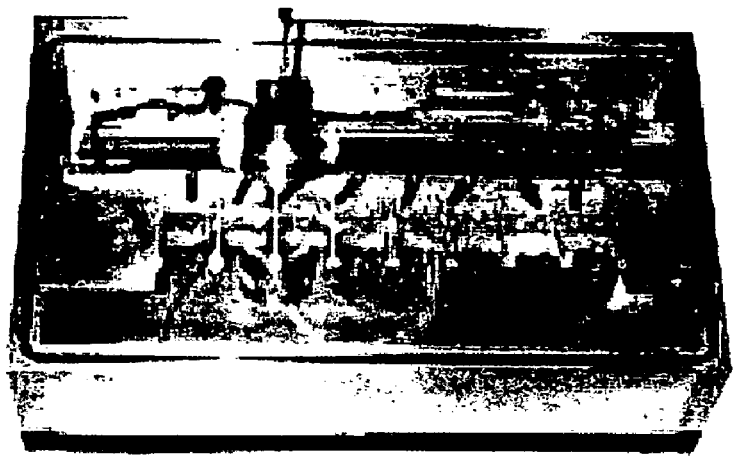
FIG. 37 shows a photograph of an apparatus for simultaneous operation of multiple microreactors with a microreactor tray in position within the chamber and 8 microreactors mounted in the tray.

FIG. 37 is another photograph of the apparatus showing 8 microreactors in place in the microreactor tray. The support structures were removed in order to facilitate visualization of the largely transparent microreactor structures.

Figure 38D:
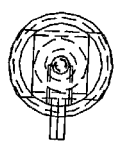
FIG. 38D schematically shows a rotating magnetic field created by the actuating device.
Figures 38A, 38B, 38C:
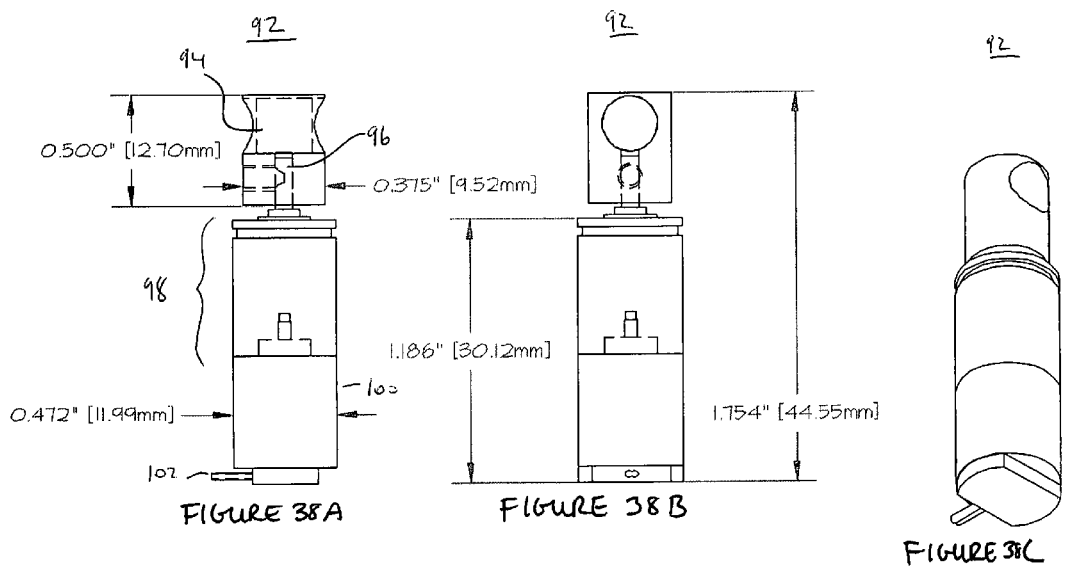
FIGS. 38A-38C show schematic diagrams of a support structure and magnetic actuating device suitable for actuating a miniature magnetic stirbar.

In another embodiment of the invention the actuator support structures need not be movable. Alternative support structures that are small enough so as to permit the supporting component to bring a mounted signal transmission device into operably close proximity to the microreactors are also within the scope of the invention, and chambers containing such support structures have been implemented. In certain embodiments of the invention the support structures comprise slender columns containing a rotating magnet, such as those available from Instech Labs (Plymouth Meeting, Pa.), e.g., the 606 stirring assembly. Such an assembly is pictured schematically in FIGS. 38A-38C. FIGS. 38A and 38B show cross-sectional views of stirring assembly 92 from different sides. The assembly contains a rotating permanent magnet 94, preferably made of a strong magnetic material such as neodymium, neodymium-iron, neodymium-iron-boron, etc. The magnet is mounted on a shaft 96 that is connected to a gear box 98 positioned above a motor 100. The motor drives rotation of the magnet via the gearbox. Action of the motor may be controlled externally, by signals transmitted via cable 102. Cable 102 connects to a suitable controller, microprocessor, etc. FIG. 38D schematically shows a rotating magnetic field created by the actuating device.

Figure 39:
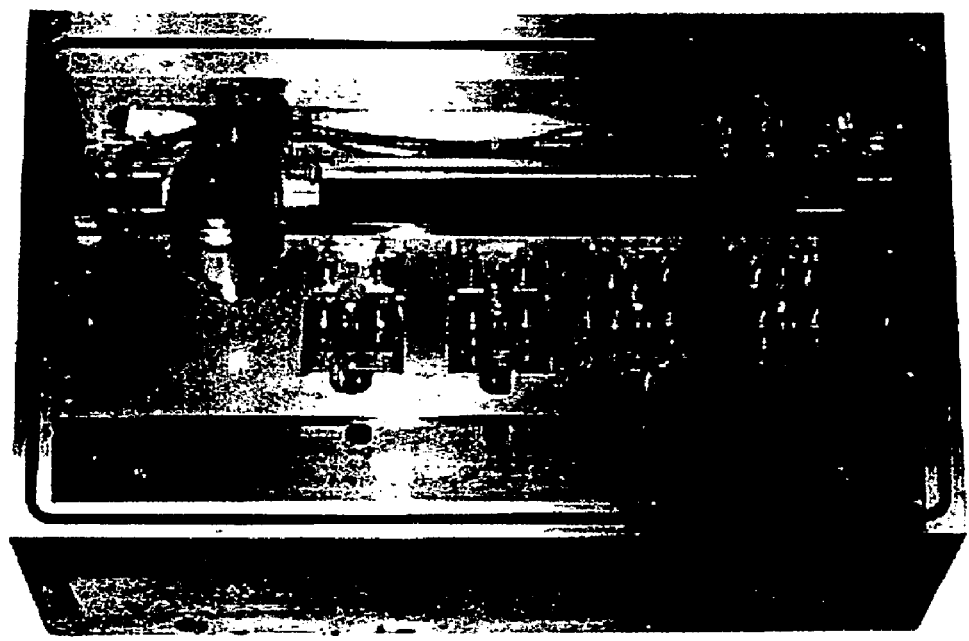
FIG. 39 shows an apparatus for simultaneous operation of multiple microreactors in which the support structures are not movable.

The assembly may be used to cause rotation of a miniature magnetic stirbar such as those described above, located in a microreactor chamber positioned in operably close proximity to the assembly. Typically the actuator would be located within several inches (e.g., 3-4 in. or less) from the top of the actuating device. It may be desirable to employ a shorter distance, e.g., 3 in. or less, 2 in. or less, 1 in. or less, 0.5 in or less, etc. FIG. 39 is an image showing an apparatus of the invention with these assemblies in place. The tops of the support structures containing the stirring motors and rotating magnet are far enough from the microreactors, such that the fibers and optics can easily pass in between the microreactor tray and support structures without becoming entangled. Other actuating devices could be similarly mounted.

The temperature inside the apparatus can be controlled using a variety of methods. A heater may be provided inside the chamber. Alternately, an external water bath flushing heated water through a fluid manifold in the base of the chamber can provide temperature control. One or more thermocouples for sensing temperature may be positioned anywhere within the device, preferably near the microreactors, e.g., mounted on the microreactor tray.

Figure 40A:
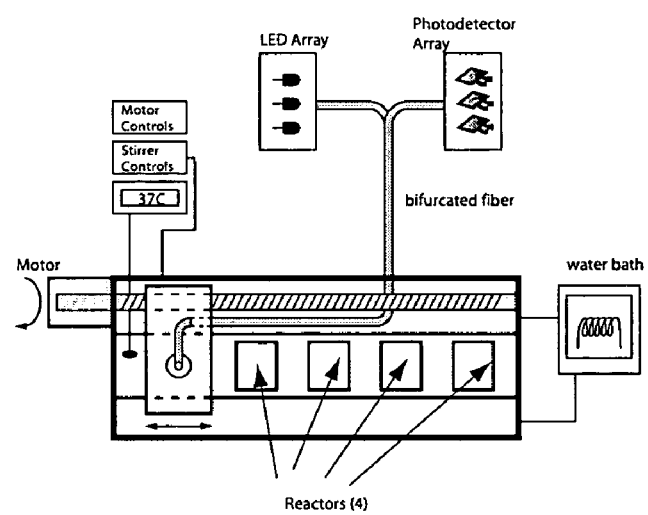
FIG. 40A shows a schematic diagram of instrumentation and components for a system to operate a plurality of microreactors in parallel.
Figure 40B:
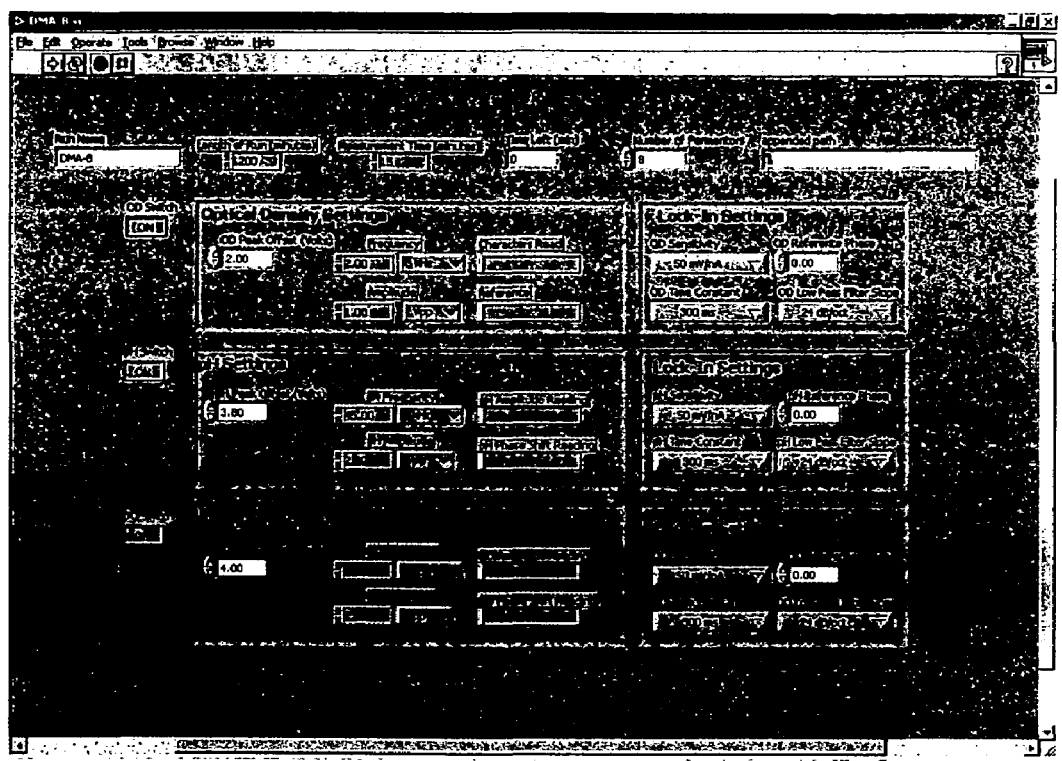
FIG. 40B shows a screen shot illustrating the graphical user interface created using the LabVIEW software suite for an apparatus for simultaneous operation of multiple microreactors. Run name, length of total run, sampling interval, and number of reactors can be set by the user in addition to settings for OD, DO, and pH sensitivity and other parameters.

FIG. 40A shows a schematic diagram of instrumentation and components for a system to operate a plurality of microreactors in parallel using the apparatus of the invention. To utilize the apparatus, the user prepares the strains for inoculation of the microreactor vessels and performs the inoculation procedure. Inoculation can be performed manually (typically through a channel as described above) or can be automated or performed in parallel. Operation of the apparatus may conveniently be controlled through a computer running a program such as those available in the LabVIEW software suite (National Instruments Corp., Austin Tex.). This program provides tools for creating a graphical user interface by which the user can control operation of the motors, temperature controller, excitation sources, signal transmission devices (e.g., optical fiber), etc. FIG. 40B shows a screen shot illustrating the graphical user interface created using the LabVIEW for an apparatus for simultaneous operation of multiple microreactors. Run name, length of total run, sampling interval, and number of reactors can be set by the user in addition to settings for OD, DO, and pH.

In a preferred embodiment of the invention the signal transmission device comprises an optical fiber. The supporting component moves over the microreactors and stops at each reactor, taking desired readings to monitor bioprocess parameters such as OD, DO, pH, $CO_2$, etc. The fibers are connected to excitation sources such as light sources with specific wavelengths (LED, laser, etc.), thus providing excitation for fluorescence readings or initial intensity for transmittance measurements. The emitted signals are collected with the fibers (by means of an additional lens or without a lens) either from the same side or from the opposite side of the microreactors. The signal is transmitted to appropriate signal detection elements, e.g., photodetectors, photomultipliers, etc. Signals can be transmitted electrically, optically, electromagnetically, by ultrasound, etc., and the signal transmission device will be selected accordingly, e.g., optical fiber, conductive wire, etc. In general, the invention encompasses the use of a variety of optoelectronic devices such as light-emitting diodes, (LEDs), solid state lasers, photodetectors, photomultipliers, photodiodes, arrays of any of the foregoing, etc., for excitation and signal detection purposes.

Figure 14:
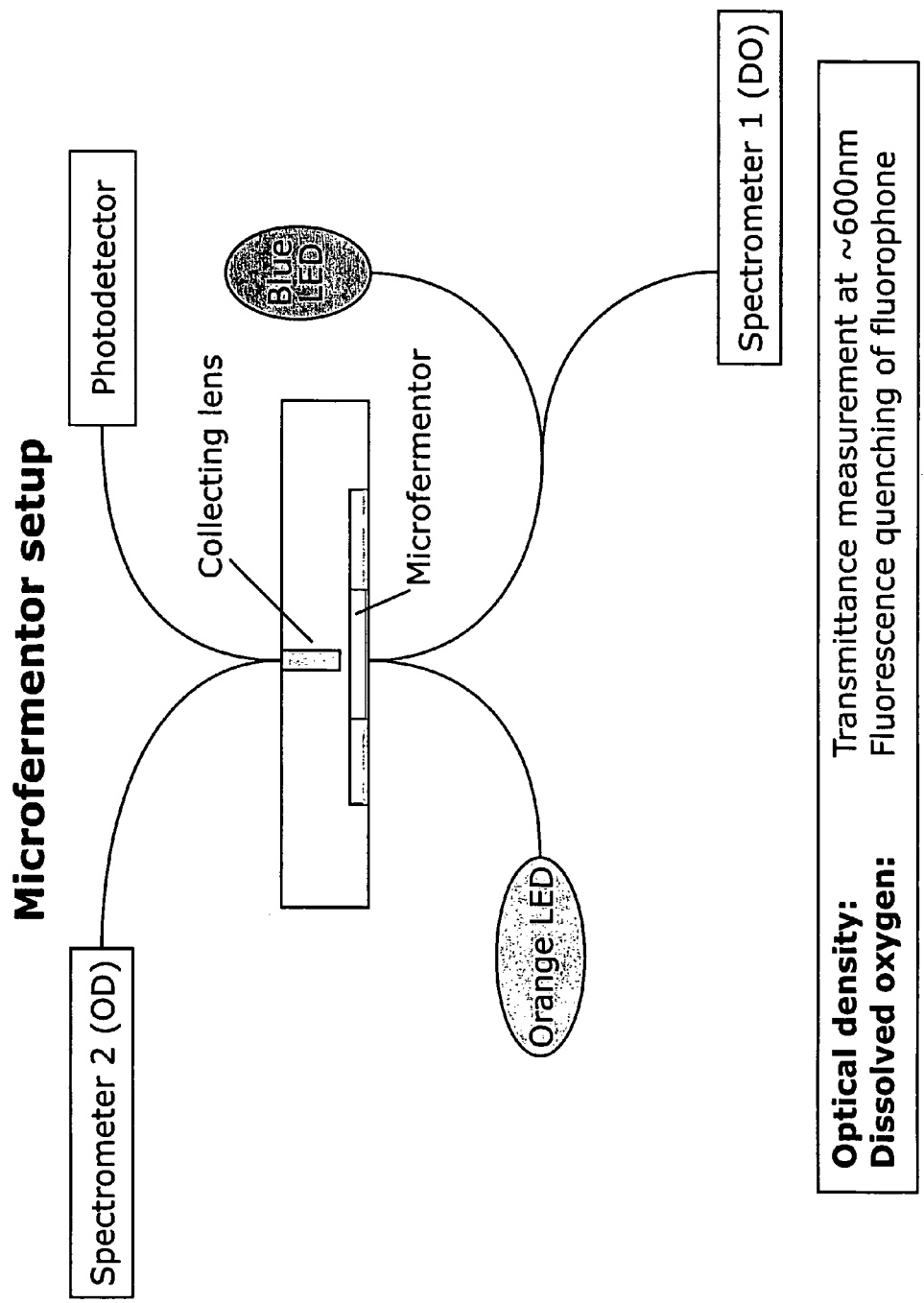
FIG. 14 shows a schematic of a microscale bioreactor system with associated optical excitation and detection sources.
Figure 31:
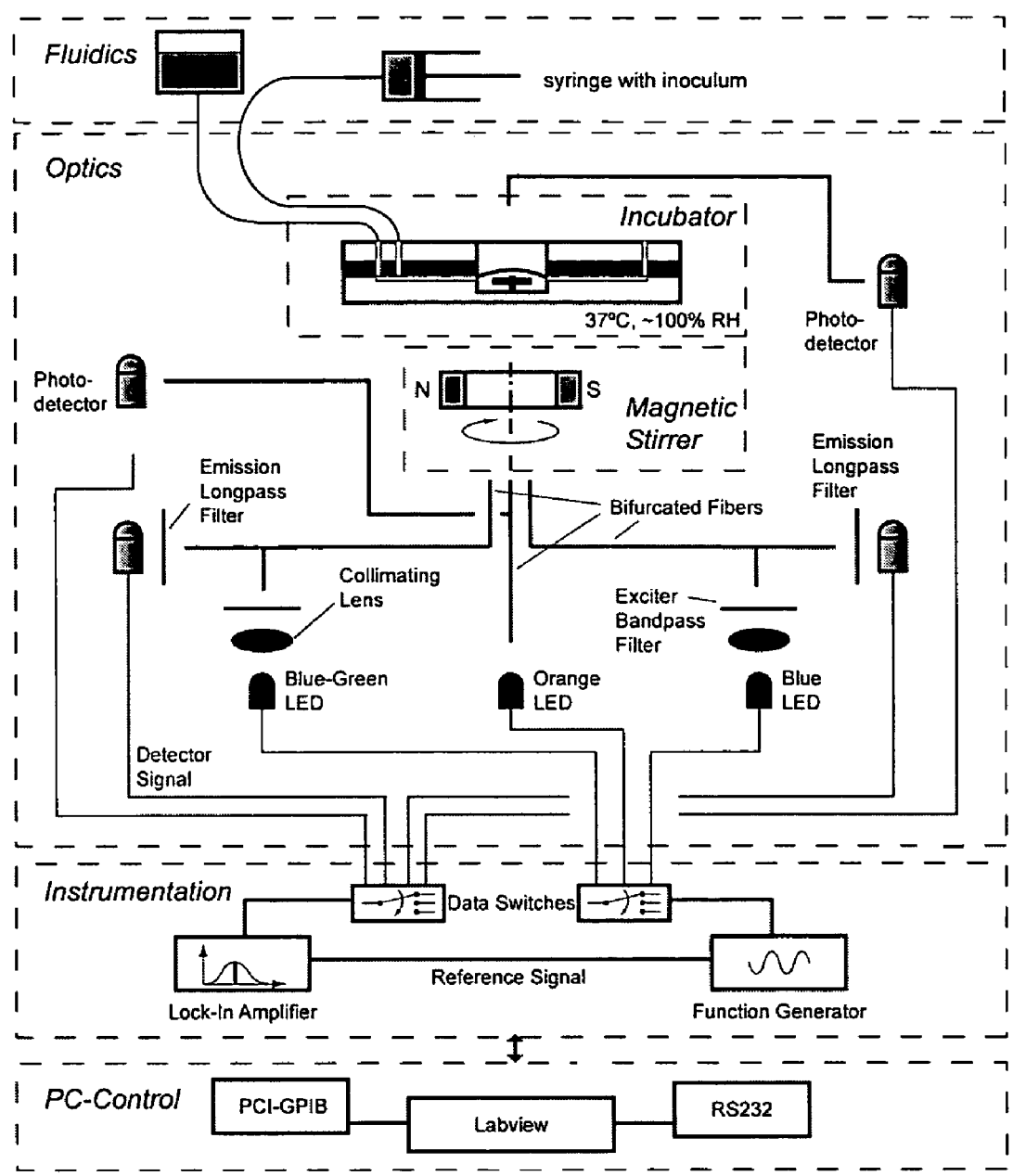
FIG. 31 shows a schematic diagram of a set-up for operating a microreactor of the invention (in this case a microreactor with integrated stirbar and fed-batch capability). The diagram shows the instrumentation, optics, magnetic stirbar and actuating magnet, chamber in which microreactor is mounted, and fluidics for reagent feed and culture inoculation (syringe not attached during run). Components not drawn to scale.

In one implementation of the system, relay switches are used to multiplex the different signals to and from the instrumentation as shown schematically in FIGS. 14 and 31. The instrumentation comprises a function generator that controls the excitation light and a lock-in amplifier for the emission light. Bioprocess parameters are collected for each microreactor and may be transmitted to a computer for storage and/or analysis. In other embodiments of the system, excitation sources and detector elements are integrated into a wall, floor, or lid of the chamber itself. Signals can be collected in PC cards, thereby reducing the need for bulky instruments. In a third configuration, a separate instrumentation entity is provided, which holds all the necessary instrumentation and communicates with a computer through one or more interfaces. To perform a fermentation run, a program may be downloaded into a memory device, e.g., an electrically erasable programmable read-only memory (EEPROM) or other memory device held in the instrumentation entity. Various parameters (e.g., sampling interval, number of microreactors, etc.) can be modified for each run. Recorded data can be transferred to a computer for additional storage and/or analysis at any time during or following the run.

Figure 41:
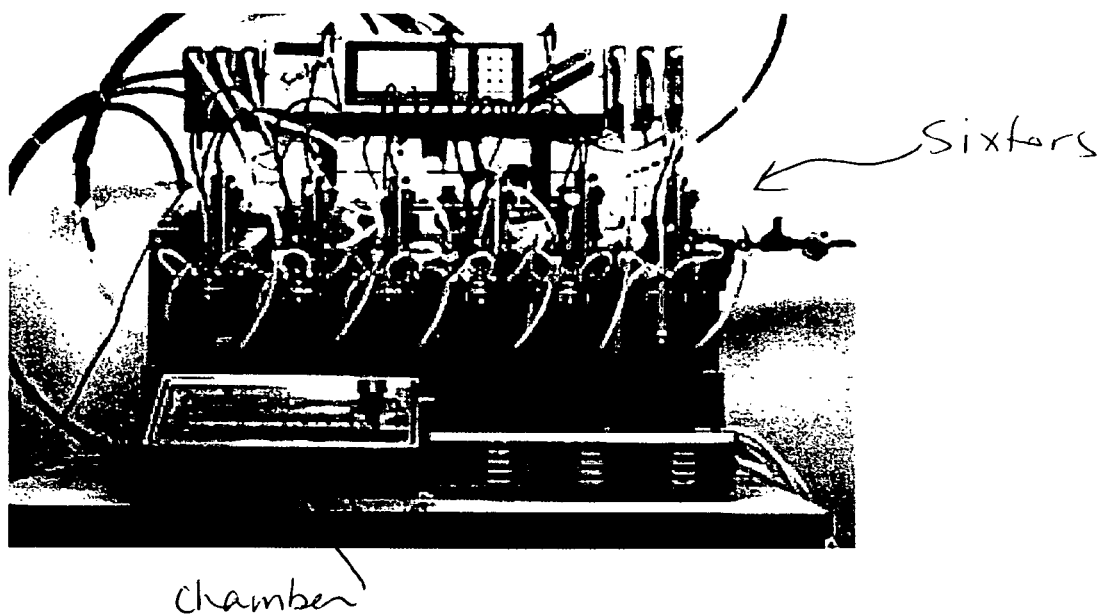
FIG. 41 shows a size comparison between the apparatus of the invention and a commercially available system (Sixfors) for performing multiple fermentations in parallel.

In general, the various components of the apparatus can be made out of a variety of different materials, e.g., metals such as aluminum, stainless steel, brass, etc., rigid plastics such as the acetal resin Delrin®, etc. If actuating devices relying on magnetic force are to be used, it is preferable that the support structures, particularly portions that are close to or in contact with a magnet, are made of a nonmagnetic material. FIG. 41 shows a size comparison between the apparatus of the invention in the front of the figure and a commercially available system (Sixfors) for performing multiple fermentations in parallel, which is located behind the apparatus of the invention. It is evident that the apparatus of the present invention achieves a considerable reduction in size.

It will be appreciated that numerous other configurations for a chamber equipped with at least one element that removably supports or secures a microreactor tray that holds a plurality of microreactors inside the chamber and a supporting component that holds a signal transmission device, wherein the supporting component and microreactor tray are controllably movable with respect to one another may be envisioned by one of ordinary skill in the art. Such configurations fall within the scope of the present invention.

B. Fabrication Techniques

A wide variety of fabrication techniques may be used to construct the microreactors and microfermentors of the invention. As described in more detail in Example 1, in certain embodiments of the invention microfabrication using soft lithography is employed. This technique offers a number of advantages. For example, soft lithography allows the rapid production of microfermentors with different shapes and sizes, allowing efficient optimization of these parameters.

In certain embodiments of the invention, e.g., for purposes of large scale manufacture it may be preferable to select alternative techniques or materials. For example, in certain embodiments of the invention the microfermentor is fabricated at least in part from a polymeric material such as polystyrene, polycarbonate, polypropylene, or polytetrafluoroethylene (TEFLON™), copolymers of aromatics and polyolefins, which can be processed using standard methods such as free-form molding, micromolding, injection molding (e.g., reaction or thermoplastic injection molding, punching, etc.), hot embossing, CNC machining, laser direct write, microelectro discharge machining, etc. See, e.g., (78). An aeration membrane can be incorporated as a structural component of the microfermentor vessel or into a vessel wall. Incorporation may occur during fabrication of the remainder of the vessel or the aeration membrane may be added later. For example, an aeration membrane may be attached using any of a variety of techniques, e.g., with adhesive, heat fusion, etc.

In certain embodiments of the invention the microfermentors and microfermentor arrays are fabricated using standard semiconductor manufacturing technology as described, for example, in (77). For example, a silicon wafer (which may be mounted on a rigid substrate such as glass or plastic) may be used to form the lower layer of the microfermentor, which can then be etched to form a well that functions as a vessel for growth of cells. Additional layer(s) of semiconductor materials such as silicon nitride may be deposited on the lower layers (e.g., by chemical vapor deposition, physical vapor deposition, and electrodeposition), with wells and channels etched into one or more of these layers. As described above, a microfermentor array including multiple wells can be formed, and the wells may be connected via channels to each other, to the edge of the wafer, or to a central receptacle, which may be used to supply nutrients, oxygen, or cells to the interior of the well and/or to remove samples.

In certain embodiments of the invention a manufacturing technique that allows substantially integrated and simultaneous fabrication of some or all of the structural components of the microfermentor (i.e., components such as bottom, top, and side walls necessary to form a vessel within which cells can be cultured) and one or more functional components (e.g., oxygen delivery means, sensors, etc.) is selected. In certain embodiments of the invention a manufacturing technique is selected that allows fabrication of some or all of the structural components of the microfermentor directly on a substrate or base. Such an approach contrasts, for example, with a manufacturing technique in which it is necessary to fabricate part of the vessel (e.g., the side walls) and then attach it to a base.

C. Materials and Surface Modification

In certain preferred embodiments of the invention biocompatible materials (i.e., materials that will not significantly inhibit or adversely affect cell viability and proliferation and/or adversely affect other biological components such as metabolites produced by the cells) are employed for those portions of the microfermentor that are in contact with cells or are used to deliver cells or other materials to the vessel. Suitable materials include silicon, silicon dioxide (e.g., glass), ceramics, plastics such as polycarbonates, acrylates, polypropylenes, polyethylenes, polyolefins, or other biocompatible polymers such as silicones (for example, PDMS), fluoropolymers, etc. In addition, nonbiocompatible materials (e.g., certain metals) can be employed provided they are coated with a biocompatible material.

PDMS represents an attractive choice for microfermentor fabrication (both for the aeration membrane and as the structural material of the microfermentor itself) for a number of reasons. PDMS is highly permeable to gas, which allows sufficient oxygen to diffuse into the medium while simultaneously allowing carbon dioxide and other gases to escape. PDMS is highly hydrophobic, which minimizes water loss to evaporation. It is biocompatible, can withstand autoclaving temperatures, and is transparent to visible light.

The small sizes of the microfermentors and the other features within these systems lead to surface-to-volume ratios that are well above those in conventional macroscale operations, accentuating the importance of providing compatible interfaces for operation. Protein denaturation and non-specific adsorption provide pathways that could potentially alter the performance of the microfermentors. Thus in certain embodiments of the invention surfaces in contact with cells and/or biological components such as metabolites produced by the cells are altered in order to reduce these effects. Such surfaces may include both the interior of the microfermentor vessel and any channels, etc., that may contact either cells or other biological components such as cell products.

In certain embodiments of the invention surfaces in contact with cells or other biological components are altered in order to inhibit or promote cell adhesion. For example, in the case of bacterial cells, cellular adhesion to microfermentor surfaces is undesirable and surfaces in contact with cells may therefore be modified to reduce cell adhesion. Similarly, adhesion of cell products such as proteins may be undesirable. Adhesion may reduce the efficacy of aeration membranes and the accuracy of sensors. In addition, adhesion may contribute to denaturation of cell products and difficulty with efficient collection of such products.

Figure 5:
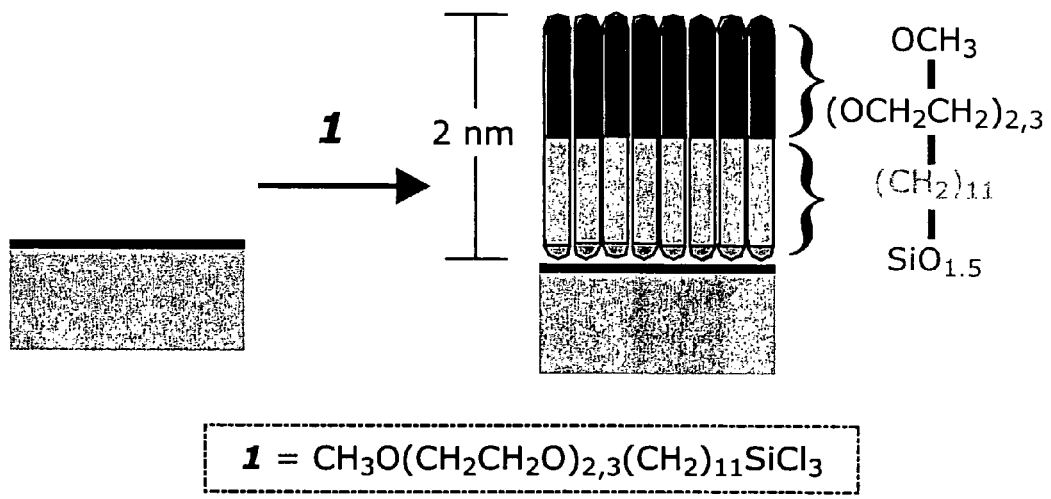
FIG. 5 shows a schematic illustration of the formation of an oligo (ethylene oxide) self-assembled monolayer on a metal oxide surface.

To alter the adsorptive properties of the contacting surfaces of the microfermentor and any connecting microchannelled networks toward the various biological components of the system a number of different approaches may be employed. In certain embodiments of the invention the surfaces are coated with a polymer. In certain embodiments of the invention the surfaces are derivatized with self-assembling molecular films prepared from $CH_3O(CH_2CH_2O)_n(CH_2)_{11}SiCl_3$ (n=2-4) (as described in 14). These reagents produce an oriented chemisorbed monomolecular film on the surfaces of metal oxides. These films are densely packed and expose oligo(ethylene oxide) units at the surface that provide a moderately hydrophilic interface with a low interfacial energy with water. See FIG. 5. A notable feature of these films is that they are able to retard the non-specific adsorption of proteins (such as insulin, albumin, lysozyme and others) and oligonucleotides, and to greatly diminish the adsorption of cells.

Figure 6:
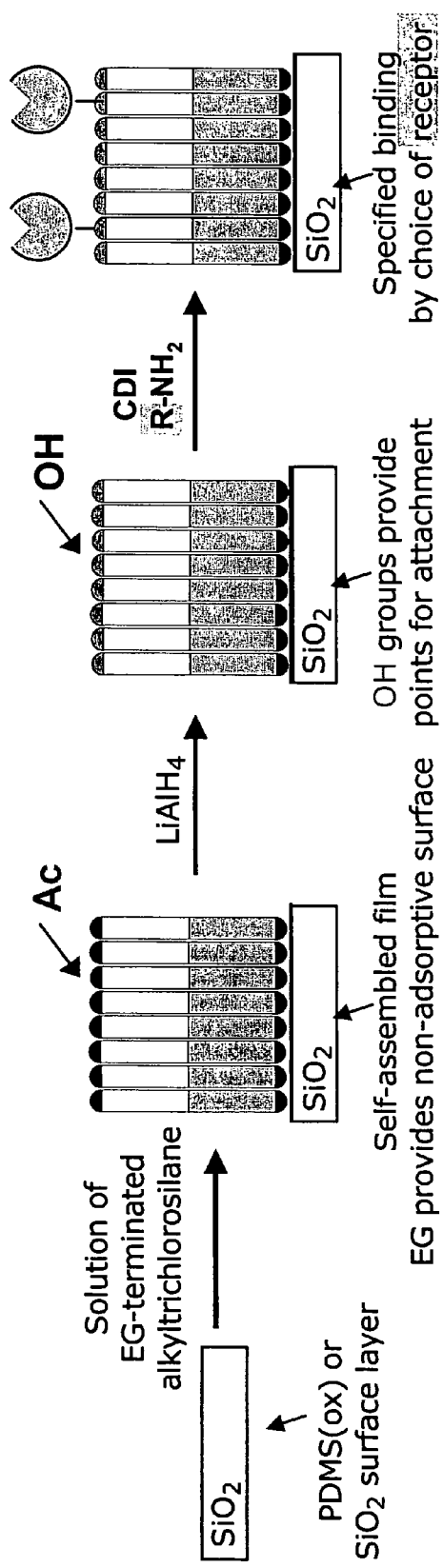
FIG. 6 shows a strategy for generating a self-assembled film incorporating a recognition element.

Further reductions in the adsorptive properties of cells may be achieved by the generation of more hydrophilic surfaces (i.e., surfaces with an even lower interfacial energy with water) and a greater entropic contribution against adsorption. Strategies for the production of such surfaces include the use of an acetate-terminated oligo(ethylene oxide) silanating reagent that is then deprotected on the surface to reveal hydroxyl groups or the use of reagents with longer oligo (ethylene oxide) chains. For example, the reagent $CH_3CO_2(CH_2H_2O)_3(CH_2)_{11}SiCl_3$ assembles to form an acetate-protected oligo(ethylene glycol) surface which, upon deprotection with $LiAlH_4$ produces a glycol termination. This surface presents a lower interfacial energy with water, decreases unwanted non-specific adsorption events, and offers a reactive alcohol terminus that inventors have employed to immobilize a protein through coupling using carbonyl diimidazole. See FIG. 6.

A complementary strategy for derivatizing the surfaces is the reaction between Grignard reagents (RMgBr) and a hydrogen-terminated silicon surface (15,16). The latter is readily formed by treating a silicon surface with hydrofluoric acid. This reaction produces grafted organic chains that are connected to the surface by robust silicon-carbon bonds. This strategy offers a compatibility with basic solutions and a broader set of processing steps than do the use of silanating reagents. According to certain embodiments of the invention in which such films are employed, some amount of surface functionalization is performed during the fabrication process (particularly prior to wafer bonding steps), thereby providing possibilities for generating patterned surfaces within chips. Further, this reaction works well with porous silicon supports and offers the possibility for modifying high surface area regions within a system (9), offering a means to tailor the properties of gas-liquid interfaces used for aeration.

According to certain embodiments of the invention a surface-initiated polymerization process using ring-opening metathesis polymerization (ROMP) is used as a means to produce thicker grafted films onto surfaces (17) and to incorporate functional groups into the films. These films form at room temperature and have thicknesses that can range from 10 to 100 nm, depending on the reaction time. Briefly, the inventors used norbornenetrichlorosilane (NTCS) to assemble a monolayer coating on an oxide surface. Exposure of this primer layer sequentially to a catalyst solution and then a monomer solution resulted in formation of adherent polymer films with thicknesses of tens of nanometers. By employing NTCS as monomer in this polymerization reaction, polymeric films containing reactive functional groups were generated. The side chain trichlorosilane groups have been reacted with poly(ethylene glycol)s (PEG) to generate grafted chains of this polymer on various oxide supports. For example, in one embodiment of the invention films were treated with a 300 molecular weight PEG and then with ethylene glycol. Variants and derivatives of PEG may also be used. According to certain embodiments of the invention methoxy-capped PEGs are used.

Figure 7:
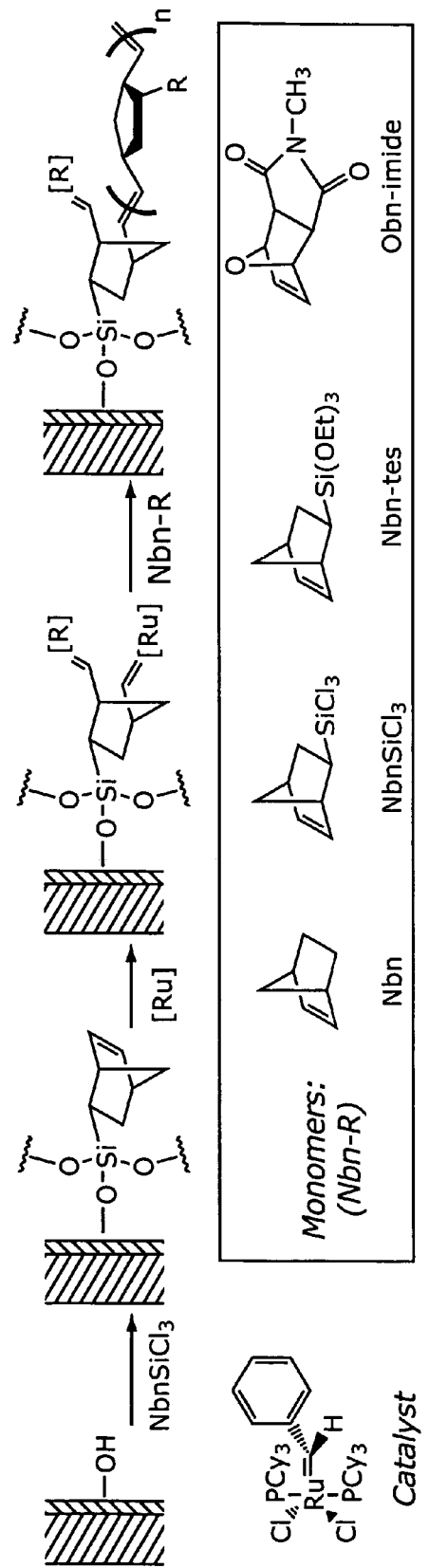
FIG. 7 shows a schematic illustration of a surface-initiated ring-opening metathesis polymerization from a hydrated metal oxide surface.

The fact that ROMP chemistry allows a wide range of functionalities to be introduced into the films offers a synthetic flexibility and ease for accessing a broader range of surfaces, and an ability to introduce various amino acids or sugars as components within the coatings. In certain embodiments of the invention this chemistry is used to fabricate more robust coatings on the microfermentor and/or channel inner surfaces and to introduce and control a range of interfacial properties. FIG. 7 shows a schematic illustration of a surface initiated ROMP from a hydrated metal oxide surface. The surface is first derivatized to expose norbornenyl groups then treated to immobilize the [Ru] catalyst. When this surface is treated with a monomer solution, a ROMP polymer grows as a grafted film from the substrate.

According to another approach, polymers such as comb polymers (i.e., polymers that comprise polymer side chains attached to a polymer backbone) are allowed to adsorb to the surface or otherwise applied to the surface. In certain preferred embodiments of the invention the backbone of the comb polymer is selected to adsorb to the surface to be coated, and the side chains are selected to retard the adsorption of proteins and/or cells. Appropriate selection of the backbone polymer will, in general, thus depend on the particular surface to be coated. For example, in certain embodiments of the invention in which the surface is glass, variants of a polymer that includes poly(acrylic acid) as a backbone are prepared and grafted with chains of either homogenous PEG or a polymer such as poly(ethylene glycol-r-propylene glycol), containing a heterogenous mixture of molecules. The side chains may thus be identical or nonidentical.

Figure 22:
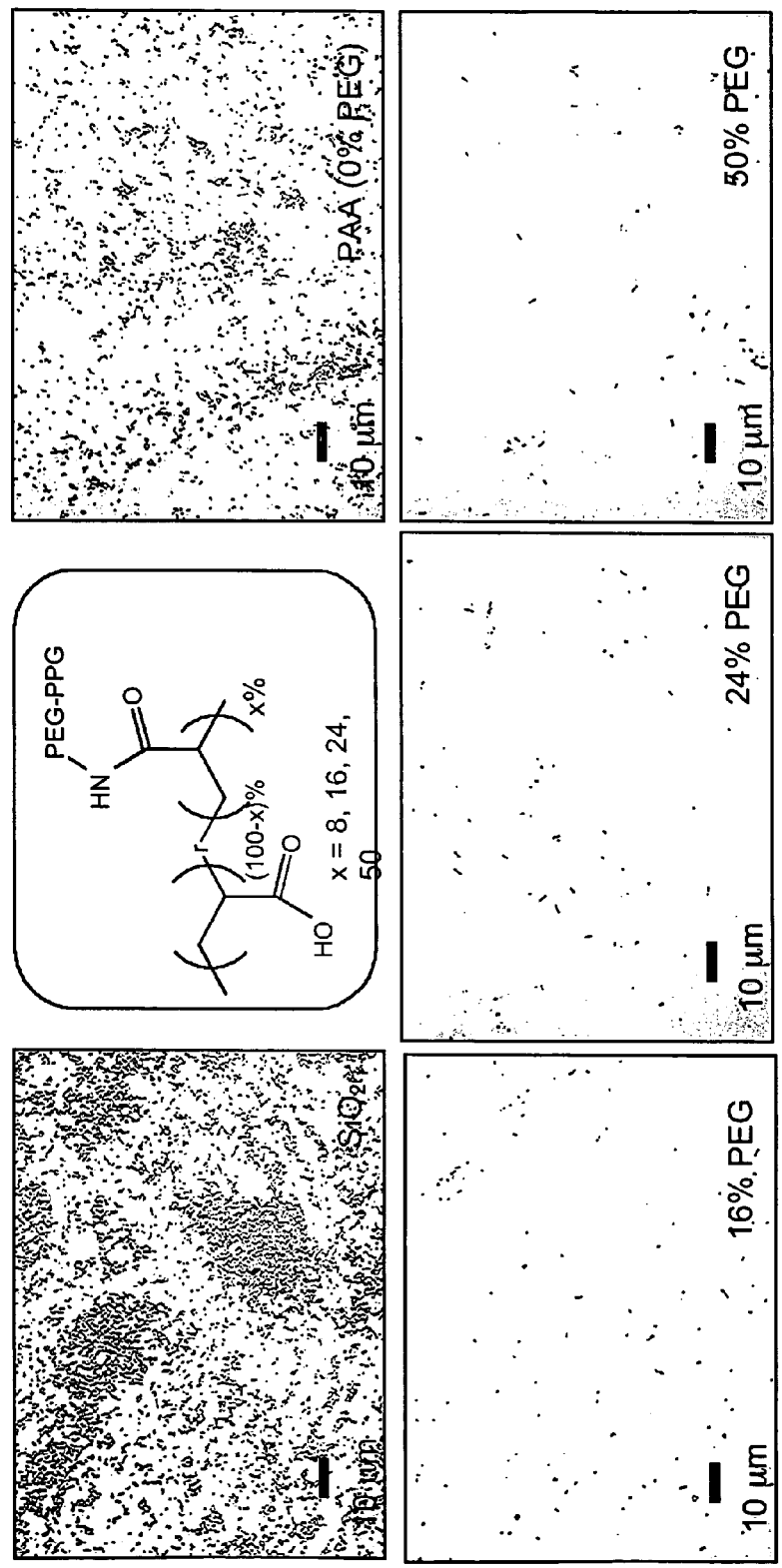
FIG. 22 shows images of cells exposed either to an uncoated glass surface or to glass surfaces that were coated with various comb polymers. The central panel in the upper portion of the figure shows the molecular formula of the polymers.

FIG. 22 shows the striking differences in cell behavior when E. coli were exposed to a bare glass surface (upper left panel) as compared with cell behavior when exposed to glass surfaces that had been treated with comb polymers having a poly(acrylic acid) backbone and a range of different PEG contents as indicated (0%, 16%, 24%, 50%). Cells were cultured in bench-scale bioreactors for 3 days in the presence of uncoated glass surfaces and glass surfaces that were coated with the various comb polymers. As is evident from FIG. 22, the presence of the comb polymers greatly decreased cell adsorption. The molecular formula of the comb polymers is presented in the upper center of the figure. The percentage number corresponds to the percent of $CO_2H$ groups (on average) on the poly(acrylic) acid backbone that contained the PEG-PPG graft. For example, if the poly(acrylic acid) molecule comprised 100 monomer units of acrylic acid in its structure, 16% indicates that each polymer molecule contains (on average) 16 $CO_2H$ groups with amide links to a PEG-PPG polymer chain and 84 free underivatized $CO_2H$ groups.

The inventors have recognized that an advantage of using these various chemical processes for tailoring the coatings on the inner surfaces is that they can be formed on the fabricated systems by simply flowing a solution of the required species through or over the device. Control over the fluidics can allow different devices (or portions of a device) to express different surface chemistries. For example, it may be desired to produce distinct regions that have a low interfacial energy with air (such as for aeration operations), that have a low interfacial energy with water (where protein and cellular adsorption is to be minimized), and that provide immobilized recognition elements for the directed adsorption of certain species (such as for sensing operations).

Self-assembly provides a powerful strategy for controlling and monitoring operations within microfabricated devices. Differences in surface reactivity (for metals vs. oxides vs. for silicon) and the abilities to direct the fluidic movements of reactants to specific regions of a device provide the ability to generate the complex patterns and progressions of surface chemistry within these microscale bioreactors for achieving the desired biochemical operation.

In contrast to bacterial cells, in the case of certain mammalian cells adhesion to a substrate promotes cell growth and may even be essential. Thus in those embodiments of the invention optimized for growth of mammalian cells, surface modifications to promote cell adhesion may be employed. In certain embodiments of the invention some surfaces or portions of surfaces are modified so as to reduce adhesion of cells, proteins, etc., while other portions are modified so as to increase adhesion. U.S. Pat. No. 6,197,575 describes various surface modifications that may be used to promote or inhibit the attachment of cells, proteins, etc., and also contains descriptions of various manufacturing techniques.

A variety of other approaches to modification of surfaces may be employed. For example, two or three dimensional stamping or contact printing may be used instead of or in conjunction with the methods described above. (See, e.g., U.S. Pat. No. 5,512,131, WO 96/29629, 6,180,239, 5,776, 748). Alternatively, chemical vapor deposition, may be employed. Chemical vapor deposition allows the formation of films in the gas phase and is applicable to three dimensional devices. Among other advantages, it permits deposition of films in cavities. See, e.g., (79) and U.S. Ser. No. 09/912,166 describing chemical vapor deposition of various polymer materials (e.g., paracyclophanes) onto a variety of substrates including polyethylene, silicon, gold, stainless steel, and glass. The polymer may be a reactive polymer and/or a functionalized polymer. In certain embodiments of the invention a surface of the microfermentor vessel and/or channel(s) is coated with a polymeric material, which may incorporate a ligand. The ligand may promote or inhibit the adhesion of cells or molecules.

IV. Sensor Technology

Research in the field of bioprocess monitoring frequently aims at the rapid acquisition of accurate analytical information that can be utilized to optimize cultivation conditions, cultivation times, and product harvesting times, in order to reduce the cost and time required to establish the process. In addition, as most modern industrial bioprocesses are microbial batch or continuous-fed batch cultivations, where control of parameters is required to maintain an optimized process, on-line monitoring of the process is highly desirable. In order to optimize bioprocesses and to perform optimized bioprocesses it is desirable to be able to monitor a variety of parameters including, but not limited to, biomass and environmental variables (e.g., pH, oxygen concentration, metabolite concentration) during the course of a fermentation, for example to allow selection of fermentation conditions that maximize yield of a desired product. With conventional fermentors, this can be achieved either by in situ monitoring of the fermentor or by removing (continuously or at frequent time points) sterile samples of the contents and subjecting them to analysis.

In order to gain direct information about the concentration of single compounds in media that usually contain a complex mixture of components, analytical devices that exhibit high-selectivity for target molecules are typically required. To date, this has only been achieved by the employment of various on-line chromatographic procedures, such as liquid chromatography, gas chromatography, and mass spectrometry, and has allowed the simultaneous detection of several compounds. These types of processes, however, require expensive multi-channel devices that can take from 30-60 minutes to analyze a particular set of compounds.

In preferred embodiments of the invention at least one analytical sensor is integrated into the microfermentor. An integrated analytical sensor is a sensor that allows monitoring (which may include detection and/or measurement) of a variable of interest (e.g., an analyte) within the microfermentor vessel without the need to remove a sample of the vessel contents. The parameter of interest may be, but is not limited to: biomass, pH, dissolved oxygen, dissolved carbon dioxide, glucose, lactate, ammonia, ions such as phosphate or metal ions, any cell metabolite (which may be a protein, nucleic acid, carbohydrate, lipid, etc.), temperature. In certain embodiments of the invention the analytical sensor detects and/or measures a cell product that is to be harvested from the microfermentor or a compound that is being removed or metabolized by the cells. In certain embodiments of the invention the analytical sensor detects and/or measures a cell product that is a byproduct of metabolism, e.g., a toxic or growth-inhibitory byproduct.

In certain preferred embodiments of the invention one or more optical sensors is employed. Optical sensors have several advantages over other sensor families. They are largely immune to electromagnetic interference and cross-talk, are non-invasive, fast and work at high temperature, and are capable of continuous monitoring of an analyte even in rugged conditions such as human blood serum and fermentation broths. In addition, another desirable feature of optical sensing (e.g., using optical chemical sensors) is that it generally does not interfere with the process being measured. Furthermore, the materials are usually inexpensive, allowing their incorporation into disposable microfermentors.

In general, an optical sensor is a device that works by detecting, e.g., measuring, induced changes (i.e., changes induced by the presence of an analyte) in the absorptive, luminescent, or fluorescent properties of a medium (the chemical sensor). Generally a system employing an optical sensor includes a light source (i.e., a source of optical excitation) and a means of detecting light. Optical excitation emitted from the source excites an optical chemical sensor, which then emits luminescence or absorbs light. The luminescence emitted from the chemical sensor or the amount of light absorbed by the chemical sensor varies depending upon the concentration of the analyte. Changes in the amount of light emitted or absorbed (measured by the detector) reflect alterations in the concentration of the analyte. The chemical sensor may be supplied in any of a number of different ways. For example, in certain embodiments of the invention the chemical sensor is present in or added to the culture medium. In certain embodiments of the invention the chemical sensor is provided as a component of a sol-gel or polymer matrix or a film, which may coat at least a portion of a vessel wall or may form a structural component of the microfermentor. See, e.g., (67).

Appropriate light sources include, among others, light emitting diodes, lasers, incandescent or fluorescent lights, glow discharge, etc. Appropriate means of detecting light include spectrometers, photodetectors, charge coupled devices, diode arrays, photomultiplier tubes, etc. Optical sensing systems may also include means for collecting light and/or for transmitting it from the source or to the detector, etc. In addition, such systems may include appropriately positioned filters to filter either excitation light or emitted light. In certain embodiments of the invention fiber-optic devices are employed to transmit the light from a source and/or to a detection means. The term "fiber-optic" refers to the medium and the technology associated with the transmission of information as light impulses along a glass or plastic wire or fiber.

In addition to, or instead of, optical sensing systems, any of a wide variety of other technology platforms may be employed. Thus in certain embodiments of the invention chemical or electrochemical sensing systems can be used in conjunction with and/or integrated into the microfermentor. For example, the inventors have shown that infrared photoacoustic spectroscopy scales favorably with miniaturization and can be used as sensitive tool for a wide range of infrared active gases, including $CO_2$ (11).

A. Oxygen Sensing

1. Integrated Oxygen Sensor

In certain embodiments of the invention the microfermentor system includes means of monitoring dissolved oxygen (DO) within the vessel. In certain preferred embodiments of the invention an oxygen sensing means is integrated within a structural component of the microfermentor, e.g., within a microfermentor wall (i.e., not separable from the structural component without disrupting the structural integrity of the microfermentor). In certain preferred embodiments of the invention the oxygen sensing means includes an optical sensor. As described in more detail in Example 4 and in (23), oxygen can be detected via fluorescence techniques that exploit the quenching produced by oxygen on fluorophores. Suitable compounds include Ruthenium II tris(4,7-diphenyl-1,1-phenanthroline)$^{2+}$. Its fluorescence is quenched in the presence of oxygen, and the relation between dissolved oxygen and fluorescence intensity has been shown to be nearly linear (33). In addition, this compound is sterilizable (34) and has been incorporated into both polymer (34) and sol-gel matrices (35). Such features are desirable for a fluorophore to be used in an optical sensor. Of course any of a number of other oxygen-sensitive compounds may be used. According to certain embodiments of the invention such a compound is incorporated into a structural component of the microfermentor, e.g., into an optically transparent bottom, top, or side wall. For example, as described in more detail in Example 4, the compound may be incorporated into a sol-gel that is applied to a structural component of the microfermentor (in this case a glass slide that forms the microfermentor base). Alternately, the compound may be applied to the bottom, top, and/or one or more sides of the microfermentor interior with or without a support and may be immobilized at this location. The compound may also be incorporated directly into the material from which the structural component is fabricated.

B. pH and Analyte Monitoring

In certain embodiments of the invention the microfermentor system includes means of monitoring the pH of the contents of the microfermentor. In certain embodiments of the invention the microfermentor system includes means of monitoring the presence of one or more analytes in addition to or instead of oxygen. Methods employed in the context of commercially available blood gas (pH, $CO_2$, $O_2$) sensors may be adapted for use in the microfermentor. In such sensors pH is detected by a chromophore, which changes its optical spectrum as a function of the pH. Absorption- and fluorescence-based fiber-optic sensors may be used. Carbon dioxide is detected indirectly, since its diffusion in a carbonate solution fixed on the fiber tip alters the pH, so that the carbon dioxide content can be measured by measuring the pH.

Hydrogels, cross-linked networks of hydrophilic polymers, can also be used for pH sensing. These hydrogels swell in the presence of water, and various hydrogels have been synthesized that undergo large changes in their swelling ratio depending on their environment. In addition to pH, responsive hydrogels have been developed that sense various other environmental conditions including temperature, light, electric field, pressure, the presence of carbohydrates, and the presence of antigens. pH-dependent swelling is achieved through the incorporation of weakly basic or acidic groups on the polymer backbone.

Two effects allow the quantification of variable pH-responsive hydrogel swelling. The first effect is the change in optical properties of the hydrogel on swelling. For this purpose a hydrogel membrane, containing embedded microspheres 1 µm in diameter, is synthesized. The membrane is turbid because of the difference in refractive indices between the hydrogel and the microspheres. The turbidity of the membrane decreases in an acidic medium due to the swelling of the microspheres, which lowers their refractive index and brings it closer to that of the hydrogel. The change in turbidity can be detected optically (47).

A second method of quantification involves measuring changes in the hydrogel conductivity. Conductivity changes have been found to reflect differences in ionic mobility within the hydrated gel (48, 49). This effect has been used to microfabricate a conductimetric pH sensor (50, 51). Changes in sensor resistance as large as 45% per pH unit near physiological pH have been reported. Because the sensor operation is based on changes in ion mobility, it operates best in solutions of high ionic strength.

Numerous other methods for performing sensing, e.g., optical sensing, of various analytes are known in the art. See, for example, U.S.S.N. 20020025547; 6,377,721; 6,285,807, and references therein. Other approaches to the use of fiber-optic devices and/or optical chemical sensors are found, for example, in (36-39 and 83) and references therein, all of which are herein incorporated by reference.

C. Temperature Sensing

In certain embodiments of the invention temperature control is achieved by incorporating temperature sensors and resistance heaters into the design as described, for example, in (9). As described therein, the inventors have shown in the context of a micromechanical system that it is possible to heat reaction volumes uniformly while accurately monitoring the temperature. Methods of monitoring temperature using optical chemical sensors are known in the art.

D. Monitoring Biomass

A number of techniques may be employed to detect and quantify biomass (e.g., cell density). In certain embodiments of the invention biomass is monitored using optical density. Sensing of optical density can be carried out using absorbance measurements at 600 nm, as is currently done in laboratory analysis. Absorbance measurements can be made through a transparent portion of the microfermentor vessel wall or using a waveguide. Example 4 describes one embodiment in which a light source provides light to one side of the microfermentor (in this case the bottom), and light transmitted through the microfermentor is captured at a different side (in this case the top). Appropriate light sources, detectors, and light transmission devices are described above. Equipment such as lenses, filters, beam splitters, dichroics, prisms and mirrors may be incorporated to enhance detection and accuracy. According to certain embodiments of the invention a cell that produces an easily monitored reporter enzyme, e.g., a fluorescent or luminescent protein such as green fluorescent protein (GFP) is employed.

The invention also encompasses the detection of cell metabolites including, among others, NAD(P)H (a pyridine nucleotide that is an endogenous chromophore and thus may serve as a fluorescence indicator), as an alternate or complementary means of monitoring biomass (52, 53).

According to certain embodiments of the invention one or more parameters or analytes is measured using Raman spectroscopy (80, 81). This technique may be particularly appropriate for measuring organic compounds, e.g., nutrients, cellular metabolites, etc.

E. Self-Assembling Sensors

On metal surfaces, self-assembly can be used to produce modified electrodes with chemical sensing abilities. For example, thiols will adsorb onto gold microelectrodes patterned on a silicon (oxide) substrate and selectively functionalize the electrodes and not the background substrate (18). The use of electroactive thiol reagents (specifically, a quinone-thiol and a ferrocene-thiol) has provided the ability to generate pH sensors from gold electrodes with a simple fabrication methodology (19). For example, during the microfermentor fabrication, various microelectrodes can be readily introduced strategically into its structure, and self-assembly can be used subsequently to functionalize their surfaces and produce on-board chemical sensors within the device. Present abilities allow the preparation of electrochemical sensors for pH, halide detection, glucose monitoring, and a few other species and can be expanded to provide local probes for other analytes of interest.

F. Enhancing Sensitivity of Sensors

The invention encompasses a variety of approaches to enhance the sensitivity of biosensors by using integrated optical components. One such approach includes the enhancement of the interaction path length for a fluorescent indicator emitting into a waveguide and the absorption path length in evanescent wave spectroscopy. This is realized by the use of planar waveguides in silicon/silicon dioxide. A second approach is to enhance the sensitivity of the fluorescence detection process by integrating silicon avalanche photodiodes with silicon dioxide waveguides. Recently, these avalanche photodiodes have enabled single molecule detection in aqueous flows (21).

1. Waveguide Sensors

Fiber optic sensors are only one implementation of what can generally be referred to as waveguide sensors. In general, these sensors rely on the refractive index difference between the waveguide core and the waveguide cladding to confine the light. The optical field, which is present very close to the core surface, is called the evanescent wave and can be used to probe the absorption of the surrounding medium or can be excited by fluorescence. If the cladding is stripped away and the waveguide immersed in a solution of fluorescent indicator, the only fluorescence excited by the light in the waveguide core would come from dye molecules in the sheath surrounding the exposed core. Some of that fluorescence would couple back into the waveguide and come out the ends.

Figure 8:
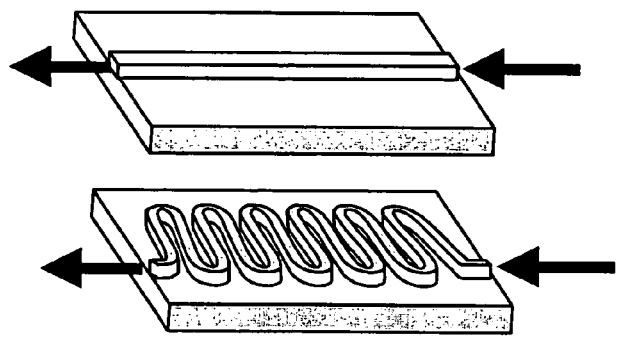
FIG. 8 shows schematics of straight (top) and serpentine (bottom) waveguides.

According to certain embodiments of the invention planar waveguides with rectangular cross-section are integrated on a microscale bioreactor platform. These devices allow for dramatic enhancements in interaction path length by virtue of the serpentine paths the waveguide can take through the analyte. For example, a serpentine waveguide can compress a 1 meter optical path length on a one square centimeter surface area (see FIG. 8). More importantly the total volume of this waveguide can be smaller than one nanoliter. As such, the planar waveguide can realize macroscopic optical cross-sections through microscopic analyte volumes. In certain embodiments of the invention the microscale bioreactor incorporating a waveguide sensor has an interior volume of less than or equal to 1 ml. In certain embodiments of the invention the microscale bioreactor incorporating a waveguide sensor has an interior volume of less than 200 µl. In certain preferred embodiments of the invention the working volume is between 50 µl and 100 µl inclusive. In certain preferred embodiments of the invention the working volume is between 5 µl and 50 µl, inclusive. In certain preferred embodiments of the invention the working volume is between 5 µl and 10 µl, inclusive. In certain preferred embodiments of the invention the working volume is approximately 7.5 µl or approximately 10 µl. In certain preferred embodiments of the invention the working volume is approximately 5 µl. Waveguide sensors may be fabricated using any appropriate technique. (See, e.g., U.S. Pat. No. 6,355,198 for some approaches.)

2. Single Photon Avalanche Diodes

The small volumes of the microscale bioreactors necessarily mean that analysis must be performed on small volumes of analyte. While the waveguide biosensor may have maximal interaction with the available analyte, in certain embodiments of the invention further sensitivity is realized by direct integration of photodetectors with the waveguides. Recent advances in single molecule detection within a flow cell have been made possible by the development of a single-photon avalanche diode (SPAD) with high quantum efficiency and low timing jitter. The increased fluorescence detection efficiency provided by the SPAD has enabled the detection of single chromophore molecules (23).

Silicon avalanche photodiodes with 90% quantum efficiency for wavelengths from 400-800 nm are commercially available. These devices have an internal electrical gain of 40-100 due to the avalanche process and exhibit very low noise as well as high dynamic range. Microfabricated SPAD can be easily integrated with waveguide biosensors. In this way fluorescence can be monitored from even a small number of molecules for virtually all visible and near-infrared markers used in biochemistry.

3. Optical Background in Bioreactors

A significant obstacle to coupling an optical sensor to the fermentation process is interference from the medium broth. This is due to the content of the fermentation broth, which contains cells and other opaque components. These materials absorb and scatter light, which interferes with the optical signal. The invention encompasses three approaches to deal with the complexities of bioprocess monitoring.

The first is to integrate microporous filters along the sensing surface of the waveguides. Recently, waveguide based optical sensors based on immobilization of a ruthenium complex in Nafion to monitor pH in a fermentation of *Klebsiella pneumoniae* have been demonstrated. Interference from the culture medium was eliminated by the addition of a black microporous filter membrane on top of the sensing film (24). These filter membranes can either be deposited after waveguide processing or they can be directly microfabricated during the sensor process.

A second approach is to employ high speed SPAD for fluorescence-lifetime spectroscopy. It has been well documented that fluorescence-lifetime methods can be successfully applied in optical sensing. These methods have considerable advantages over intensity-based methods. The fluorescence lifetime of an indicator is an intrinsic property and is virtually independent of fluctuations in light-source intensity, detector sensitivity, light throughput of the optical system, sensing layer thickness and indicator concentration (25). This implies that, in contrast to absorption methods, no reference measurement system is necessary, and, in contrast to fluorescence-intensity measurements, no compensation for variation of instrumental parameters is necessary. Lifetime-based sensors can be stable over years without any need for recalibration (26).

G. Multiple Sensing Means

Regardless of the sensing methodology employed, in certain embodiments of the invention the microscale bioreactor incorporates multiple sensors (e.g., at least 2, 3, 4, 5, or even more), thus allowing monitoring of multiple bioprocess parameters. In certain embodiments of the invention the microfermentor incorporates a sensor for monitoring oxygen. In certain embodiments of the invention the microfermentor incorporates sensors for monitoring oxygen and at least one other analyte or parameter. In certain embodiments of the invention the microfermentor incorporates sensors for monitoring oxygen and pH. In certain embodiments of the invention the microfermentor incorporates sensors for monitoring oxygen, temperature, and at least one other analyte or parameter. The sensors may be based on the same technology platform (e.g., the sensors may all be optical chemical sensors) or may be based on different technology platforms. In certain embodiments of the invention biomass and at least one additional parameter (e.g., dissolved oxygen concentration) are monitored optically. In certain embodiments of the invention the additional parameter is monitored using an optical chemical sensor. Monitoring may take place continuously, and multiple parameters may be monitored simultaneously. Where optical sensors are used it is important to avoid confounding of sensors where possible. For example, it may be important to account for the fact that absorbance readings for optical density measurements are typically made at 600 nm.

Figure 21:
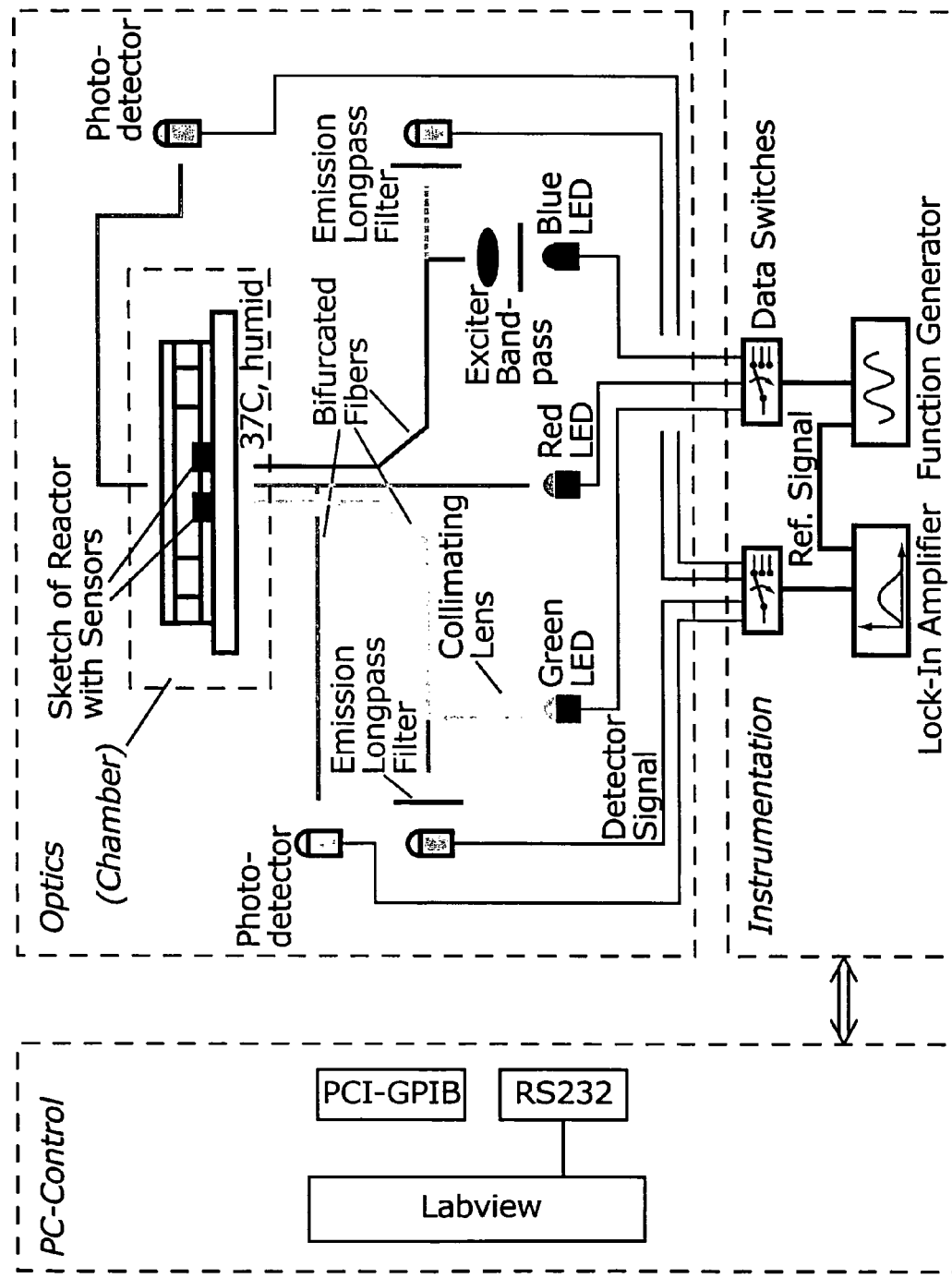
FIG. 21 shows a schematic of a microfermentor integrated with optical density, dissolved oxygen, and pH sensors together with associated instrumentation and computer software.

The information obtained by monitoring may be used to control and/or alter microfermentor conditions. Such monitoring and alteration may be controlled by appropriate software (e.g., the LabView system). In the case of a microfermentor array, each microfermentor may be monitored and controlled individually. FIG. 21 shows a schematic of a microfermentor integrated with optical density, dissolved oxygen, and pH sensors. As shown on FIG. 21, the microfermentor and associated optics interfaces with instrumentation and computer software to measure and/or control bioprocess parameters (see below).

V. Bioprocess Parameter Control

As described herein, in addition to monitoring of bioprocess parameters, in certain embodiments of the invention one or more of these parameters may be actively controlled and/or varied. A. Gas Exchange In certain embodiments of the invention oxygen delivery and/or removal of waste gases such as carbon dioxide is accomplished via a gas-permeable membrane. Preferably such a membrane is relatively impermeable to the components of the culture medium. In general, two categories of membranes that are typically used to aerate cultures open-pore membranes (e.g. polypropylene (PP) and polytetrafluoroethylene (PTFE)), and diffusion membranes (e.g. PDMS), may be used to aerate the microfermentor.

Porous membranes consist of a polymeric matrix that contains pores from 2 nm to 10 μm in diameter. Many pore geometries exist, and together with the wide range of pore sizes give rise to several different regimes of $O_2$ transport, including Knudsen diffusion (narrow pores) and viscous flow (wide pores) (59). Mass transfer through a diffusion membrane (which contains molecular pores) is a function of a thermodynamic parameter, the solubility S, and a kinetic parameter, the diffusivity D. Which of these parameters dominates the mass transfer for a given polymer and penetrant depends on the nature of the interaction between the two.

Suitable materials for membranes include, for example, fluoropolymers such as the microporous membranes Teflon (e.g., Teflon AF 2400, DuPont), Goretex, cellulose acetate, porous glasses (e.g., Vycor), microporous ceramic membranes (e.g., made by sol-gel techniques), zeolite membranes, and silicones such as the diffusion membrane PDMS. Relevant permeability, solubility, and diffusivity parameters of PDMS and Teflon AF2400 are presented in Tables 1, 2, and 3 (data from 60-66).

TABLE 1

Summary of Gas Permeability, Solubility, and Diffusivity Parameters in PDMS at 35° C.

| Penetrant | $P \times 10^{10}$ [$cm^3$(STP) · cm/$cm^2$ · s · cmHg)] | S [$cm^3$(STP)/ $cm^3$polymer · atm] | $D \times 10^5$ [$cm^2$/s] |
|---|---|---|---|
| $O_2$ | 800-933 | 0.18 | 3.4 |
| $CO_2$ | 3800-4570 | 1.29-1.31 | 2.2-2.64 |

TABLE 2

Summary of Water Permeability, Solubility, and Diffusivity Parameters in PDMS at 300 K.

| Penetrant | $P_l \times 10^9$ [$cm^2$/s] | $P_g \times 10^5$ [$cm^2$/s] | $S_l \times 10^3$ | $S_g$ | $D \times 10^5$ [$cm^2$/s] |
|---|---|---|---|---|---|
| $H_2O$ | 4.2-10.0 | 9.1 | 0.276-1.0 | 5.9 | 1.53-2.0 |

TABLE 3

Summary of Gas Permeability in Teflon AF 2400 at 25° C.

| Penetrant | $P \times 10^{10}$ [$cm^3$(STP) · cm/$cm^2$ · s · cmHg)] |
|---|---|
| $O_2$ | 1600 |
| $CO_2$ | 3900 |

In Table 2, the solubility S is defined as the ratio of the number densities between two phases and is used to calculate the concentration at the polymer interface given the concentration in the bulk solution on both sides of the membrane. The permeability P then has units of diffusivity D, and can be thought of as an "adjusted" diffusivity. This is in contrast to the units that are normally given to permeability (Table 1), arising from the relations:

$$P = DS$$

and $$N = \frac{D}{t}(C_1 - C_2)$$

where N is the penetrant flux through the membrane. One of ordinary skill in the art will be able to select membrane materials having appropriate diffusivities and solubilities for water, oxygen, carbon dioxide, and other penetrants.

Preferred materials are biocompatible, relatively strong, and capable of being formed into thin membranes (e.g., membranes with thicknesses on the order of the dimensions of the microfermentor. The external face of the membrane (i.e., the face not in contact with the contents of the microfermentor) is in contact with a source of oxygen that has a higher oxygen concentration than the concentration of oxygen in the microfermentor culture vessel. This oxygen source may be a gas or a liquid. In certain embodiments of the invention the source is a gas with a higher oxygen content than air. Oxygen diffuses across the membrane to provide oxygenation for the cells within the microfermentor. In certain embodiments of the invention two or more separate membranes are incorporated into the microfermentor. The external surface of the second membrane may be in contact with a gas or liquid having a lower oxygen content than the contents of the microfermentor vessel. In this manner an oxygen gradient is established across the microfermentor vessel, which facilitates oxygenation. By varying the relative oxygen concentrations with which the external faces of the membranes are in contact, it is possible to control the oxygen concentration within the microfermentor.

Although aeration membrane(s) are employed in preferred embodiments of the microfermentor system, the invention also encompasses the use of other means of providing oxygen, e.g., miniaturized magnetic stirrers, bubbling action of aeration, piezoelectric vibration, or chemical production of oxygen (in which case it is desirable to avoid the formation of toxic byproducts).

In preferred embodiments of the invention sufficient oxygen is provided to the interior of the microfermentor to support the viability and growth of bacterial cells undergoing aerobic metabolism at cell densities comparable to those employed in standard fermentation processes (e.g., approximately $10^{12}$ cells/liter). In certain embodiments of the invention sufficient oxygen is provided to support exponential growth of bacterial cells undergoing aerobic metabolism at a range of cell concentrations, e.g., at up to approximately $10^6$ cells/l, up to approximately $10^7$ cells/l, up to approximately $10^8$ cells/l, up to approximately $10^9$ cells/l, up to approximately $10^{10}$ cells/l, up to approximately $10^{11}$ cells/l, up to approximately $10^{12}$ cells/l, or up to approximately $10^{13}$ cells/l. As is well known in the art, mammalian cells typically have a lower oxygen uptake rate than aerobic bacteria.

B. Climate Control

1. Temperature Control

Figure 9:
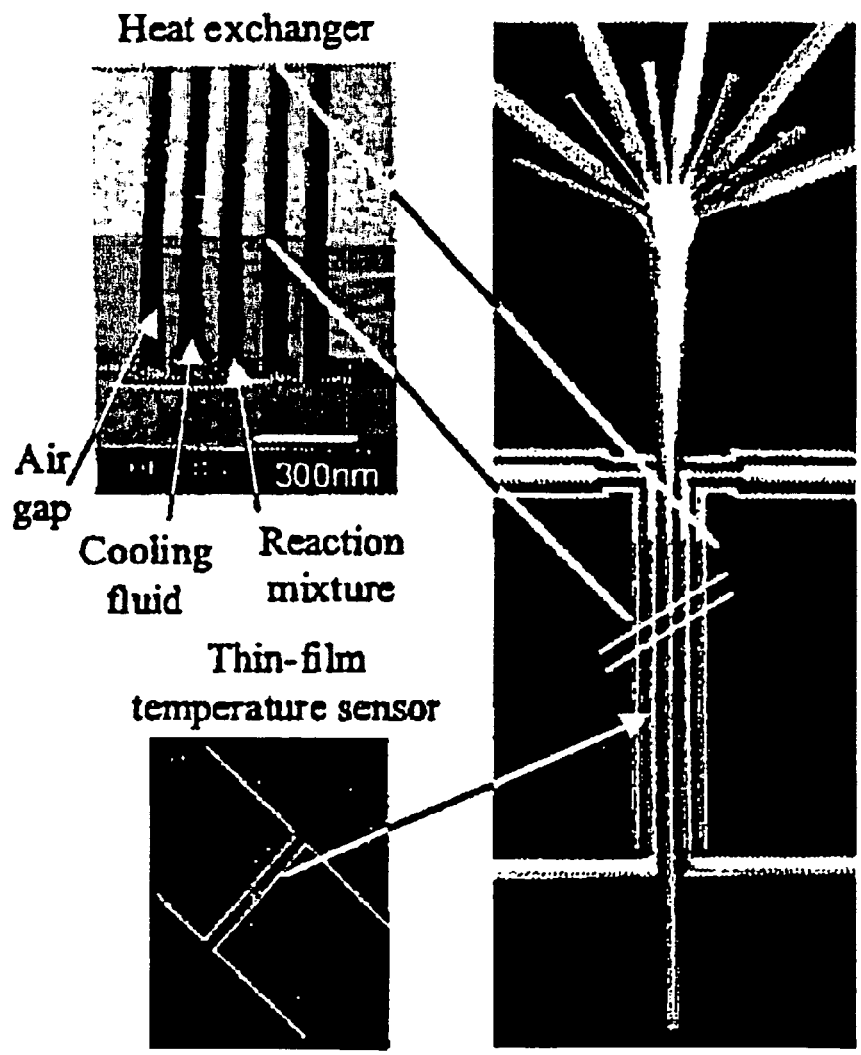
FIG. 9 shows an example of a microfabricated heat exchanger.

As mentioned above, in certain embodiments of the invention temperature control is achieved by incorporating temperature sensors and resistance heaters into the design of the microfermentor. For example, the inventors have shown in the context of a micromechanical system that it is possible to heat reaction volumes uniformly while accurately monitoring the temperature (9). In addition, in certain embodiments of the invention heat exchangers for heating and cooling are incorporated into the microfermentor in a fashion analogous to that described in (10). An example of a microfabricated heat exchanger is shown in FIG. 9. The excellent heat transfer characteristics of small dimension microfabricated devices provide good thermal uniformity and small time constants. In certain embodiments of the invention the temperature is controlled to within ±2° C. In certain embodiments of the invention the temperature is controlled to within ±1° C. In certain embodiments of the invention the temperature is controlled to within ±0.1° C.

In certain embodiments of the invention temperature control is achieved by placing the microfermentor in a temperature-controlled environment, for example by placing the microfermentor in a temperature-controlled incubator or chamber as described in Example 3. Temperature control can be achieved, for example, by flowing water of a desired temperature through a chamber base.

2. Evaporation Control

In certain embodiments of the invention an appropriate humidity is maintained by placing the microfermentor in a humidity-controlled environment. For example, as described in Example 3, the microfermentor may be placed in a chamber that contains open reservoirs of water. Alternatively, humidified air may be flowed through the chamber. In preferred embodiments of the invention the chamber is sealed. Sealing the channels that lead into the microfermentor also minimizes evaporation. In addition, appropriate selection of materials for the structural components of the microfermentor (e.g., selection of hydrophobic materials) reduces evaporation.

In certain embodiments of the invention one or more membranes, one side of which in contact with the interior of the microfermentor vessel and the other side of which is in contact with humidified air or water, compensates at least in part for evaporative losses. The humidified air or water may be flowed past the membrane. As described above, various designs incorporating two vessels separated by a gas-permeable membrane may be employed.

C. pH Control

In large part because protein configuration and activity are pH dependent, cellular transport processes, reactions, and hence growth rates depend on pH. Factors such as ongoing metabolic activity may alter the pH in a culture medium. Therefore, certain embodiments of the invention include a means to control the pH. In certain embodiments of the invention pH control is achieved by providing a suitable buffer. The buffer may be provided within the culture medium. Alternately, an external buffer source may be employed, in which case the invention includes a contact between the external buffer source and the interior of the microfermentor vessel. For many bacteria, growth rates typically reach a maximum in the pH range of 6.5-7.5 (55). Typically, negligible growth occurs at a pH 1.5 to 2.0 pH units above or below the optimal pH. Many eukaryotic cells are even more sensitive to changes in pH. Accordingly, in certain embodiments of the invention the microfermentor system includes a means of controlling the pH within ±0.1 pH units of an optimum pH for cell growth. In certain embodiments of the invention the microfermentor system includes a means of controlling the pH within ±0.2 pH units of an optimum pH for cell growth. In certain embodiments of the invention the microfermentor system includes a means of controlling the pH within ±0.5 pH units of an optimum pH for cell growth. In certain embodiments of the invention the microfermentor system includes a means of controlling the pH within ±1 pH units of an optimum pH for cell growth. In certain embodiments of the invention the microfermentor system includes a means of controlling the pH within ±1.5 pH units of an optimum pH for cell growth. In certain embodiments of the invention the microfermentor system includes a means of controlling the pH within ±2 pH units of an optimum pH for cell growth. One of ordinary skill in the art will readily be able to determine the optimum pH for cell growth by reference to the scientific literature and/or by systematically culturing cells under conditions of varying pH while holding other parameters constant. The optimum pH may vary depending upon other culture parameters, e.g., nutrient supply, temperature, etc.

D. Nutrient Control

According to certain embodiments of the invention addition of nutrients, stimulants, buffers, etc., is achieved through the use of external pressure driven flows, e.g., created by pumps such as syringe pumps. See also (40) and references therein. When possible, active fluid control elements may be used. Development of such elements, e.g., valves, is currently under way in the microelectromechanical systems community and will readily be applicable in the context of the microfermentors described herein.

Alternatively, nutrients may be provided by diffusion through a membrane, e.g., from a larger reservoir, so that components are constantly renewed. Certain of the two-vessel designs described above allow for this feature.

E. Agitation

In certain embodiments of the invention agitation is used to assist in keeping the cells in suspension and prevent them from settling on the bottom of the microfermentor. Liquid within the microfermentor may be agitated by attaching the microfermentor to a moving surface (as is the case with shake flask agitation). Alternative methods of agitation may also be employed, e.g., piezoelectric effects, stirring with magnetic beads, etc.

F. Bioprocess Control in Microfermentor Arrays

The invention provides microfermentor systems comprising a plurality of microfermentors in which one or more bioprocess parameters is controlled. An exemplary embodiment is depicted in FIG. 4B. According to certain embodiments of the invention the system comprises individually addressable wells, whereby each well may receive a unique combination of inputs. According to certain embodiments of the invention each well receives the same input along one dimension and a different input along a second dimension of the array. This approach is not limited to two dimensions; rather any number of different inputs may be provided. According to certain embodiments of the invention the microfermentors are accessed by microfluidic channels. The wells may be housed in a plate or platform comprising multiple layers, one or more of which may contain channels that connect to the wells. The wells may also be addressed electronically, e.g., via wires extending therefrom. Electronic addressing may be used to control components within the wells. For example, electronic addressing may be used to control resistors within the wells to regulate temperature. In addition, data may be gathered from each well independently.

VI. Methods of Using Microfermentors and Microfermentor Arrays

A. Introduction

Fermentations are important sources of biological products used in the pharmaceutical, food, and chemical industries (54, 68-73). These products include primary and secondary metabolites, enzymes, recombinant proteins, vaccines, and the cells themselves (e.g., yeast). A hallmark of commercial fermentation processes (e.g., processes performed in production scale fermentors, by which is meant fermentors with working volumes of between 10 and 300,000 liters) has been an attempt to promote enhanced production of these industrial products through improvement of strains and/or optimization of fermentation conditions.

Strain improvement has typically been achieved through one of several procedures (mutation, genetic recombination, and genetic engineering), all of which bring about changes in the DNA sequence. These techniques are frequently used in combination with each other to reach the desired goal. Currently, improved strains are selected using an iterative cycle of three basic principles: mutation, screening, and assay. Manual screening operations are typically carried out in shake flasks or test tubes. Mutants are cultured in a primary screen, and hits are identified by measuring the total product yield using an assay such as thin layer chromatography (TLC), high-performance liquid chromatography (HPLC), or the increasingly popular enzyme-linked immunosorbent assay (ELISA). Identified hits are then taken forward and run through additional screens for confirmation.

Additionally, fermentation and cell culture can play a critical role in the elucidation of gene function in other organisms. The most common method involves the cloning and expression of a genome in a suitable host, such as *E. coli* or yeast, followed by fermentation in a bioreactor. The fermentation allows the identification of conditions that regulate gene expression, as well as production optimization of the protein that is then expressed. Complete genomic sequences are currently available for a wide variety of organisms including bacteria, fungi, and plants, and the amount of genomic sequence data is growing rapidly. (See, e.g., sequences available at the Web site having URL www.ncbi.nlm.nih.gov/entrez/query.fcgi?db=Genome) In particular, the recent completion of the human genome sequence provides an especially labour-intensive challenge in this area. The same issues that were identified above for the screening of improved strains are of concern here, and here again the opportunity exists for the miniaturization of culture conditions.

B. Cell Types

The microscale bioreactors of the invention may be used to culture and monitor cells of any type including microorganisms such as bacteria (e.g., eubacteria, archaebacteria), filamentous or non-filamentous fungi (e.g., yeast), protozoa, and also plant cells, insect cells, mammalian cells, etc. Bacteria may be aerobes, facultative anaerobes, or anaerobes and include, but are not limited to, members of the following genera: *Escherichia, Enterobacter, Streptomyces, Azotobacter, Erwinia, Bacillus, Pseudomonas, Klebsiella, Proteus, Salmonella, Serratia, Shigella, Rhizobia, Rhodococcus, Vitreoscilla,* and *Paracoccus.* (See the Web sites with URLs www.bacterio.cict.fr/eubacteria.html and www.bacterio.cict.fr/archaea.html for lists of bacteria that may be used.). Yeast include, but are not limited to, members of the genera: *Saccharomyces, Schizosaccharomyces, Moniliella, Aureobasidium, Torulopsis, Candida, Trigonopsis, Trichosporon, Torulopsis, Zygosaccharomyces,* and *Yallowia*. Insect cells, e.g., cells that support the growth of baculovirus such as *Spodoptera frugiperda* sf9 cells (see, U.S. Pat. No. 4,745,051) may be used. Such cells are particularly useful for production of recombinant proteins. Mammalian cells including, but not limited to, Chinese hamster ovary (CHO) cells, human embryonic kidney (HEK) cells, COS cells etc., may be used. See (76). In certain preferred embodiments of the methods described below the cells are of a type that is currently used in commercial bioprocesses.

The cells may be newly isolated or identified naturally occurring strains or variants, which may also be referred to as mutants. The cells may be selected, e.g., for a desirable phenotype. The cells may be genetically modified, e.g., using recombinant DNA technology. For example, cell or strain variants or mutants may be prepared by introducing appropriate nucleotide changes into the organism's DNA. The changes may include, for example, deletions, insertions, or substitutions of, nucleotides within a nucleic acid sequence of interest. The changes may also include introduction of a DNA sequence that is not naturally found in the strain or cell type. One of ordinary skill in the art will readily be able to select an appropriate method depending upon the particular cell type being modified. Methods for introducing such changes are well known in the art and include, for example, oligonucleotide-mediated mutagenesis, transposon mutagenesis, phage transduction, transformation, random mutagenesis (which may be induced by exposure to mutagenic compounds, radiation such as X-rays, UV light, etc.), PCR-mediated mutagenesis, DNA transfection, electroporation, etc.

The complete genomic sequence is available for a number of different organisms including numerous bacterial species. The availability of the genomic sequence has facilitated the construction of panels of mutants, each of which bears a loss-of-function mutation in one or more genes or open reading frames (42). In some cases the particular gene bearing the loss-of-function mutation is "tagged", making it possible to identify a particular mutant in a mixed population.

One of ordinary skill in the art will be able to select appropriate culture media and environmental conditions for any particular cell type. Parameters such as oxygen delivery, temperature, and pH, etc., may be varied as appropriate. In addition, the microfermentor properties such as surface characteristics, vessel size, etc., may be modified depending upon the features of the particular cell type to be cultured. B. Screening for Optimal Strains The microscale bioreactors of the invention may be used to identify optimal organisms for performing a bioprocess. Since the microfermentors allow multiple fermentations to be performed in parallel under similar or identical conditions, they find particular use in selecting a cell type that performs optimally under such conditions, e.g., a cell type that produces a maximum amount of a desired product, a cell type that does not require a particular nutrient, etc.). The similar or identical conditions may include, but are not limited to: growth medium (carbon source, nitrogen source, precursors, and nutrients such as vitamins and minerals, salts, etc.), temperature, pH, redox potential, agitation rate, aeration rate, ionic strength, osmotic pressure, water activity, hydrostatic pressure, dissolved oxygen or carbon dioxide concentration, concentration of inducers and repressors, etc. The microfermentors are useful in screening panels of naturally occurring strains, banks of mutants, banks of genetically modified organisms, etc. Multiple different cell types or strains may be cultured in parallel under similar or identical conditions. The same cell type may be grown at a range of different cell densities. Strains, mutants or variants of particular interest include, but are not limited to, auxotrophic strains, deregulated mutants, mutants resistant to feedback inhibition, mutants resistant to repression, etc. See (68) for further discussion.

An optimum strain may be selected based on a variety of criteria. For example, an optimum strain may be, but is not limited to: a strain that produces the greatest amount of a desired product in a given time; a strain that is able to produce a desired product using a particular starting material (e.g., an inexpensive starting material); a strain which is able to grow in medium lacking particular components; a strain that is able to tolerate buildup of toxic or inhibitory metabolites in the culture; a strain that is able to tolerate a wider range of growth conditions such as pH, oxygen concentration, etc.; a strain that is able to achieve a higher cell density, etc.

C. Optimizing Bioprocess Parameters

The microscale bioreactors of the invention are useful in identifying optimal bioprocess parameters for performing a given bioprocess. Since the microfermentors allow control and/or monitoring of multiple variables, e.g., biomass, oxygen concentration, etc., they may be used to determine what values for these variables lead to optimum production of a desired metabolite or optimum removal of an undesired compound. For example, the maximum growth rate may not be the optimal growth rate for such purposes. Growing cells at less than the maximum growth rate may help minimize the accumulation of byproducts that negatively impact the growth or metabolism of the organism.

Parameters that may be varied include, but are not limited to: growth medium (carbon/energy source (e.g., glycerol, succinate, lactate, and sugars such as, e.g., glucose, lactose, sucrose, and fructose), nitrogen source, precursors, and nutrients such as vitamins and minerals, salts, etc.), temperature, pH, redox potential, agitation rate, aeration rate, ionic strength, osmotic pressure, water activity, hydrostatic pressure, dissolved oxygen or carbon dioxide concentration, concentration of inducers and repressors, etc. Any of these parameters may be varied in different ways in individual microfermentors operating in parallel, so that a time-optimal manner of varying the parameters can be identified, e.g., a manner of varying the parameters so as to optimize the process, e.g., to maximize production of a desired metabolite or maximize removal of an undesired compound. See (68) for further discussion.

The availability of a large number of microfermentors, e.g., as a microfermentor array, makes it possible to systematically vary a single parameter across a wide range of values while holding other parameters constant. Perhaps of greater significance, the availability of a large number of microfermentors makes it possible to assess the effects of simultaneously varying multiple parameters across a range of values. Appropriate mathematical techniques (which will likely be embodied in software) may be employed to determine which of these parameters is significant in terms of effects on a desired output, e.g., product level or removal of an undesired compound from the culture medium See 68 and references therein, describing use of software packages such as JMP (SAS, Cary, N.C., USA) and use of experimental designs such as Plackett-Burman screening design, fractional factorial design, response surface methodology, Box-Wilson central composite design, etc. Multiple microfermentors may be operated under each set of bioprocess parameters, which may greatly increase the reliability and statistical significance of the data.

Once one or more cell strains and/or bioprocess parameters is selected using the microscale bioreactors, scale-up (e.g., to production scale fermentors) may be performed. In performing scale-up, the skilled artisan will take into account factors such as differences in oxygenation technique between microfermentors and production scale fermentors, different geometries, different shear stresses, etc. (See 68, 74, 75).

D. Additional Applications

The microfermentors and microfermentor arrays also find use in screening compounds to determine their effects on cells. For example, they may be used to identify compounds that inhibit or reduce the growth of cells and/or exert other deleterious effects on cells (e.g., DNA damage). Screening for potential deleterious effects on cells is a necessary step in the testing and/or development of compounds for any of a wide variety of uses in which plants, animals, and/or humans will be exposed to the compound. In addition, compounds that reduce or inhibit cell viability and/or growth may be useful as pharmaceuticals, disinfectants, etc. The microfermentors and microfermentor arrays may also be used to identify compounds that increase or enhance the growth of cells, that increase the ability of the cells to produce a desired metabolite or remove an undesired product, etc.

The invention encompasses the use of the microfermentors and microfermentor arrays to determine the response of cells to a compound. A "response" includes, but is not limited to a change in a parameter such as: viability, growth rate, production of a metabolite or other biosynthetic product, biotransformation of a compound, transcription of a gene, expression of a protein, etc. In general, the methods for using the microfermentors and microfermentor arrays include culturing a cell in the presence of a compound of interest and comparing the value of a parameter of interest in the presence of the compound with the value of the parameter in the absence of the compound or in the presence of a different concentration of the compound.

The microbioreactors of the invention may be used for gene expression studies of cells (e.g., bacteria, yeast, insect cells, mammalian cells, other eukaryotic cell types) including gene expression studies in which expression of a plurality of genes is measured in parallel. DNA microarray analysis is a powerful technology used for the characterization of a wide variety of biological phenomena at the molecular level. The global determination of gene expression with DNA microarrays for example could be used to study underlying differences of cells of different types, cells responses to different environmental stimuli, gene function and transcription. Microarray technology is increasingly applied in diverse fields as diverse as drug screening, environmental testing, and clinical diagnosis.

Briefly, microarray analysis of gene expression involves obtaining a sample containing RNA, e.g., a sample of cells, and applying RNA contained in the sample (or another nucleic acid obtained by reverse transcription of the RNA) to a solid support (e.g., a cDNA or oligonucleotide microarray) on which are immobilized a plurality of probes. cDNA microarrays consist of multiple (usually thousands) of different cDNAs spotted (usually using a robotic spotting device) onto known locations on a solid support, typically a rigid support such as a glass microscope slide. The cDNAs are typically obtained by PCR amplification of plasmid library inserts using primers complementary to the vector backbone portion of the plasmid or to the gene itself for genes where sequence is known. Full length cDNAs, expressed sequence tags (ESTs), or randomly chosen cDNAs from any library of interest can be chosen. Oligonucleotide microarrays, in which oligonucleotides rather than cDNAs are employed to detect gene expression, represent an alternative to the use of cDNA microarrays (Lipshutz, R., et al., *Nat Genet.*, 21(1 Suppl):20-4, 1999). In general, the experimental approach employed with an oligonucleotide microarray is similar to that used for cDNA microarrays. However, the shorter length of olignucleotides as compared with cDNAs means that care must be used to select oligonucleotides that hybridize specifically with transcripts whose level is to be measured.

Information regarding DNA microarray technology and its applications may be found in Heller, M J, *Annu Rev Biomed Eng.*, 4:129-53, 2002, and references cited therein. A variety of nucleic acid arrays have been developed and are known to those of skill in the art, including those described in: U.S. Pat Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; 5,658,734; WO 93/17126; WO 95/11995; WO 95/35505; EP 742 287; and EP 799 897.

In a typical microarray experiment, a microarray is hybridized with differentially labeled RNA or DNA populations derived from two different samples. Most commonly RNA (either total RNA or poly $A^+$ RNA) is isolated from cells or tissues of interest and is reverse transcribed to yield cDNA. In general, one or more nucleotide residues is modified to include a label, which may be directly or indirectly detectable. Generally the label is a directly detectable label, by which is meant that it need not react with another chemical reagent or molecule in order to provide a detectable signal. RNA expression is measured by monitoring hybridization of the RNA to the probes. Rather than using RNA directly, a transcription product of the RNA, e.g., a cDNA copy reverse transcribed from the RNA may be used. The RNA and/or cDNA can be amplified, preferably in a linear manner. Amplification can be performed prior to hybridization and/or following hybridization.

In general, cDNA derived from one sample (representing, for example, a particular cell type, tissue type or growth condition) is labeled with one label (e.g., one fluor) while cDNA derived from a second sample (representing, for example, a different cell type, tissue type, or growth condition) is labeled with the second label (e.g., a second fluor). Similar amounts of labeled material from the two samples are cohybridized to the microarray. A detector capable of quantitatively detecting label intensity is used to scan the microarray. Ratios of the different intensities at various positions represent the relative concentrations of cDNA molecules that hybridized to the cDNAs represented on the microarray and thus reflect the relative expression levels of the mRNA corresponding to each cDNA/gene represented on the microarray. In addition to the "two-color" approach, methods employing a single label and methods employing multiple labels can also be used. Rather than using cDNA derived from the mRNA for hybridization to a microarray, the cDNA can be transcribed to yield complementary RNA (cRNA), which can then be hybridized to a microarray. cDNA and cRNA derived from an initial RNA sample by reverse transcription, transcription, or any combination or reverse transcription and transcription in any order and any number of times, are referred to herein as "nucleic acid transcription products" of such RNA. Labels other than fluorescent labels, e.g., biotin, enzymatic labels, etc., can also be used. For example, cRNA incorporating biotin can be hybridized to a microarray. Antibiotin antibody with an attached fluorphore is added, and the fluorescent signal is detected. Thousands of data points are generated in a typical microarray analysis and can be processed in a variety of ways using different algorithms (e.g., hierarchical clustering) and software programs, e.g., Significance Analysis of Microarrays (SAM; Stanford University) to facilitate data analysis.

While microarray analysis is well understood in general and has found numerous applications, the techniques continue to be developed. In particular, there is an ongoing need to provide methods for performing microarray analysis on very small samples. The inventors have unexpectedly discovered that it is possible to reliably perform gene expression analysis using microarrays on samples of cells cultured in microbioreactors, including those having very small interior volumes, e.g., 200 microliters or less, 50 microliters or less, etc. As described in Example 11, the inventors successfully performed microarray analysis to measure gene expression from cells cultured in a microbioreactor with a vessel having a volume of only 50 microliters. Microarray analysis was successfully performed using only 500 ng of total RNA. Purified mRNA could also have been used. The inventors have therefore both recognized the desirability of using microarray analysis for gene expression profiling of cells cultured in microbioreactors and have enabled methods for doing so. The invention thus provides a heretofore unrealized extension of microarray technology and a heretofore unrealized application of microbioreactors having very small vessel volumes, including batch, fed-batch, and continuous microbioreactors. Details of the specific reagents and conditions used to optimize and enable the method are provided in Example 11. Accordingly, the invention provides a method of monitoring gene expression comprising: (i) culturing cells in a microbioreactor, wherein the microbioreactor comprises a vessel with an interior volume of 200 µl or less and means for providing oxygen to the interior of the vessel; (ii) harvesting some or all of the cells; (iii) contacting RNA obtained from the cells, or a nucleic acid transcription product of such RNA, with a microarray comprising probes for a plurality of genes under conditions such that hybridization occurs; and collecting a signal from the microarray. In various embodiments of the invention either prokaryotic (eubacteria, archaebacteria) or eukaryotic cells (e.g., yeast or other fungi, protozoa, insect, mammalian, etc.) may be used. Cells infected with an infectious agent such as a bacterium or virus can be used.

The continuous increase in the public release of complete genomic sequences of microorganisms offers enormous opportunity for detailed investigations of the functioning of these organisms. Genomic expression assays provide an unprecedented ability not only to look at a single aspect of physiology, but also to see how a particular gene, regulon, or modulon interacts with other aspects of physiology. Combining high-throughput growth physiology data with high-throughput gene expression values represents a fundamental improvement over present screening technologies and would lead us to the discovery of new and/or improved microorganisms to answer medical, environmental and biological problems. Thus the invention provides methods that performing one or more gene expression analyses on cells cultured in a microbioreactor, wherein at least one bioprocess parameter is monitored during the culture period. Results of the gene expression analysis may be correlated with the bioprocess parameter data. In addition to, or instead of, monitoring a bioprocess parameter, images of the culture may be obtained. This allows correlation of features such as cell morphology (e.g., under various culture conditions) with gene expression. Cells can be modified to express fluorescent or chemiluminescent proteins, and the expression of these proteins can also be monitored during or after the culture period. Thus the invention encompasses collecting one or more optical signals during the culture period. Results from the gene expression analysis, optionally also considering results from monitoring a bioprocess parameter and/or image, can be used to select a cell strain or culture condition. Thus the invention envisions collecting gene expression profiles from cultures of multiple cell strains cultured in parallel under the same or different culture conditions (e.g., different media), and comparing the gene expression profiles. For example, upregulation of genes whose expression is indicative of cell stress may suggest that a particular condition is undesirable. A cell strain in which stress response genes are not upregulated under a given culture condition may be particularly desirable. These examples provide only an overview of the various applications of gene expression analysis in conjunction with monitoring of bioprocess parameters for improving strain selection, bioprocess parameter selection, etc.

VII. Evaluation of Microfermentors and Comparison with Conventional Fermentor Technology In certain embodiments of the invention results in the microfermentor reliably predict results that would be obtained by scaling up a bioprocess, e.g., to the scale of a commercially available fermentor. For example, in certain embodiments of the invention a strain that is identified as an optimum strain when cultured in a microfermentor is also an optimum strain when cultured under substantially the same conditions in a conventional fermentor. In certain embodiments of the invention conditions that lead to maximum production of a biosynthetic product or metabolite or that lead to maximum biotransformation or removal of an undesired compound when cells of a particular type are cultured in a microfermentor also lead to maximum production of a biosynthetic product or metabolite or to maximum biotransformation or removal of an undesired compound when cells of the same type are cultured in a conventional fermentor, e.g., a bench-scale fermentor having a culture vessel having a volume of at least 0.5 liters, or a production scale fermentor, which may have a volume of hundreds or thousands of liters. However, it is not necessary that optimum conditions in a microfermentor correspond exactly to optimum conditions in a conventional fermentor, or that rates (e.g., rates of production or removal of a compound, rates of nutrient flux, rates of gas or heat transport, etc.) under a given set of conditions correspond exactly to rates that would be obtained under substantially identical conditions in a conventional fermentor. Rather, in certain embodiments of the invention it is sufficient if conditions and/or rates obtained when cells are grown in a microfermentor may be used to predict behavior when the process is scaled up.

For purposes of initially determining how conditions in a microscale bioreactor correspond or translate to conditions in a larger scale bioreactor, it is desirable to employ a cell type or strain that is well characterized, e.g., in terms of its physiology and behavior under different conditions. *Escherichia coli* represents an attractive prokaryotic cell choice for use in analyzing microscale bioreactor performance and scale-up. There is a large body of literature describing the physiology of this organism (see, e.g., 41) and its behavior under different reactor conditions. In addition, this organism is currently used in a range of commercial processes including production of small molecules and screening of gene libraries. The chemical composition of this organism is very well understood in terms of elemental composition and major biochemical fluxes. Finally, this organism has been extensively studied at the genetic level; vast collections of mutants are available with many useful properties, and the complete genomic sequence of this species has been determined. A comparable degree of information on the budding yeast *Saccharomyces cerevisiae* is available, making this an attractive eukaryotic cell type for use in analyzing microscale bioreactor performance and scale-up.

In a number of organisms, various promoters are known to respond to different environmental conditions such as temperature, ion concentration, oxygen concentration, etc., or to physiological insults such as DNA damage, oxidative stress, etc, by increasing or decreasing transcription from a linked gene. In order to determine whether bacteria being cultured in a microfermentor are experiencing physiological stress, and in order to compare growth properties in the microfermentor with growth properties in a larger scale fermentor, strains bearing reporter genes in which such a promoter controls expression of a reporter gene (e.g., luciferase) may be employed.

Various modifications and variations of the invention described herein will be evident to one of ordinary skill in the art and are also within the scope of the claims.

EXAMPLES

Example 1

Fabrication of a Microscale Bioreactor

Poly(dimethylsiloxane) (PDMS) was selected as the microfermentor fabrication material in part because of its biocompatibility and optical transparency in the visible range. The high gas permeability of this material also allows it to be used as the material for an aeration membrane. Glass was selected as the microfermentor base for its transparency and rigidity.

Figure 10:
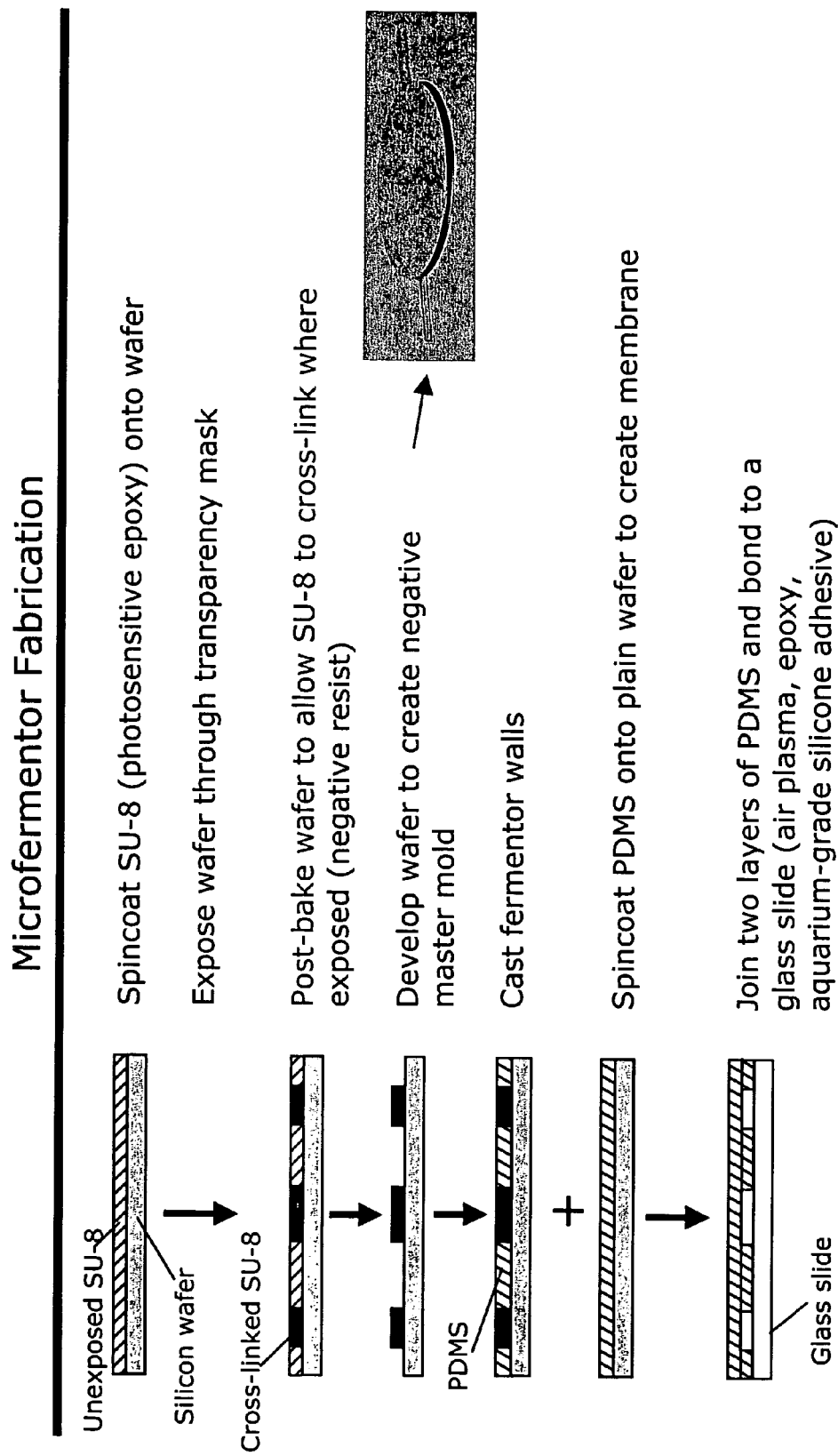
FIG. 10 is a flowchart of the fabrication procedure employed in one embodiment of the invention.
Figure 11:
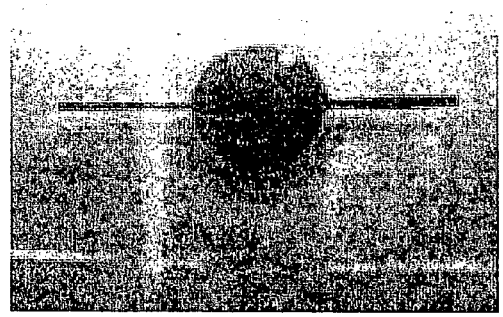
FIG. 11 shows a top view of a completed microfermentor fabricated as outlined in FIG. 10 and filled with phenol red.

The fabrication procedure used is depicted in FIG. 10. Fabrication of the microfermentor was carried out using soft lithography as described in (58). In the first step of the fabrication process photolithography was used to fabricate a negative master out of silicon and the photo-definable epoxy SU-8. The body of the microfermentor was then cast in PDMS by squeezing the liquid polymer between the negative master and a piece of cured and passivated (silanized) PDMS. The aeration membrane was made by spin-coating the liquid polymer onto a blank wafer. The body and the membrane were subsequently joined and attached to a glass slide using epoxy or other suitable adhesives (e.g., silicone adhesives). (An air plasma seal was initially used to join the membrane to the fermentor body. However, this method appeared to result in a higher rate of evaporation of microfermentor contents, possibly due to the creation of $SiO^-$ groups on the surface of the PDMS that render the surface hydrophilic. Evaporation can be avoided by, for example, maintaining the microfermentor in a humidified chamber.) A top view of a completed microfermentor filled with phenol red is shown in FIG. 11. The microfermentor has a diameter of approximately 5 mm and a depth of approximately 300 µm. The working volume of the microfermentor vessel is approximately 5 µl. Channels with a 300 µm×300 µm square cross-section extend outwards from and communicate with the vessel interior.

Example 2

Modeling Aeration Within a Microscale Bioreactor

Modeling of oxygen diffusion into the microfermentor was carried out using a one-dimensional resistance-in-series model of the membrane and the medium, taking oxygen consumption to be a zeroth-order reaction term (constant oxygen consumption/viable cell). For calculations at 35° C., an oxygen diffusivity in PDMS of $3.4 \times 10^{-5}$ cm$^2$/s and a solubility of 0.18 cm$^3$ (STP)/cm$^3$/atm were assumed (44). For oxygen in water a diffusivity of $2.5 \times 10^{-5}$ cm$^2$/s and a solubility of 7 mg/l were used (45), and it is assumed that values for culture medium would be approximately the same. A typical *E. coli* oxygen uptake rate (OUR) of 30 (mmol O$_2$)/(gram dry cell weight/h) was assumed (46).

The models assumed a stagnant medium (no mixing). If some method of mixing is implemented, the maximum depth of the microfermentor will increase. The model assumes steady state conditions (see below for transient analysis of oxygen transport during growth). For the case where cells are spread uniformly throughout the microfermentor volume (homogeneous case), the following equations were obtained:

$$C_r - C_o = R_V \left[ \frac{td}{D_{PDMS}} + \frac{d^2}{2D_{H_2O}} \right]$$

Where: $R_V$ is the volumetric consumption term

Figure 12:
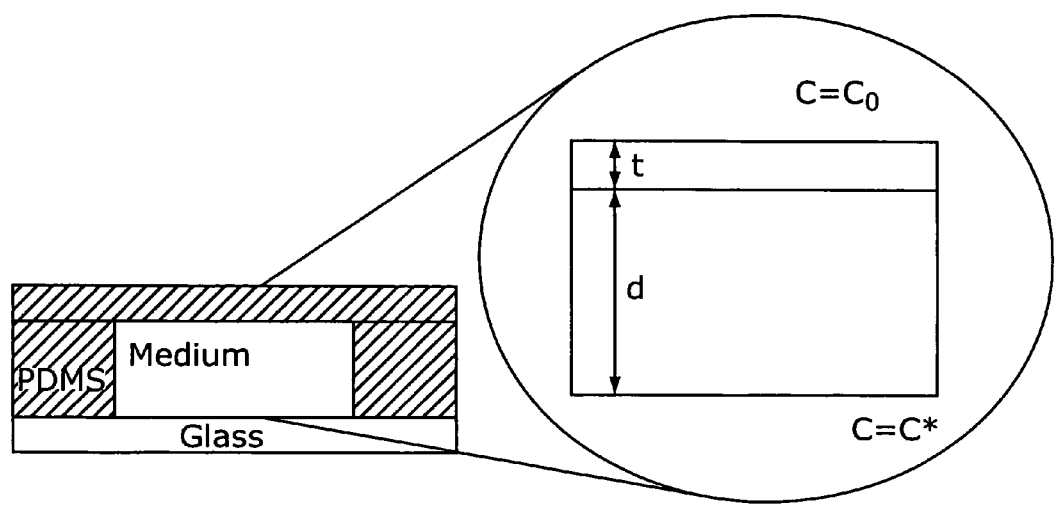
FIG. 12 illustrates a one-dimensional resistance-in-series model of the membrane and the medium, which was used to model oxygen diffusion into a microfermentor.

D is the diffusivity of oxygen in PDMS and H$_2$O, respectively $C_r$ (C* in FIG. 12) is the critical oxygen concentration below which bacteria turn on anaerobic metabolic pathways (Cr=0.0082 mmol O$_2$/L) (from 55)

Because the solubility of oxygen in water is the main limitation (and not the permeability of the PDMS membrane) the model can be simplified by considering the medium only.

$$C(x) = C_o + \frac{R_V d}{D} x - \frac{R_V}{2D} x^2$$

In the equation above C is the concentration at x, and x is the axis along the microfermentor depth.

Figure 13A:
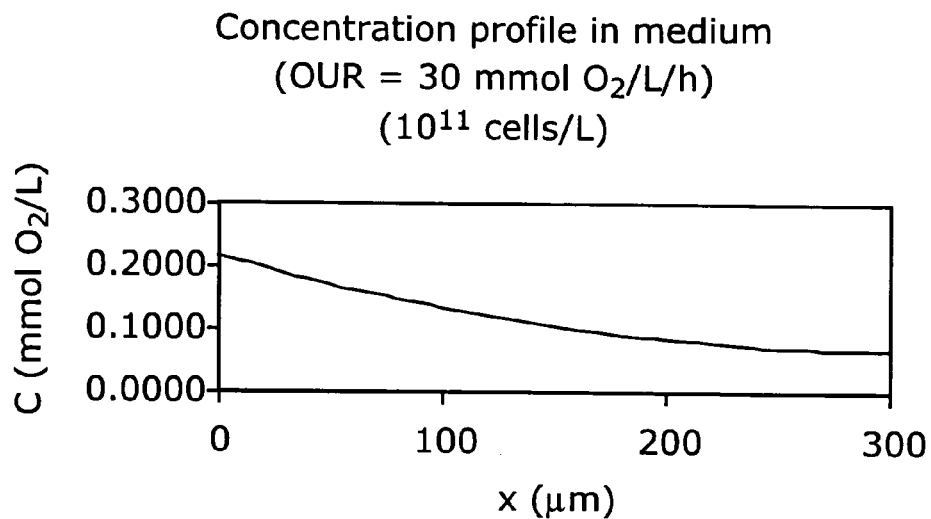
FIG. 13A shows the calculated steady state oxygen concentration using a one-dimensional resistance-in-series model obtained assuming a cell population homogenously spread throughout the medium.

The resulting plot of the oxygen concentration profile within the medium is shown in FIG. 13A.

For the case in which all cells are at the bottom of the microfermentor and consumption is heterogeneous (boundary condition), the following diffusion equation applies:

$$C_o - C_r = F \left[ \frac{t}{D_{PDMS}} + \frac{d}{D_{H_2O}} \right]$$

Here F is the flux of oxygen at the bottom of the microfermentor, corresponding to the oxygen consumption per unit area. This is converted to a volumetric term by multiplying by the ratio (A/V).

As in the homogeneous case discussed above, the maximum flux will not be realized because the limiting factor is again the solubility of oxygen in water. This can be FIG. 13B, which shows an oxygen concentration profile in the PDMS and the medium itself. The assumptions for this figure are again a cell population of approximately 10$^{11}$ cells/L, and a corresponding OUR of 30 mmol O$_2$/L/h. A membrane thickness of 100 µm, and a microfermentor depth of 300 µm were used.

Figure 13B:
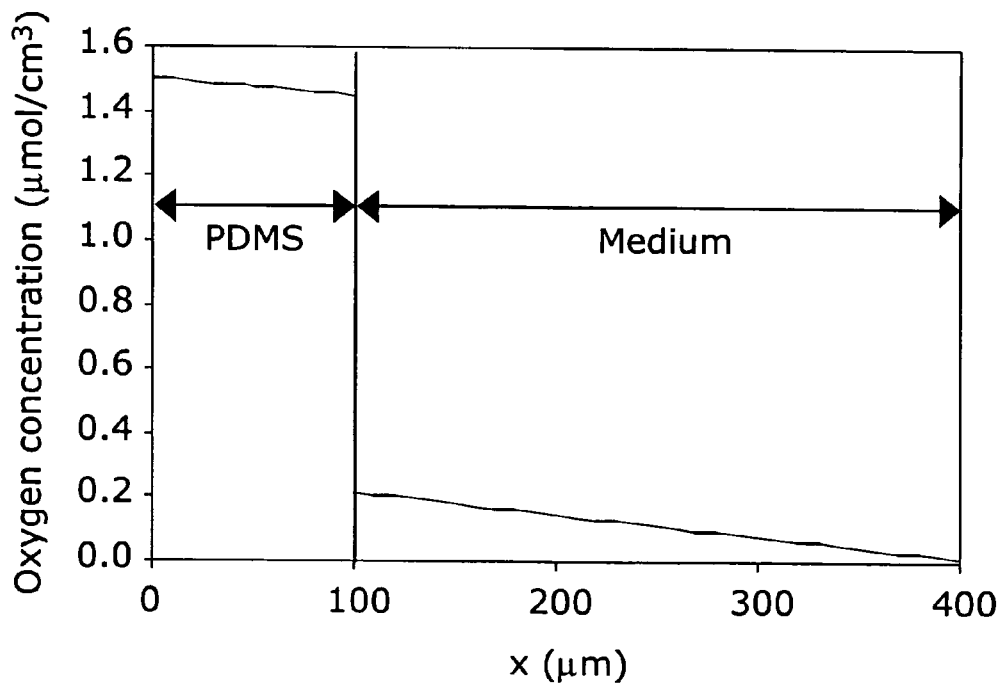
FIG. 13B shows the calculated steady state oxygen concentration profile using a one-dimensional resistance-in-series model of membrane and medium obtained assuming a membrane thickness of 100 µm, a microfermentor depth of 300 µm, and a cell population of $10^{11}$ cells/L, with the cells at the bottom of the microfermentor (heterogenous case).

As shown in FIG. 13B, the diffusion process is limited primarily by the low solubility of oxygen in water, as evidenced by the large drop-off in oxygen concentration between the membrane and the water. The diffusivity of oxygen in both phases is high enough that the slope of the profile in each phase is relatively shallow. In this case the high oxygen diffusivity combined with a high solubility in PDMS suggested that similar results would have been achieved using a thinner membrane.

The model indicates that due to the high solubility of oxygen in PDMS, the diffusivity of oxygen through the membrane could be up to an order of magnitude smaller and still provide adequate oxygenation. Therefore, any membrane with a high oxygen solubility would be compatible with the design, even if the diffusivity of the gas was 10-fold lower than that in PDMS. Alternately, if the diffusivity was as high as that in PDMS, the solubility could be more than an order of magnitude lower.

In terms of permeability:

P=DS

The permeability of PDMS is 800 Barrer (1 Barrer=10$^{-10}$ cm$^3$(STP)·cm/cm$^2$·s·cm Hg) (44).

This model suggests that any membrane with an oxygen permeability>80 Barrer will work with the design, and the permeability could probably be even lower (still relatively high diffusivity, but solubility could be lower).

Figure 23:
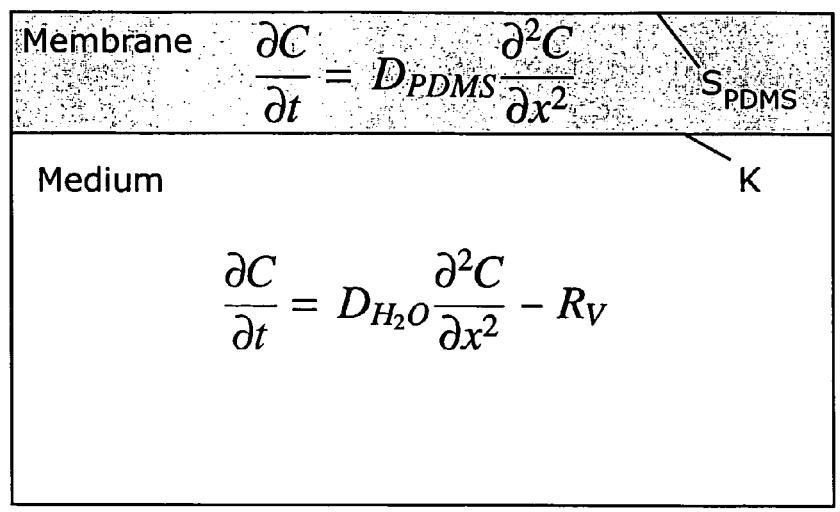
FIG. 23 shows modeling of oxygen transfer in a microbioreactor as resistances-in-series.

The model described above establishes the feasibility of the microfermentor design based on a steady state analysis. The design of the microfermentor can be further validated by a transient analysis of the oxygen transport during growth. FIG. 23 shows the two oxygen transport regions in the microfermentor (parameters used are listed in Table 4). The transient model assumes exponential growth (the most oxygen demanding growth phase) of homogeneously-dispersed cells, and it is based on the three equations below.

$$\frac{\partial C}{\partial t} = D \frac{\partial^2 C}{\partial x^2} - R_V$$

$$R_V = OxygenUptakeRate = -Y_{o/x} \frac{dN}{dt}$$

$$\frac{dN}{dt} = N \mu_{max}$$

Figure 24:
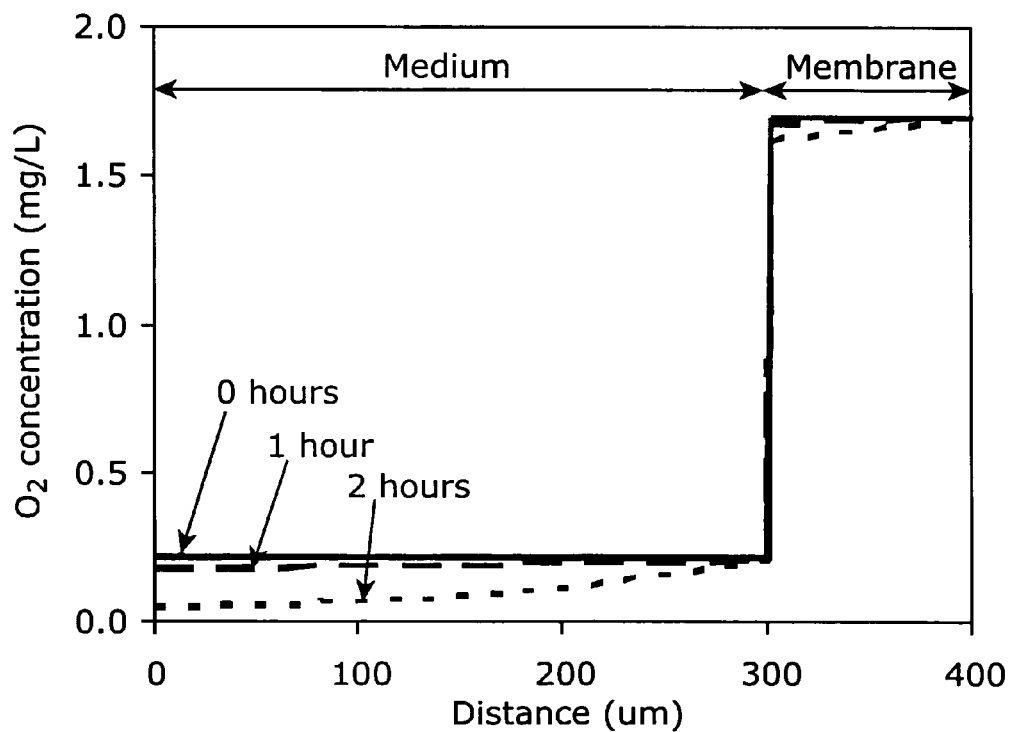
FIG. 24 shows the modeled oxygen concentration profile across PDMS and membrane at t=0,1,2 hours (with cell growth modeled as exponential growth).

FIG. 24 shows the oxygen concentration profile across the membrane and the microbioreactor at increasing time. As in the previous example, the major resistance to mass transfer occurs in the medium rather than the membrane, a result of the low solubility of oxygen in water. It was found that a depth of 300 µm allowed sufficient oxygenation to reach a final cell number ~$10^{12}$ cells/L. From this figure it is also apparent that a concentration gradient exists within the medium as oxygen is gradually depleted.

TABLE 4

List of parameters used in models

| Parameter | Definition | Value | Reference |
|---|---|---|---|
| $S_{PDMS}$ | †Solubility of $O_2$ in PDMS | 0.18 $cm^3$(STP)/$cm^3 \cdot$ atm | 44 |
| $D_{PDMS}$ | †Diffusivity of $O_2$ in PDMS | $3.4 \times 10^{-5}$ $cm^2$/s | 44 |
| $S_{H2O}$ | †‡Solubility of $O_2$ in water | 7.36 mg/l | 45 |
| $D_{H2O}$ | †‡Diffusivity of $O_2$ in water | $2.5 \times 10^{-5}$ $cm^2$/s | 45 |
| K | †‡PDMS-$H_2O$ partition coefficient | 0.129 | Calculated |
| $Y_{O/X}$ | Yield of biomass on oxygen | 1 $g_{O2}$ consumed/$g_{DCW}$ (Dry Cell Weight) produced | Literature |
| $N_O$ | Initial number of cells | $3.8 \times 10^7$ cells/ml | Experiment |
| $t_d$ | Doubling time | 25 min | Experiment |
| $\mu_{max}$ | Maximum specific growth rate | 0.0278 $min^{-1}$ | Experiment |
|  | Conversion | $2.8 \times 10^{-13}$ $g_{DCW}$/E. coli cell | 82 |
| C* | Percent oxygen at saturation | 100% | Definition |

†At 35° C., in equilibrium with 0.21 atm of oxygen
‡Values for pure water were used since only 8 g/l of glucose was present in the medium
*Critical oxygen concentration = 0.0082 mmol/l (~3.6% of air saturation) (55)

TABLE 5

List of variables used in models

| Parameter | Description |
|---|---|
| C | Concentration of oxygen |
| D | Diffusivity of $O_2$ in each phase |
| $R_V$ | Volumetric accumulation term |
| N | Number of cells |
| μ | Specific growth rate of cells |

Example 3

Setup of a Microscale Bioreactor System

FIG. 14 shows a schematic of a microscale bioreactor system with associated optical excitation and detection sources. Optical fibers transmit light to the bottom of the fermentor. Biomass is monitored by measuring the amount of light transmitted to the collecting lens above.

Figure 15A:
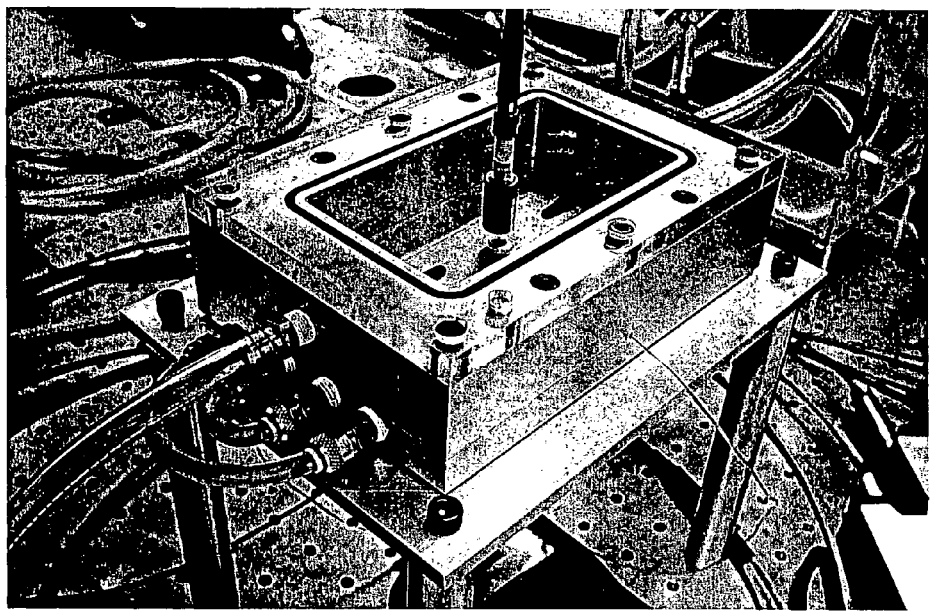
FIGS. 15A and 15B depicts two views of a microfermentor system in which a microfermentor is placed in an environmental control chamber. The transparent glass slide is not readily visible.
Figure 15B:
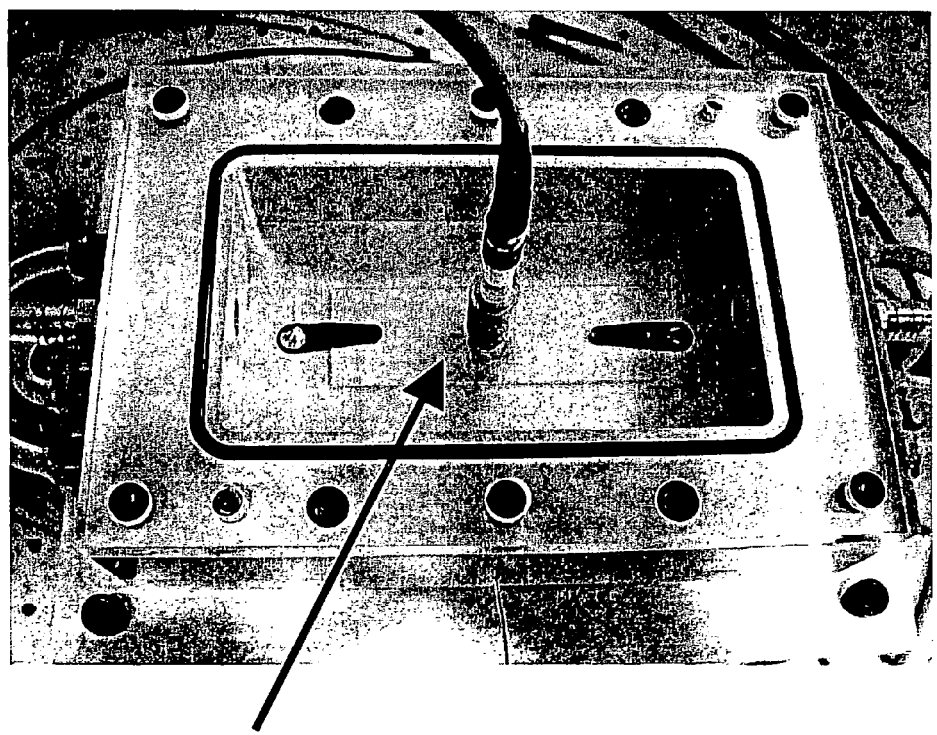

The microfermentor is placed in an enclosed chamber designed to facilitate environmental control during fermentations. The chamber is fabricated from aluminum and has a screw-on lid that can be sealed with an O-ring. FIG. 15A depicts the chamber with the microfermentor inside. FIG. 15B is a second view to more clearly show the microfermentor. (Note that the slide that forms the base of the microfermentor is transparent.) In this system, evaporation from the microfermentor is controlled by making the chamber airtight and by maintaining the air within the chamber at high humidity, e.g., 100% humidity. This is accomplished by placing open reservoirs of water beside the microfermentor within the chamber. The large volume of the chamber (~190 $cm^3$) as compared to the volume of the microfermentor ensures that sufficient oxygen is present to supply the needs of the growing bacteria throughout a run. Less than 1% of available oxygen is consumed by respiring bacteria during the course of a 12 hour fermentation. The chamber is maintained at a constant, desired temperature by flowing heated water from a water bath through channels within the chamber base using a heating circulator (DC-10, Thermo Haake, Karlsruhe, Germany).

Optical fibers run to the center of the chamber cover and base, above and directly below the microfermentor respectively. These fibers allow both transmissive and reflective optical measurements to be made. The fiber positioned above the microfermentor is attached to a collecting lens (F230SMA-a), ThorLabs) that increases the solid angle of capture of light emitted from the fiber below and transmitted through the microfermentor.

Example 4

Monitoring Bioprocess Parameters of Cells Cultured in a Microscale Bioreactor

Preparation and Inoculation of Cells

E. coli were cultured at 37° C. for 12 hours in LB medium+ amp with or without addition of glucose (43). Immediately prior to introduction of the cells into the microfermentor, a 5% inoculum was introduced into fresh medium. Prior to inoculation the microfermentor was sterilized by a 60 second exposure to UV light at a wavelength of 254 nm. Inoculation of the cells was accomplished using a syringe to drive fluid through the channels and into the vessel interior. The channel holes, which self-seal to a large extent, were then further sealed using epoxy to minimize evaporation. Various epoxies and adhesives (e.g., Epoxy—ITW Performance Polymers, Part No: 46409/20845, Silicone adhesive—American Sealants, Inc., ASI #502 Silicone) have been used with no evidence of deleterious effects due to contact with cells. However, biocompatibility of the adhesive may be a consideration. Once filled, the microfermentor was placed into the chamber and secured to the base. The chamber was then closed with an airtight seal and optically sealed to prevent stray light from interfering with subsequent measurements.

Measurement of Biomass

Quantification of biomass was based on the transmission of light through the microfermentor. The light source is an orange LED with a peak wavelength of 609 nm or a helium neon (HeNe) laser with a peak wavelength of 636 nm. This light is coupled into a 600 μm optical fiber as described above. A 600 μm fiber above the microfermentor carries the transmitted light to a spectrometer (OCS-PDA, Control Development). A photodetector (PDA55, ThorLabs) is used to check for temporal power drift from the light source.

Optical density (OD) is calculated using:

$$OD = \log_{10}(1/T)$$

where T=transmittance of light calculated from the intensity, I, using:

$$T = I_{signal}/I_{ref}$$

A curve for optical density as measured in a cuvette by a conventional spectrometer was obtained by diluting a sample of the fermentation medium by a factor of 10, so that it fell within into the linear portion of the spectrometer range. This value of the optical density was then used to determine the actual optical density at all other dilutions.

Measurement of Dissolved Oxygen

Fluorescence quenching of Ruthenium II tris(4,7-diphenyl-1,1-phenanthroline)$^{2+}$ was used to measure the dissolved oxygen at the bottom of the microfermentor. The glass slide that forms the base of the microfermentor was coated with sol-gel containing this compound. These slides are available commercially (Foxy sol-gel slides, Ocean Optics). A bifurcated cable carries light at the excitation wavelength to the base of the microfermentor. The light source is USB-LS-450, Ocean Optics). Emitted light that is captured by the optical fiber is then carried back to the spectrometer (USB2000-FL, Ocean Optics), where the percent dissolved oxygen is calculated using OOISensors Software (Ocean Optics).

Results

Typical viable cell counts (based on optical density calculated from transmission data) for *E. coli* growing in the microfermentor in LB+amp medium without the addition of glucose indicate a cell density of approximately $4 \times 10^9$ cells/mL ($4 \times 10^{12}$ cells/L), comparable to that employed in large-scale fermentation processes.

Figure 16:
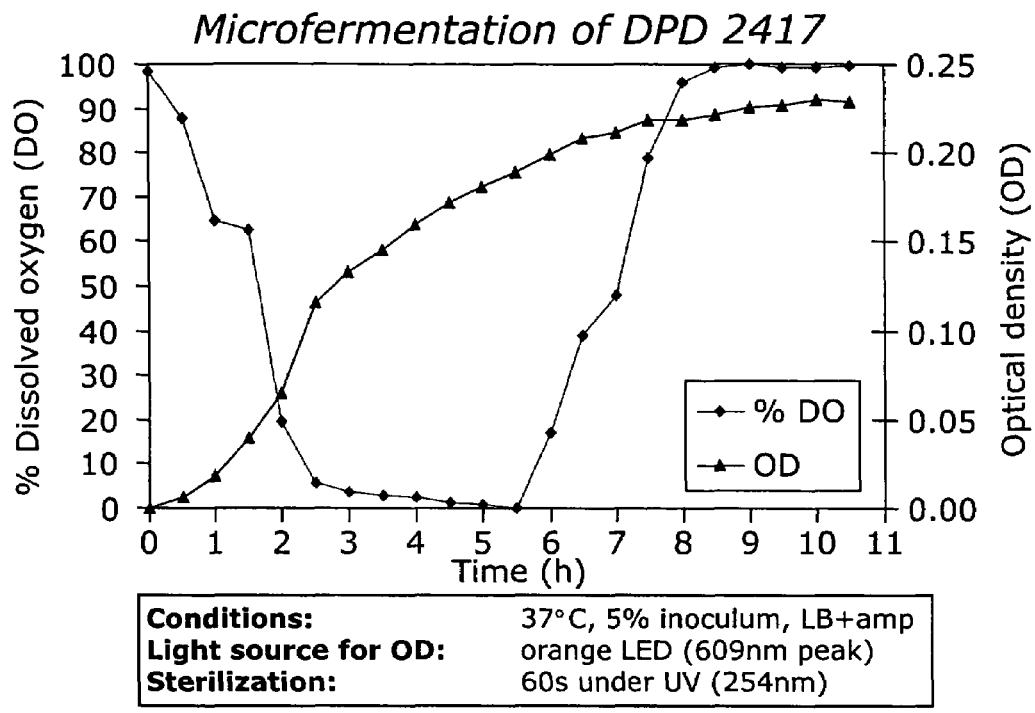
FIG. 16 shows optical density and dissolved oxygen data obtained from batch fermentation of E. coli in a microfermentor in medium without glucose.

FIGS. 16 shows optical density and dissolved oxygen data obtained from batch fermentation of *E. coli* cultured in LB+amp in a microfermentor. Oxygen was provided via the PDMS membrane, and no active stirring of the medium took place. Dissolved oxygen was measured using the Ru-based oxygen sensor. Three distinct phases of growth can be observed in FIG. 16. During the first stage, bacteria are in the exponential phase of growth and are multiplying with an apparent doubling time of 30 minutes. (The doubling time is referred to as "apparent" because in accordance with the results described above, the optical density predictably underestimates the actual biomass.) During this first stage enough oxygen is supplied by diffusion to support this rapid growth. The second stage is reached when the level of measurable oxygen in the medium drops close to zero, and oxygen is utilized by the bacteria as quickly as it diffuses into the microfermentor vessel. During this phase the bacteria switch to linear growth. Finally, the third stage shows the bacteria reaching a stationary phase. During this stage oxygen levels return to saturation. The time required to reach saturation can be predicted from the non-steady-state one dimensional diffusion equation:

$$\partial C/\partial T = D(\partial^2 C/\partial x^2)$$

Figure 17:
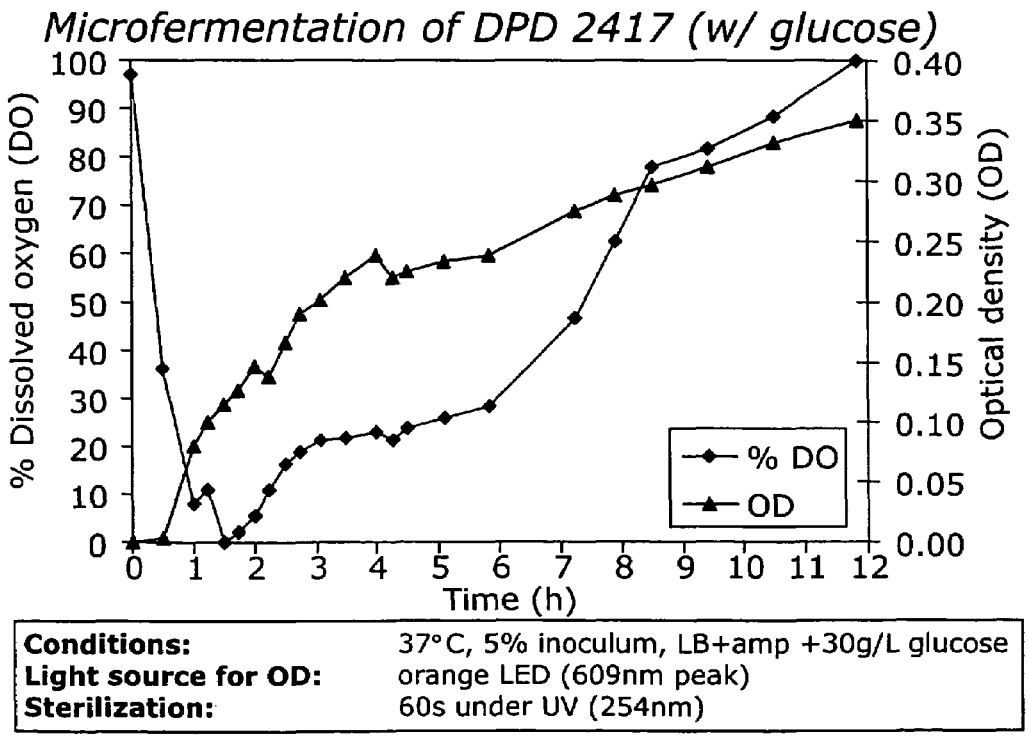
FIG. 17 shows optical density and dissolved oxygen data obtained from batch fermentation of E. coli in a microfermentor in medium containing 30 g/L glucose.
Figure 18A:
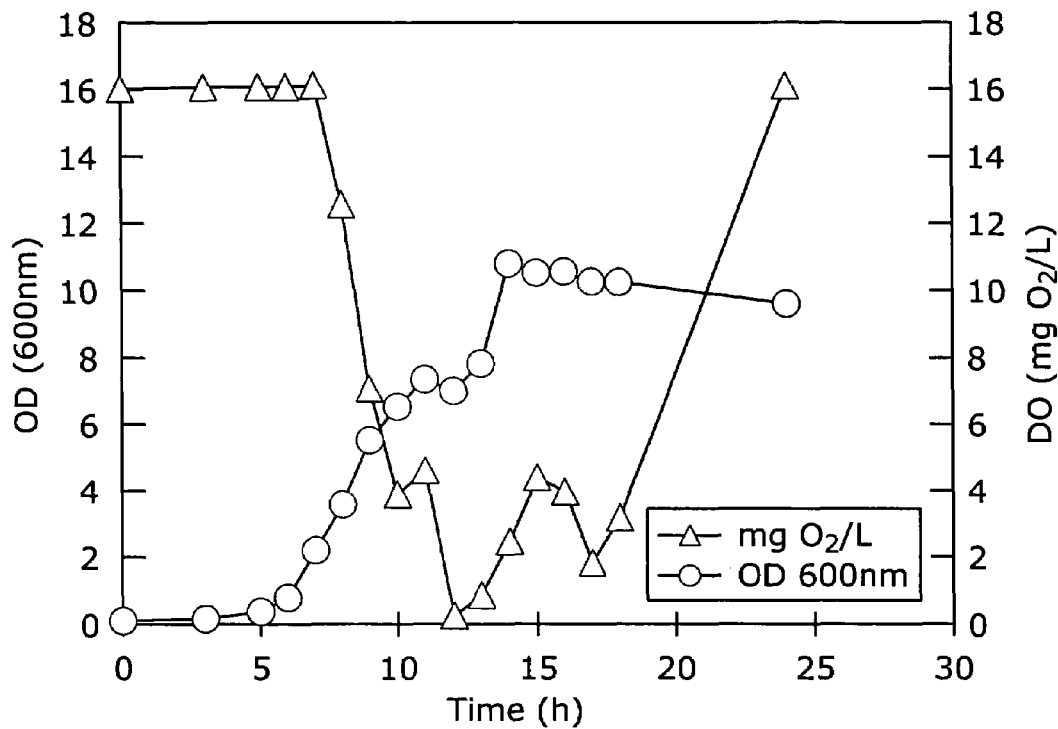
FIGS. 18A and 18B show optical density and dissolved oxygen data obtained from batch fermentation of E. coli in a bench scale fermentor.
Figure 18B:
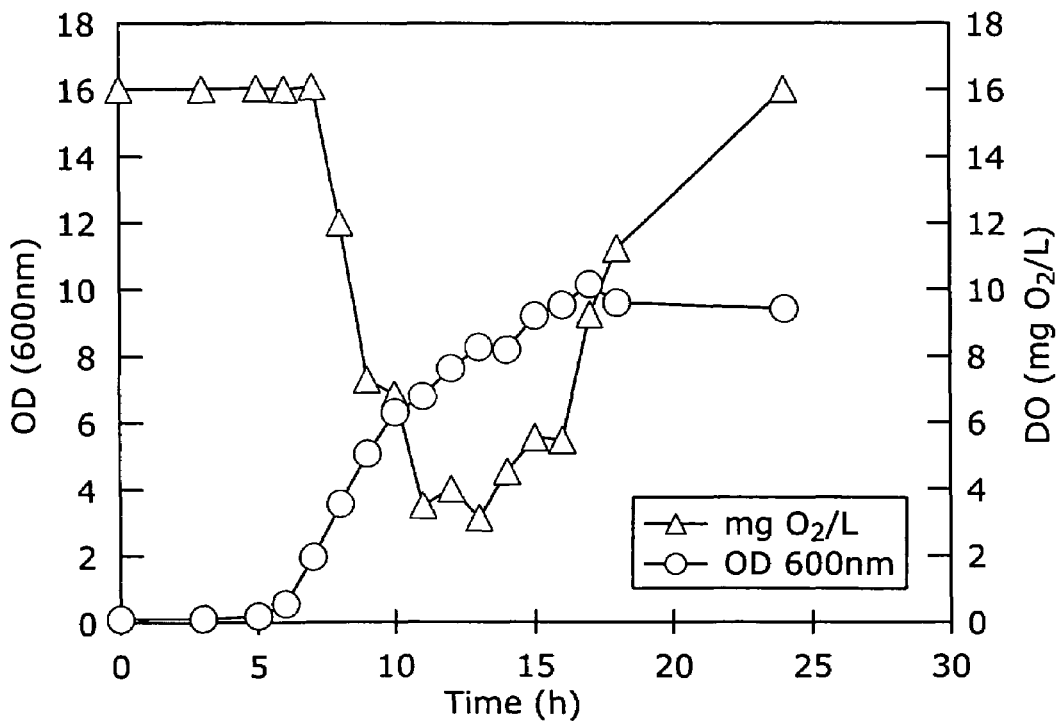

This results in an estimate on the order of minutes needed to fully reoxygenate the microfermentor to a depth of 300 µm. This time is shorter than the measured time of 2.5 hours shown in FIG. 17, but the longer reoxygenation time required is consistent with the observed accompanying increase in biomass. FIG. 17 shows a comparable curve for *E. coli* cultured in LB/amp+30 g/liter glucose. FIGS. 18A and 18B show fermentation of *E. coli* cultured in LB/amp+30 g/liter glucose in a 0.5 liter bench scale fermentor (Sixfors) at 37 degrees, 500 RMP, aeration 2 VVM (50% $O_2$, 50% $N_2$). The growth curve and curve of oxygen concentration within the microscale bioreactor show similar trends to that obtained in the bench-scale fermentor.

Example 5

Figure 19:
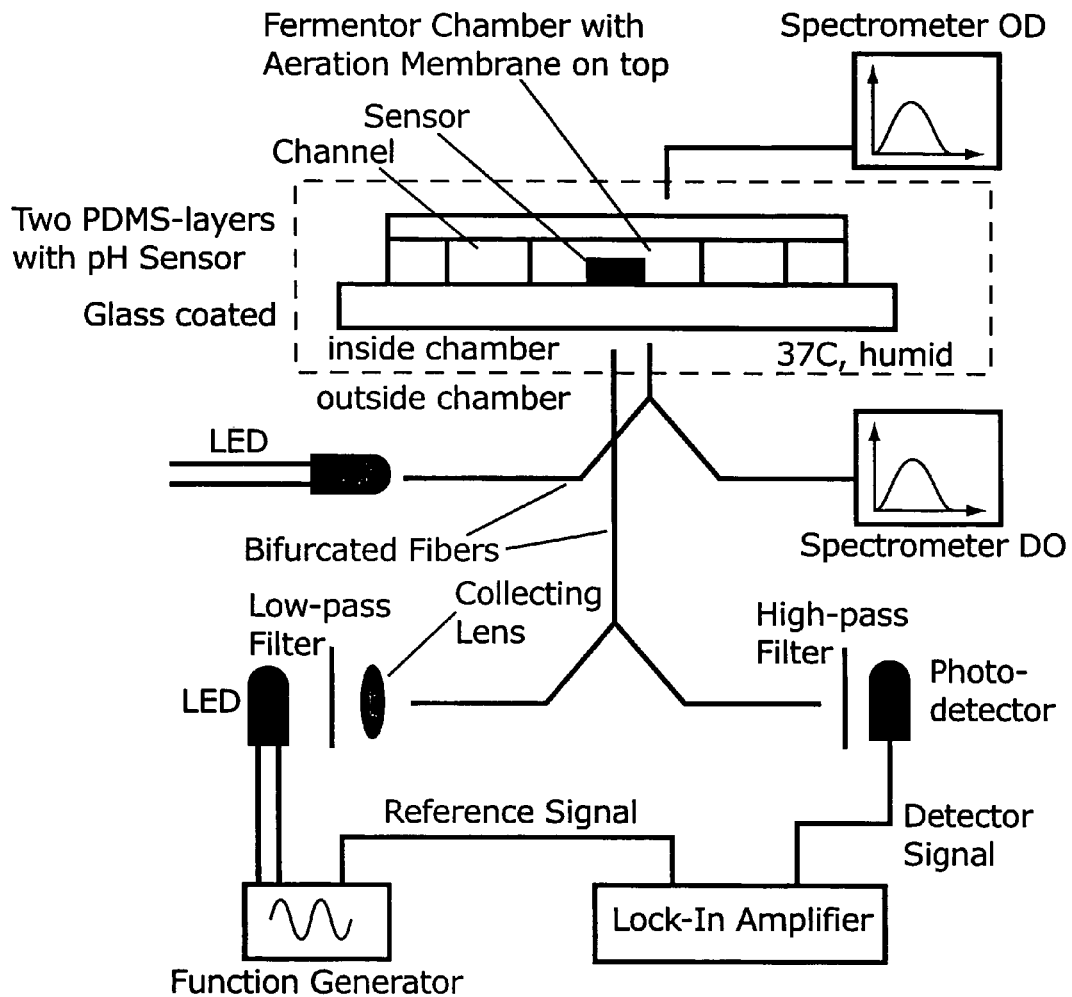
FIG. 19 shows a schematic diagram of an embodiment of the invention in which biomass, dissolved oxygen, and pH can be measured simultaneously.

FIG. 19 shows a schematic diagram of an embodiment of the invention in which biomass, dissolved oxygen, and pH can be measured simultaneously. The microfermentor was constructed and housed in a chamber essentially as described in Examples 3 and 4. Optical density was used as a measurement of biomass. To measure dissolved oxygen, the fluorophore described above, whose fluorescence is quenched in the presence of oxygen, was excited by an LED, and the intensity of the emission was read using a spectrometer. The dissolved oxygen can also be measured using a fluorescence lifetime measurement. The pH was measured by detecting fluorescence lifetime changes in a pH sensorfoil (Presens, Regensburg, Germany) located within the microfermentor. The lifetime of the fluorescence was measured by detecting the phase-shift of the fluorescence with respect to the intensity-modulated LED using a lock-in amplifier. Bifurcated optical fibers were inserted into the bottom and top of the chamber to allow the various optical measurements to be performed.

Figure 20:
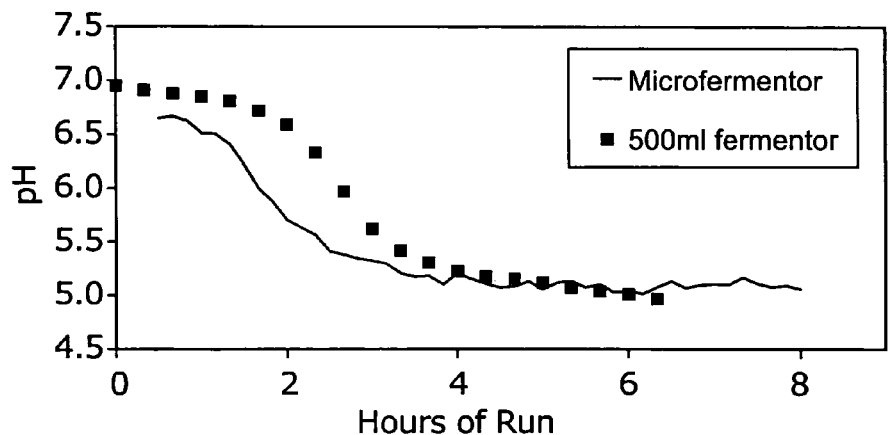
FIG. 20 is a graph comparing pH curves in the microfermentor and in a 0.5 L bench scale fermentor (Sixfors).

Dissolved oxygen and biomass were measured as described in Example 4, and similar results were obtained. FIG. 20 is a graph comparing pH curves in the microfermentor and in a 0.5 L bench scale fermentor (Sixfors). The pH in the bench-scale fermentor drops after approximately 2 hours and reaches a pH of ~5 after 6 hours. A similar trend can be observed in the microfermentor, in which the pH drops to ~5 after 5 hours.

Example 6

Strain Selection Using a Microscale Bioreactor Array

Xylitol, a naturally occurring sugar alcohol, is a promising low-calorie sweetener that has lower calories than sucrose and yet exhibits comparable sweetness. It is presently as a dental caries preventive sweetener and also finds use in fluid therapy in the treatment of diabetes. For these reasons, it is expected that the demand of xylitol will increase in future. Thus the demand for xylitol is expected to increase in future.

Current industrial production of xylitol mainly relies on hydrogenation of D-xylose as disclosed in U.S. Pat. No. 4,008,285. D-Xylose used as a raw material is obtained by hydrolysis of plant materials such as trees, straws, corn cobs, oat hulls and other xylan-rich materials. However, such D-xylose, which is produced by hydrolysis of plant materials, is rather expensive and has low purity. Other production methods, utilizing D-arabitol as a starting material, are complex and involve multiple steps. Attempts to use genetic engineering to develop a microorganism with improved ability to produce xylitol have met with only limited success. Therefore, it is desirable to identify a microorganism that can produce xylitol through a single step by fermentation starting from glucose as used in the production of other saccharides and sugar alcohols.

To address this need, osmophilic microorganisms are collected from nature by enrichment culture. A medium containing 20% D-glucose, 1% yeast extract (Difco), and 0.1% urea is introduced into test tubes in an amount of 4 ml each, and sterilized at 120° C. for 20 minutes. Soil samples collected from various locations in the Cambridge, Massachusetts area are inoculated into the medium, and cultured at 30° C. for 4 to 7 days with shaking. When bacterial growth is observed, the cultures are plated on an agar plate having the same composition, and incubated at 30° C. for 1 to 3 days. Single colonies were isolated.

Approximately 2000 strains of osmophilic bacteria obtained as described above are cultured in individual microfermentors within a microfermentor array in a medium containing 20% (w/v) D-glucose, 0.1% urea, and 0.5% yeast extract at 30° C. for periods ranging from 12 hours to 5 days. The microfermentors have a working volume of 5 µl and are equipped with means to monitor biomass and oxygen concentration. Each microfermentor delivers oxygen to the interior of the microfermentor vessel via a PDMS aeration membrane. Each strain is introduced into 18 individual microfermentors using access channels. This allows 3 cultures to be terminated at each of 6 time points for each strain. The microfermentor array is maintained in a chamber as described in Example 3, which controls temperature and humidity. Biomass and dissolved oxygen concentration are monitored during the culture period, and data is accumulated using an appropriate software program. After an appropriate culture period (12, 24, 48, 72, 96, or 120 hours), all medium is removed from each microfermentor to be terminated at that time point and analyzed by HPLC to screen for a strain having the ability to produce xylitol.

Example 7

Strain Characterization and Process Parameter Optimization Using a Microscale Bioreactor Array (1) Measurement of Acid Production and Cell Growth with Various Carbon Sources Xylitol producing strains identified as in Example 6 are each cultured in individual microfermentors in a medium containing one of various carbon sources (1%), and presence of formed acid is determined. The following carbon sources are tested: xylose, arabinose, glucose, galactose, mannose, fructose, sorbase, sucrose, maltose, rhamnose, glycerol, mannitol, sorbitol, lactose, starch, and ethanol. The strains are pre-cultured in flasks in YPG medium at 28° C. for one day and then washed with 0.5% yeast extract solution. Since 5 strains and 16 carbon sources are tested, there is a total of 80 combinations.

Thirty microfermentors in a microfermentor array are inoculated with cells in YPC medium for each strain/carbon source combination, making a total of 2400 microfermentors. This allows 10 cultures to be terminated at each of 3 time points for each strain. (YPC is medium containing 0.5% yeast extract (Difco), and 1% of one of the various carbon sources sterilized by heating at 120° C. for 20 minutes prior to addition of the sterile carbon source. Depending on the particular pH sensor, the medium may contain a pH-sensitive dye such as bromocresol purple. The microfermentors have a working volume of 5 µl and are equipped with means to optically monitor biomass, oxygen concentration, and pH. Each microfermentor delivers oxygen to the interior of the microfermentor vessel via a PDMS aeration membrane.

The microfermentor array is maintained in a chamber as described in Example 3, which controls temperature and humidity. Biomass, dissolved oxygen concentration, and pH are monitored during the culture period, and data is accumulated using an appropriate software program. Cultures are maintained at 28° C. for 4, 5, or 6 days. After an appropriate culture period, all medium is removed from each microfermentor to be terminated at that time point and analyzed by HPLC to determine the amount of xylitol produced. The data can be used to select an appropriate strain and culture medium for a production scale fermentation process for the production of xylitol.

(2) Effect of NaCl, Acetic Acid or Ethanol Addition on Growth

Xylitol producing strains identified as in Example 6 are each cultured in individual microfermentors in YPM medium containing NaCl, ethanol, and/or acetic acid at a range of concentrations to determine the effect of these additives, singly or in combination, on growth. The xylitol producing strains and *Acetobacter aceti* strain NCIB 8621 as a control are pre-incubated in YPG medium (1% yeast extract (Difco), 1% peptone, sterilized by heating at 120° C. for 20 minutes, followed by addition of D-glucose to 7%) at 28° C. for one day, washed, and resuspended into medium with the one or more of the various additives at a range of concentrations. For each additive, 5 different concentrations are tested.

Thirty microfermentors are inoculated for each additive/concentration combination, allowing identical 10 cultures to be terminated at each of 3 time points. The microfermentors have a working volume of 5 µl and are equipped with means to optically monitor biomass, oxygen concentration, and pH. Each microfermentor delivers oxygen to the interior of the microfermentor vessel via a PDMS aeration membrane. The microfermentors are maintained in a chamber as described in Example 3, which controls temperature and humidity. Biomass, dissolved oxygen concentration, and pH are monitored during the culture period, and data is accumulated using an appropriate software program. Cultures are maintained at 28° C. for 4, 5, or 6 days. After an appropriate culture period, all medium is removed from each microfermentor to be terminated at that time point and analyzed by HPLC to determine the amount of xylitol produced. The data can be used to select an optimum strain and culture medium for a production scale fermentation process for the production of xylitol.

Example 8

Monitoring Multiple Bioprocess Parameters In a Microbioreactor

This example presents further experiments that were performed using microfermentors such as those described in Example 1. The microfermentors contained integrated sensors for on-line measurement of optical density (OD), dissolved oxygen (DO), and pH. All three parameter measurements were based on optical methods. Optical density was monitored via transmittance measurements through the microbioreactor well, while dissolved oxygen and pH were measured using fluorescence lifetime-based sensors incorporated into the body of the microbioreactor. Bacterial fermentations carried out in the microbioreactor under well-defined conditions were compared to results obtained in a 500 ml bench-scale bioreactor. It is shown that the behavior of the bacteria in the microbioreactor was similar to that in the larger bioreactor. This similarity includes growth kinetics, dissolved oxygen profile within the vessel over time, pH profile over time, final number of cells, and cell morphology. Off-line analysis of the medium to examine organic acid production and substrate utilization was performed. By changing the gaseous environmental conditions, it was demonstrated that oxygen levels within the microbioreactor can be manipulated. Furthermore, it was demonstrated that the sensitivity and reproducibility of the microbioreactor system are such that statistically significant differences in the time evolution of the OD, DO, and pH can be used to distinguish between different physiological states.

Materials and Methods

Microreactor Fabrication

Figure 42:
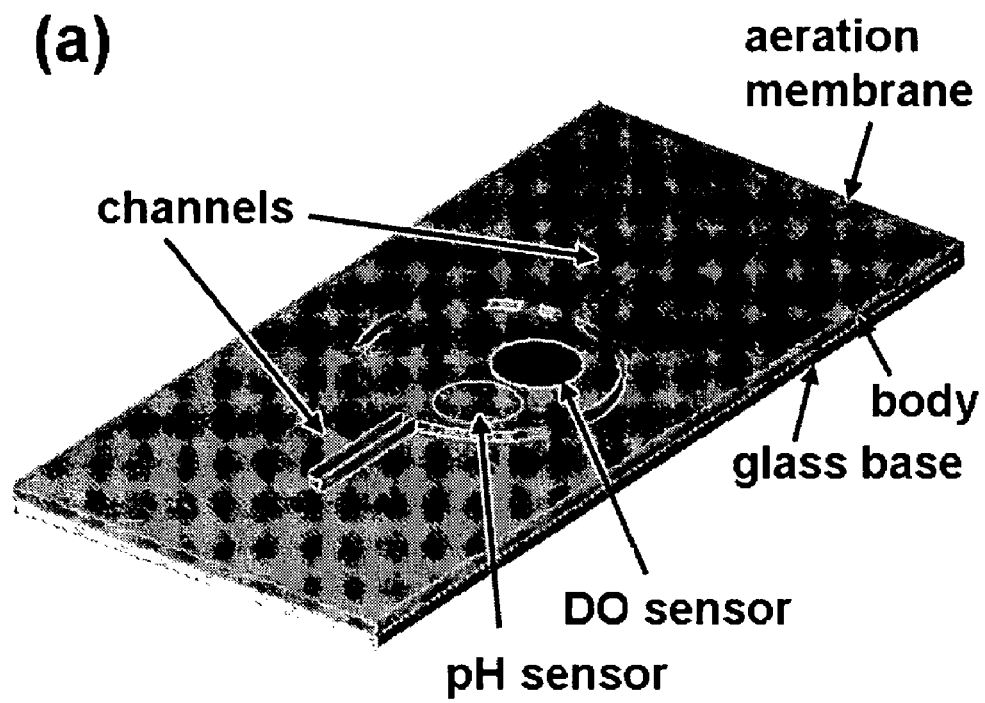
FIGS. 42A and 42B shows a microbioreactor of the invention.
Figure 42:
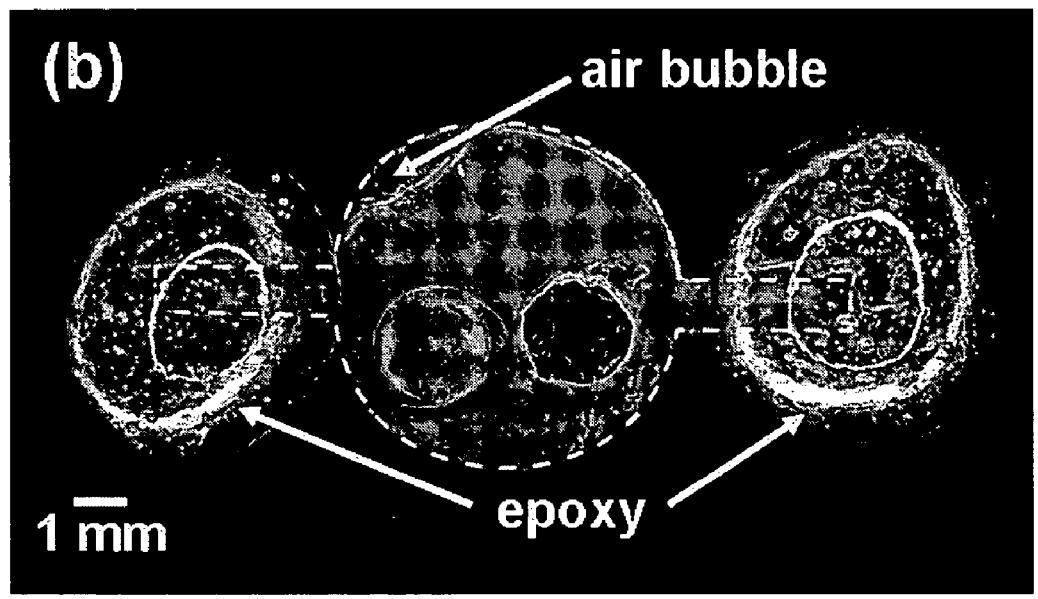

Microfermentors were fabricated out of poly(dimethylsiloxane) (PDMS) and glass essentially as described in Example I and elsewhere herein. PDMS was used for the body of the fermentor, the bottom layer into which the sensors were sunk, and the aeration membrane. This polymer was selected for its biocompatibility, optical transparency in the visible range, and high permeability to gases (including oxygen and carbon dioxide) as mentioned above (Merkel et al. 2000). The base support of the bioreactor was made of glass, which provided desirable rigidity as well as optical access. The typical volume of the microbioreactor was 5-50 µl, depending on the diameter used. The surface area-to-volume ratio was kept constant to ensure adequate oxygenation. The depth of the well was 300 µm, and the thickness of the aeration membrane was 100 µm. Of the experiments discussed below, those using complex medium were carried out in a volume of 5 µl, while those using defined medium were carried out in a volume of 50 µl to allow for off-line analysis of the medium. FIG. 42A shows a schematic perspective diagram of a microfermentor with integrated sensors mounted on a glass substrate.

Three PDMS layers were obtained by spincoating PDMS (Sylgard 184 Silicone Elastomer Kit, Dow Corning) onto silanized silicon wafers to the required thickness. The PDMS was then cured for two hours at 70° C., and the appropriate shapes were cut out of each layer. The bottom layer was 280 pm thick and contained two round holes into which two sensor foils were inserted, one for dissolved oxygen and one for pH as described in the following section. Each sensor was 2 mm in diameter and 150-220 µm in height. The sensors were held in place with silicone vacuum grease. Recessing the foils in this way allowed the tops to be flush with the bottom of the microbioreactor, which is especially critical for the dissolved oxygen foil as a result of the oxygen gradient that develops in the medium during fermentations (see Results). The 300 µm middle layer, which made up the body of the microbioreactor, consisted of a round opening of the desired diameter and channels for inoculation. The top layer was the 100 µm polymer aeration membrane. These layers were attached to each other and to the glass using an aquarium-grade silicone adhesive (ASI 502, American Sealants, Inc.) and allowed to cure overnight.

Optical Methods

Optical density, calculated from a transmission measurement at 600 nm, was used to monitor biomass. Light from an orange LED (Epitex L600-10V, 600 nm) was passed through the microbioreactor, collected by a collimating lens (F230SMA-A, Thorlabs), and sent to a photodetector (PDA55, Thorlabs). The optical density was calculated using the equation below, as described elsewhere herein:

$$OD = 33.33 \log_{10}\left(\frac{I_{reference}}{I_{signal}}\right)$$

In this equation $I_{signal}$ is the intensity of the signal and $I_{reference}$ is the intensity of the first measurement for a given experiment. Intensity readings were corrected for intensity fluctuations of the light source using a reference signal. The multiplication factor of 33.33 is a normalization for the pathlength of 300 µm in the microbioreactor which enables direct comparisons with results from conventional cuvettes with pathlengths of 1 cm. This adjustment is only strictly valid if the absorption and light scattering by the cell culture are in the linear region. Calibration data from the microbioreactor using known concentrations of E. coli show that the measurements are within the linear region, i.e. before saturation is reached. It is important to note that this measurement is very sensitive to both the path length and to any curvature of the PDMS aeration membrane.

Fluorescence from oxygen- and pH-sensitive dyes was selected for the measurement of dissolved oxygen (Bacon and Demas 1987; Klimant and Wolfbeis 1995; Demas et al. 1999) and pH, (Kosch et al. 1998; Lin 2000) respectively, because of the high sensitivity and specificity of this measurement (Demas and DeGraff 1991). The fluorescence of these dyes could be monitored using either fluorescence intensity or fluorescence lifetime measurements (Lakowicz 1999). There are several major advantages to using lifetime measurements. They are insensitive to background light, fluctuations of the excitation source and photodetector, changes in distance from the excitation source, bending of optical fibers, changes in medium turbidity, leaching of the indicator, and displacement of the sensing layer relative to the measurement setup.

Both dissolved oxygen and pH were monitored by phase-modulation lifetime fluorimetry using commercially available sensor foils from PreSens Precision Sensing GmbH (Regensburg, Germany). Dissolved oxygen was measured using a PSt3 sensor foil, while pH was measured using an HP2A sensor foil.

FIG. 14 shows the experimental setup. Bifurcated optical fibers (custom-made, Romack) connected to LEDs and photodetectors led into the chamber from both the top and bottom. As described above, a transmission measurement was used to calculate the optical density. The DO and pH sensors were excited with a square-wave modulated blue-green LED (NSPE590S, Nichia, 505 nm) and a blue LED (NSPB500S, Nichia, 465 nm), respectively. Exciter bandpass filters (XF1016 and XF 1014, Omega Optical) and emission long-pass filters (XF 3016 and XF 3018, Omega Optical) separated the respective excitation and emission signals and minimized cross-excitation. Data switches (8037, Electro Standards Laboratories) multiplexed the output signal and the input signal of the function generator (33120A, Agilent Technologies) and the lock-in amplifier (SR830, Stanford Research Systems), respectively. The lock-in amplifier measured and output the phase shift, which is directly related to the fluorescence lifetime, between the excitation and emission signals for the DO and pH measurement. All instruments were PC-controlled under a LabVIEW software routine, which allowed for automated and on-line measurement of the three parameters OD, DO, and pH. Readings of these parameters were taken every 10 minutes.

To determine the dissolved oxygen, the measured phase shift of the oxygen signal was related to the oxygen concentration using a modified Stem-Volmer equation (Carraway et al. 1991; Demas et al. 1995). An eleven-point calibration between 0% and 100% oxygen was carried out to confirm the validity of the equation and to calculate a Stem-Volmer constant. It was found that a better fit was obtained for low oxygen concentrations when the calibration range included in the model fit was limited to 0-21 % oxygen. Therefore, data from experiments with air as the contacting gas were processed using that range, while data from experiments using pure oxygen were processed using the full range of calibration.

The measured phase shift of the pH sensor fluorescence was related to the pH by fitting to the sigmoidal Boltzmann curve (Liebsch et al. 2001). A six-point calibration was carried out between pH 4 and pH 9 using colorless buffers (VWR).

Microbioreactor Experimental Setup

Experiments were carried out in an airtight, aluminum chamber (see FIG. 14). The chamber provided a means for controlling the humidity and the composition of the gas above the microbioreactor membrane. It also provided a large thermal mass for holding the temperature at the desired set point. The interior of the chamber had an area of 11.5 cm by 6.5 cm, and a height of 2.5 cm. This volume was large compared to the volume of the microbioreactor to ensure that gaseous oxygen was in large excess compared to the oxygen consumed by the cells during a fermentation. As a result, the chamber could be sealed for the duration of a run once it had been flushed with the desired gas. Temperature was controlled with a water bath that flowed water at the desired setpoint through the chamber base. Temperature was monitored using a thermocouple.

In addition to controlling environmental parameters, the chamber provided optical isolation and optical access for the desired measurements. Optical access was from the top and bottom of the chamber, directly above and below the microbioreactor, respectively, as shown in FIG. 14.

Biological Methodology

Organism and Medium

*Escherichia coli* FB21591 (thiC::Tn5 -pKD46, Kan$^R$) was used in all experiments and purchased from the University of Wisconsin. Stock cultures were maintained at −80° C. in 20% (vol/vol) glycerol. Prior to fermentation experiments, single colonies were prepared by streaking out the frozen cell suspension onto LB plates containing 2% (wt/vol) agar and 100 µg/ml of kanamycin. These plates were incubated overnight at 37° C. to obtain single colonies, and subsequently stored in the refrigerator at 4° C. for up to a week or used immediately to inoculate precultures.

Luria-Bertani medium was composed of 10 g/l tryptone (Difco Laboratories), 5 g/l yeast extract (Difco Laboratories), and 5 g/l NaCl. The solution was autoclaved for 40 minutes at 120° C. and 150 kPa. The LB medium was supplemented with 10 g/l glucose (Mallinckrodt), 100 mM MES buffer at pH 6.9 (2-(N-Morpholino)-ethanesulfonic acid)) (Sigma), and 100 µg/ml of kanamycin (Sigma). The glucose stock solution was autoclaved for 20 minutes at 120° C. and 150 kPa, and the MES and kanamycin stock solutions were filtered through 0.2 µm filters (Millipore).

The defined medium had the following composition: $K_2HPO_4$ [60 mM], $NaH_2PO_4$ [35 mM], $(NH_4)_2SO_4$ [15 mM], $NH_4Cl$ [70 mM], $MgSO_4 \cdot 7H_2O$ [0.8 mM], $Ca(NO_3)_2 \cdot 4H_2O$ [0.06 mM], $FeCl_3$ [20 mM], MES [100 mM], glucose [10 g/l], thiamine [100 µM], kanamycin [100 µg/ml], $(NH_4)_6Mo_7O_{24} \cdot 4H_2O$ [0.003 µM], $H_3BO_3$ [0.4 µM], $CuSO_4 \cdot 5H_2O$ [0.01 µM], $MnCl_2 \cdot 4H_2O$ [0.08 µM], $ZnSO_4 \cdot 7H_2O$ [0.01 µM]. Glucose, MES, kanamycin, and thiamine were added to the medium as stock solutions.

Precultures

For experiments using LB medium, 5 ml of sterile medium were transferred into test tubes and each was inoculated with a single colony of *E. coli* FB21591 from a LB-kanamycin agar plate. These cultures were incubated on a roller at 60 rpms and 37° C. Samples were removed periodically and measured for optical density (600 nm). When the optical density of the cultures reached OD=1±0.1, medium was removed from each test tube and transferred to a 500 ml baffled shake flask containing 30 ml of fresh medium to a starting optical density of 0.05. The inoculated shake flasks were incubated on shakers (150-200 rpm) at 37° C. Samples were withdrawn periodically until the optical density within the flasks reached OD=1. At this point the culture was used to inoculate either the bench-scale bioreactors or a microbioreactor.

Precultures for experiments using defined medium were carried out as above, except that the shake flasks into which the cultures from the test tubes were transferred contained defined medium.

Bench-scale Bioreactor

Batch cultures were grown in 500 mt SixFors bioreactors (Infors, Switzerland) with a starting medium volume of 450 mt. Dissolved oxygen probes (405 DPAS-SC-K8S/200, Mettler Toledo) were calibrated with nitrogen gas (0% DO) and air (100% DO) prior to each run. pH probes (InPro 6100/220/S/N, Mettler Toledo) were calibrated with buffer at pH 7.0 and 4.0 (VWR).

The bioreactors were inoculated to a starting optical density of 0.05. The aeration rate of gas was set to 1 VVM (volume of gas per volume of medium per minute) and the impeller speed was set to 500 rpm. This combination of stirring and sparging was selected to match the estimated $k_La$ of the microbioreactor. The $k_La$ was measured using the well-known method of "dynamic gassing out" (Van Suijdam et al. 1978). The temperature of the vessels was maintained at 37° C. for all fermentations. Dissolved oxygen and pH were not controlled, so as to simulate the batch microbioreactor. The time courses of temperature, dissolved oxygen, and pH were recorded every 10 minutes throughout all fermentations. Biomass was monitored by removing samples from the bioreactor at defined time intervals and measuring the optical density at 600 nm on a spectrophotometer (Spectronic 20 Genesys, Spectronic Instruments).

Microbioreactor

Inoculation of the medium for the microbioreactor was carried out outside of the bioreactor. Ten milliliters of fresh medium were transferred to a Falcon conical tube, and to this was added the preculture medium from a shake flask for a starting optical density of 0.05. This inoculated medium was then introduced into the microbioreactor by injecting the liquid via channels (FIG. 42A and 42B).

Sterility was maintained through the use of the antibiotic kanamycin in the medium. Other methods of sterilizing, such as autoclaving and UV radiation, were not feasible due to the incompatibility of either the DO sensor or the pH sensor with each of these methods. Gamma radiation was tested as an alternative technique. Ethanol could also be used as a means of sterilization. However, for the present studies we found that using a fast-growing, antibiotic-resistant strain was sufficient for preventing contamination.

To ensure the flatness of the PDMS membrane, excess liquid was squeezed out of the chamber by applying a uniformly distributed pressure from the top. A bulge in the membrane would change the path length for the calculation of optical density, as well as change the distance over which diffusion of oxygen occurred, thus changing the mass transfer characteristics of the microbioreactor. After injection of the inoculated medium, the needle holes created in the channels were sealed with epoxy (FIG. 42B). This was to prevent evaporation at these injection sites. Although PDMS selfseals to a large extent, we have noticed that needle holes increase the rate of evaporation and provide sites for the growth of air bubbles.

Once the microbioreactor was filled with medium it was placed inside the chamber and secured to the base. Open reservoirs of water were placed inside the chamber to provide humidity. Keeping the atmosphere within the chamber at high humidity minimizes evaporative losses through the PDMS membrane. The chamber was then closed and continuous readings were started. When fermentations were performed with pure oxygen in the chamber headspace, oxygen was passed through the chamber prior to the start of the readings.

The time between inoculation of fresh medium and placement of the filled microbioreactor in the chamber was 20 minutes. During this time the medium was kept at room temperature to minimize cell growth. The time between placement of the bioreactor in the chamber and the first reading was 10 minutes. During this time the bioreactor and cells warmed up to 37° C.

Cell Counts

Estimates of cell number from the microbioreactor and the bench-scale bioreactor were obtained using two methods. Direct cell counts were carried out using a Petroff-Hausser counting chamber and standard counting methodology. Viable cell counts were carried out using the technique of plating serial dilutions (Ausubel et al. 1995).

Medium Analysis

A series of experiments in defined medium was carried out to provide samples for off-line analysis of organic acids and glucose in both the bench-scale bioreactor and the microbioreactor.

During fermentations in the bench-scale bioreactors, samples of the medium were periodically removed, filtered, and frozen for later analysis.

Samples from the microbioreactors were obtained by sacrificing their entire volume. In order to obtain a sufficient volume of medium for analysis, the microbioreactors were fabricated to contain a volume of 50 µl. This allowed for volume loss during filtering and transfers, and provided sufficient filtered volume to meet the requirements of the HPLC protocol (5 µl). The medium samples were collected over several days. Each day three microbioreactors were inoculated and allowed to run in parallel while process parameters were measured. All three were then sacrificed at a predetermined time, and their contents were removed, filtered, and frozen. In this way, microbioreactor data was obtained at five time points. An Agilent 1100 Series HPLC equipped with an organic acid analysis column (Aminex HPX-87H Ion Exclusion Column, Bio Rad) was used for off-line medium analysis. Samples were prepared by filtration through a 0.2 µm membrane (Pall Gelman Laboratory). Calibration was carried out by running standards at two concentrations for each of the organic acids assayed, and four different standards for glucose. A linear fit through the origin was obtained for all of the concentration ranges used.

Results

To allow the comparison of results obtained with the microbioreactor and the bench-scale reactor, a $k_L a$ was measured in the microbioreactor and the operating conditions of the larger bioreactor were set so that its $k_L a$ would be comparable. The calculation of the $k_L a$ in the microbioreactor was based on a kinetic experiment (at 37° C.) in which the medium was allowed to come to equilibrium with nitrogen (0% DO) in the chamber headspace, at which time the headspace was flushed with air (100% DO) and continuous readings of the dissolved oxygen at the bottom of the microbioreactor were taken. Except for the absence of active stirring, this technique is similar to that of the dynamic "gassing-out" method that is commonly used for stirred bioreactors, during which the $k_L a$ is extracted as a first-order rate constant using the equation below. The technique has previously been used to find the $k_L a$ of a stagnant system (Randers-Eichhorn et al. 1996).

$$\frac{dC}{dt} = k_L a(C* - C)$$

The first-order approximation of the above equation is applicable if mass transfer is slow relative to the response time of the sensor. If the time response of the sensor is potentially significant relative to that of the entire system, a second order fit can be used as in the following equation, where $\tau_1$ is the time constant of the sensor and $\tau_2$ is the time constant of mass transfer.

$$C(t) = 100\left(1 - \frac{\tau_1 e^{\frac{-t}{\tau_1}} - \tau_2 e^{\frac{-t}{\tau_2}}}{\tau_1 - \tau_2}\right)$$

Experimentally we found the time constant of our sensor to be ~5 s. When response curves of our system were fit to the above equation we calculated an average $k_L a$ of ~60 h$^{-1}$. This is within the range of values measured in shake flasks (Maier and Buchs 2001; Gupta and Rao 2003; Wittmann et al. 2003) and shaken microtiter plates (Hermann et al. 2003; John et al. 2003b).

Experiments in defined medium were carried out in both the microbioreactors and the bench-scale bioreactors. MES buffer was added to provide some stabilization for the pH, since pH control was not implemented. The objectives were to establish the reproducibility of the microbioreactor relative to the bench-scale, and to demonstrate the feasibility of time-point sacrificing of the microbioreactors in order to carry out off-line analysis of the bioreactor medium throughout a fermentation. Three microbioreactors were sacrificed at each time point, and the medium was analyzed for glucose consumption and mixed-acid fermentation products using HPLC. In basic research or scale-up applications, this type of analysis would be desirable if an in situ sensor was not available for an analyte of interest.

Figure 43:
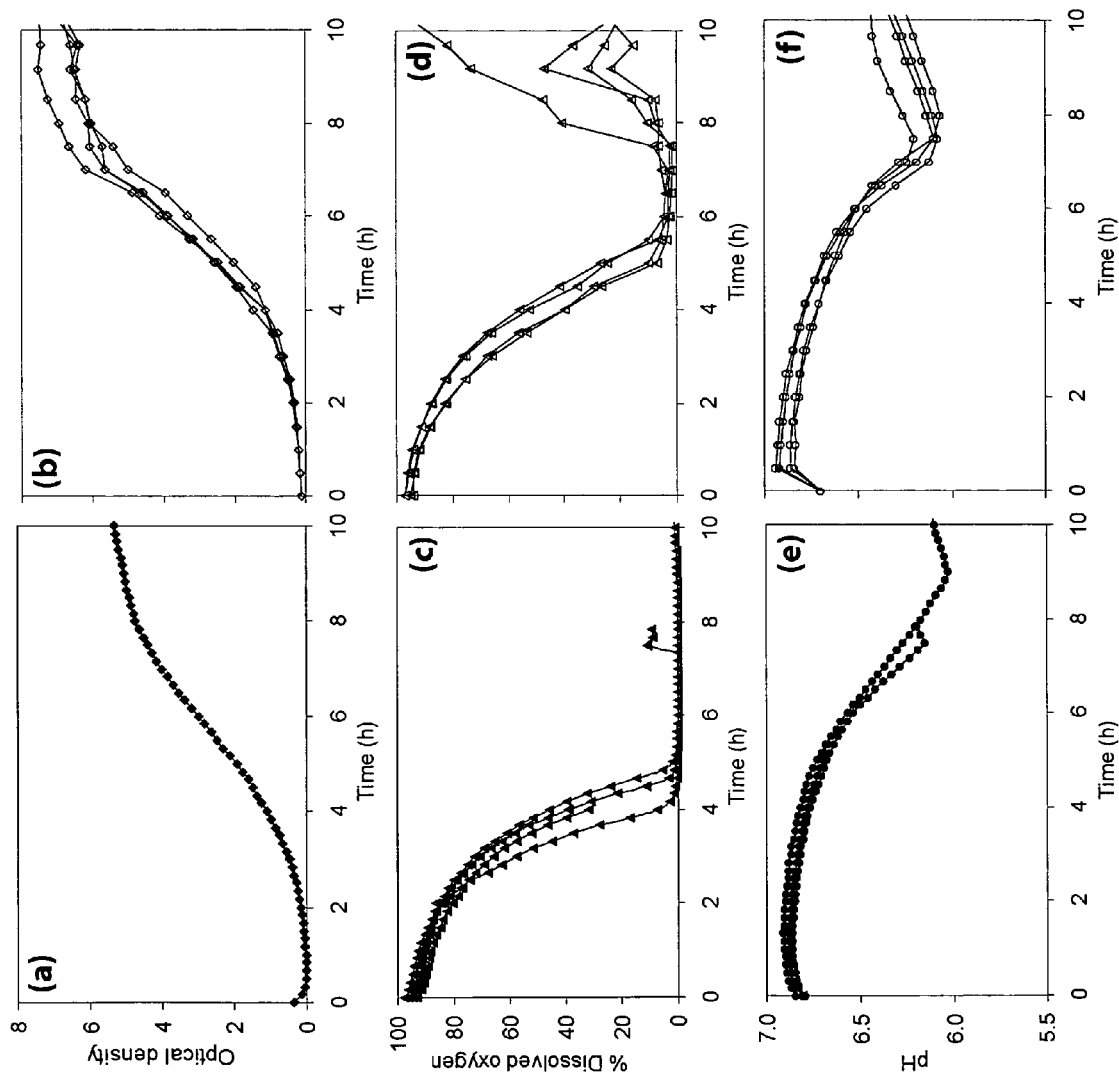
FIGS. 43A-43F are graphs showing values for bioprocess parameters monitored over time in microbioreactors and bench-scale bioreactors.

The three measured parameters within the microbioreactor and the bench-scale bioreactor are shown in FIG. 43. Each curve represents a separate run. A comparison of FIG. 43A (microbioreactors) and FIG. 43B (bench-scale bioreactors) shows that the optical density in both bioreactor types displays a similar trend, and results in a similar final OD of ~6.

FIG. 43C and FIG. 43D show the dissolved oxygen as a function of time in the microbioreactor and the bench-scale bioreactor, respectively. Again, it can be seen that the trend in both bioreactors is similar—even though the Sixfors chambers are mixed. This result is consistent with the similar values of oxygen mass transfer ($k_L a$) for the two systems. Oxygen levels deplete during the exponential growth of cultures and eventually recover as the bacteria reach stationary phase. Because of the presence of an oxygen gradient within the vessel (as determined experimentally and from modeling), the height of the dissolved oxygen sensor foil can affect the accuracy of the measurements obtained. If the sensor is raised above the height of the microbioreactor bottom or is somehow at an angle, it will take longer to be reached by the zero-dissolved-oxygen zone during depletion, and will register dissolved oxygen earlier during reoxygenation of the medium. Depending on its height, it may never show oxygen depletion. Thus it is desirable to position the oxygen sensor such that its entire surface is exposed to the same oxygen concentration. In this case the gradient is perpendicular to the bottom of the fermentor, and the foil must then be positioned horizontally (i.e. along the bottom of the chamber), rather than on the side where readings could be ambiguous.

The variation in the microbioreactor runs appears slightly larger than in the bench-scale bioreactor runs. We believe this is most likely due to the sensitivity of the oxygen measurements in the microbioreactor to the positioning of the dissolved oxygen foil. Specifically, if any or all of the DO foil is raised above the floor of the microbioreactor, the time to depletion and the time at depletion will change due to the oxygen gradient that exists within the medium.

The trends for pH variations over time within both bioreactor types are again very similar (FIGS. 43E and 43F). It appears that this measurement exhibits less variation between runs in the microbioreactor than the DO measurement. This is most likely due to the insensitivity of the pH measurement to the positioning of the pH sensor, suggesting that a pH gradient does not exist within the microbioreactor and the bioreactor can be considered well-mixed with respect to protons.

This was confirmed experimentally by placing the pH sensor at the top of the chamber during a fermentation run. The pH curve showed the same time profile as those from fermentations in which the sensor was at the bottom. This result is consistent with the analysis of the reaction and diffusion times within the microbioreactor.

When bacteria were viewed at the end of fermentation runs, the morphology of all cultures looked normal, with no stress-induced elongation visible. Final direct cell counts in both bioreactor types were carried out, and the concentration of cells in each was found to be on the order of $10^9$ cells/ml. It is difficult to get an exact count using this method, since the depth of field on the microscope is less than the 0.02 mm depth of the counting chamber, and the small size of the bacteria results in individual cells coming in and out of focus as the focus is adjusted. However, the estimate is consistent with the numbers obtained from viable cell counts, which yielded counts of 1-4×$10^9$ CFU/ml in both sizes of bioreactor.

Figure 44:
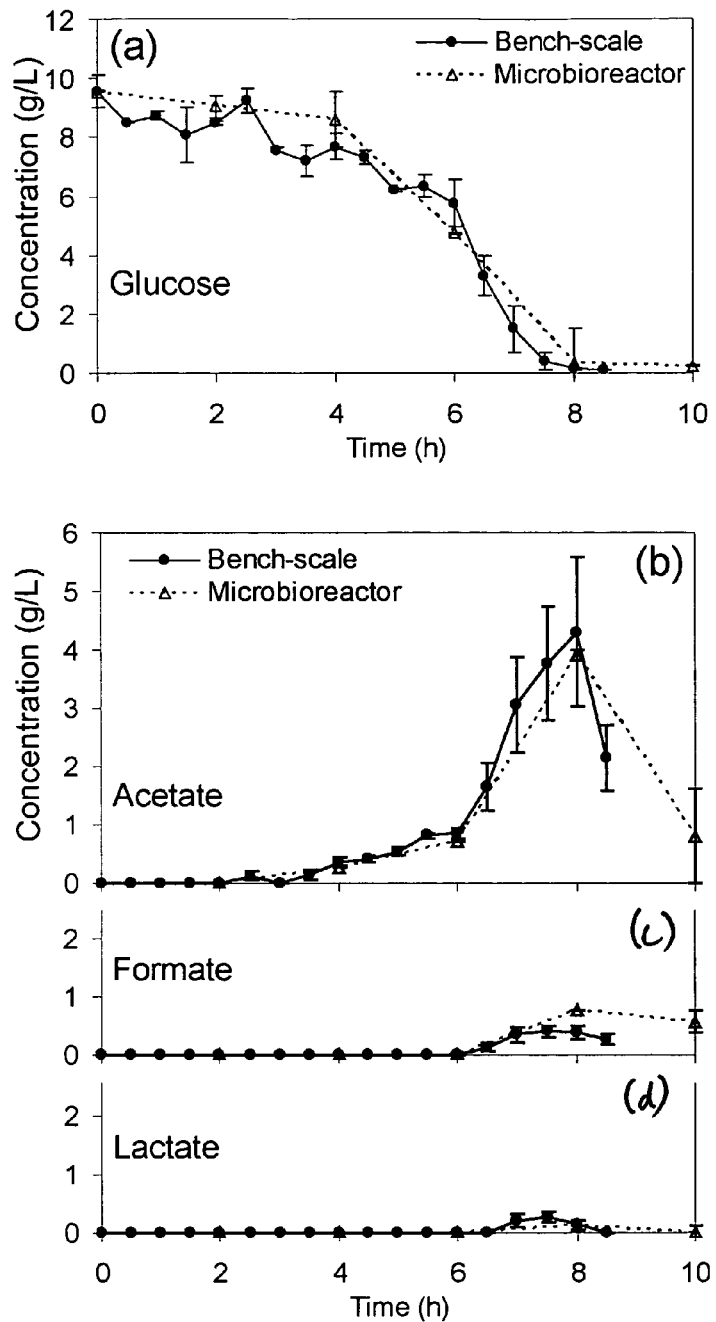
FIGS. 44A-44D are graphs showing values for concentration of glucose (FIG. 44A), acetate (FIG. 44B), formate (FIG.

FIG. 44 shows concentration curves for the analytes measured using HPLC. The glucose uptake in the microbioreactor (FIG. 44A) corresponds closely with that in the larger bioreactor. Additionally, FIGS. 44B-44D shows that concentrations of the E. coli mixed-acid fermentation products acetate, formate, and lactate show similar trends in both bioreactor systems (succinate was not found in either bioreactor type). Acetate in particular is produced in significant amounts as the fermentation proceeds.

Fermentations with Pure Oxygen

Additional experiments were carried out in LB medium, with air as well as 100% oxygen in the headspace of the chamber (above the aeration membrane) to determine whether a difference could be observed in bacterial growth characteristics. Supplying a partial pressure of 1 atm of oxygen above the microbioreactor instead of the 0.21 atm found in air leads to an approximately five-fold increase in the solubility of oxygen in the medium, as defined by Henry's law. This approach is commonly used in large-scale fermentations to avoid oxygen limitations. An extensive literature exists on the effects of total and partial oxygen pressure on microorganisms, including E. coli. (Brunker and Brown 1971; Gottlieb 1971; Konz et al. 1998). The general consensus appears to be that partial pressures of oxygen higher than those found in air are toxic to microorganisms and inhibit their growth, but that this effect is less pronounced in a robust organism such as E. coli. Growth inhibition has been noted in E. coli in the presence of pure oxygen when minimal medium is used. It is thought that the absence of $CO_2$ contributes to this inhibition (Onken and Liefke 1989). Although it is known that $CO_2$ can inhibit microbial growth, some $CO_2$ may be needed by a culture growing in minimal medium for the biosynthesis of essential compounds. In a complex medium these compounds may already be present. Alternatively, fermentation of substrates within the complex medium may provide sufficient $CO_2$ to meet the needs of the cells. In either case, the lack of $CO_2$ is not inhibitory. As a result, E. coli grown in complex medium under pure oxygen conditions does not seem to show inhibited growth. The focus of the present microbioreactor study was the effect of increased oxygen levels on E. coli growth.

In the presence of pure oxygen the initial maximum growth rate (FIG. 45A) does not appear to be different than the growth rate in the presence of air, but the bacteria are able to maintain it for a longer period of time. This is supported by the calculated doubling time in each case. With air in the headspace $t_d$=28 min ±3 min, and with oxygen in the headspace $t_d$=24 min±6 min. The overlapping error bars indicate that the difference in the mean is not statistically significant (at one standard error). The maximum optical density (and thus cell count) is somewhat higher when pure oxygen is used compared to air. As stationary phase progresses, however, the optical density of cells under pure oxygen decreases until the curve coincides with the air curve. This effect could possibly be attributed to higher rates of cell lysis under pure oxygen conditions.

When pure oxygen is contacted with the aeration membrane (FIG. 45B), the oxygen within the medium shows a minimum but never depletes entirely. The minimum oxygen level that the bacteria encounter is approximately 70%. This oxygen level is still three times higher than the maximum oxygen level with air as the contacting gas. In the case of the pH time course within the microbioreactor (FIG. 45C) the error bars, representing standard error, do not show overlap at any time point beyond the beginning of the fermentation. The curves show that the pH experiences a sharper drop in the presence of oxygen than in the presence of air. This is consistent with the higher growth observed in the OD curve in the presence of pure oxygen. Since the major source of protons in the medium comes from the protons that are excluded as ammonia (existing as $NH_4^+$ in the medium) crosses the cell membrane and is internalized as $NH_3$ (Bauer and Shiloach 1974), more growth would be expected to lead to a higher rate of proton generation, and subsequently a lower pH. At the end of fermentation runs with oxygen, bacteria exhibit normal morphology.

The results described above from the microbioreactor are reproducible in both complex medium (LB) and defined medium, and we are able to understand the oxygen transfer characteristics of the microbioreactor and effectively model growth and oxygen consumption of the bacteria during a fermentation. We have also shown that it is possible to sequentially sacrifice microbioreactors that are running in parallel to carry out off-line analysis using traditional techniques. Finally, we have shown that results obtained from the microbioreactor correspond closely with results obtained in bench-scale volumes.

Example 9

Design, Construction, and Operation of a Fed-Batch Microbioreactor with Active Stirring A microbioreactor that can be used for fed-batch fermentation was constructed from polymethylmethacrylate (PMMA) and PDMS. FIG. 25A shows an expanded view of the layer structure of the microbioreactor. FIG. 25B shows a longitudinal section of the microreactor with channels and integrated magnetic stirbar (described above). The stirbar is made of neodymium-iron. FIGS. 26A and 26B show photographs of the structure. The microbioreactor includes a round vessel (diameter 10 mm, depth 1 mm) and three connecting channels (depth 500 microns, width 500 microns) which are used for inoculation and reagent feeding. The vessel is formed by machining a well in a PMMA body layer. A thin layer of spin-coated PDMS covers the vessel and serves as an aeration membrane to supply oxygen to the vessel interior. This thin PDMS layer is held by a thicker PDMS layer to facilitate device assembly, sealing, and microfluidic connections. Another layer of PMMA forms the uppermost portion of the structure. Voids in the thicker PDMS and upper PMMA layers allow exposure of the PDMS membrane to the external environment. Two recesses (diameter 2 mm, depth 250 microns) at the bottom of the bioreactor chamber accommodate pH and DO fluorescence lifetime sensors. A 6 mm long magnetic stir bar in the vessel center mixes the fermentation medium. The stirbar rotates around a vertical post machined out of the bulk PMMA.

Fermentations were carried out in an incubator chamber kept at 37 degrees C. by flowing heated water through its base. One inlet channel connects the microbioreactor to an elevated water reservoir. FIG. 25C illustrates the principle of passive delivery of a liquid to the microreactor vessel. The pressure passively pumps liquid at the same rate as water evaporates through the thin PDMS layer, thus keeping the volume of the microbioreactor constant. The pumping rate can be adjusted by controlling the humidity in the incubator. The cell culture was operated as a batch process when water was fed into the microbioreactor, or as a fed-batch process when other solutions (e.g. glucose or base) were drawn into the microbioreactor by water evaporation (~μl/hr).

The incubator chamber was placed directly above a magnetic stirrer to minimize the distance to the spin bar in the microbioreactor (FIG. 31). In this set-up bifurcated optical fibers lead into the chamber from both the top and the bottom and are each connected to different LEDs and photodetectors. A transmission measurement using an orange LED (Epitex L600-10V, 600nm) returns the optical density. The DO and pH sensor patches are excited with a blue-green LED (Nichia NSPE590S, 505nm) and a blue LED (Nichia NSPB500S, 465nm) respectively. Exciter bandpass filter (Omega Optical XF1016 and XF1014) and emission longpass filters (Omega Optical XF 3016 and XF 3018) separate the respective excitation and emission signals and minimize cross-excitation. Data switches multiplex the output signal and the input signal of the function generator and the lock-in amplifier, respectively, as shown in FIG. 31. All instruments are PC-controlled under a LabView software routine, which allows for automated and on-line measurement of the parameters. For the results described herein, the three parameters were read every 10 minutes.

Microreactors containing optical sensors for DO and pH were inoculated with *E. coli* FB21591 in LB medium containing 8 g/L glucose, 100 ug/ml kanamycin, and 0.1 mol/L MES at an $OD_{600}$ of 0.05-0.07. Bioprocess parameters were monitored over time. FIGS. 46A and 46B shows results comparing operation of batch and fed-batch fermentation runs in a microreactor capable of operating in fed-batch mode. FIG. 46A is a graph showing dissolved oxygen concentration over time in a fed-batch fermentation in which the culture (*E. coli*) was supplied with 4 g/L glucose (dashed line) and in a batch fermentation in which the culture was supplied only with water (solid line). FIG. 46B is a graph showing pH over time in two fed-batch fermentations in which the cultures (E. coli) were supplied with 0.1 M NaOH (dot-dash line) or 0.01 M NaOH (dashed line) and in a batch fermentation in which the culture was supplied only with water (solid line).

For batch fermentation, the DO level drops rapidly to zero during exponential growth phase, when the multiplying cells have a strong demand for oxygen. As the cells enter the stationary phase, the oxygen demand drops and diffusion across the PDMS membrane returns the DO level to saturation. Addition of nutrient (glucose) appears to increase the length of the growth phase, slowing the return of the DO to saturation level.

The pH curves show a decrease to pH 5.6 in batch fermentation, which is reduced when a diluted base solution (0.01M NaOH) is fed. When a strong base solution (0.1M NaOH) is fed, pH decreases even less during cell growth phase and strongly increases thereafter. In the shown example, the strong base solution was administered 80 minutes after the fermentation run had started with cell growth in early phase.

These results demonstrate that the environmental conditions in microbioreactors can be monitored as in a batch process and manipulated in a fed-batch process. Moreover, if pH values are maintained close to neutral, cell density is expected to increase. Thus, the ability to feed base and nutrients makes this micro fed-batch system further confirms the utility of the method for screening applications in bioprocess engineering.

Example 10

Simultaneous Operation of Multiple Microbioreactors in a Microreactor Chamber This example provides further details of realized implementations and initial testing of an apparatus for simultaneous operation of a plurality of microreactors as described above in section III.A. A chamber designed to accommodate a microreactor tray capable of holding up to 8 microreactors was constructed out of aluminum using standard machining methods and equipment. Dimensions were 7.5in deep, 14.20in wide, Height without top lid: 7in. on the back wall. The top lid adds another 2 in approximately. Different heights were selected for the back and front walls to allow for convenient removal of the removable elements (e.g., microreactor tray). Thus the slide walls slope down from back to front and the lid is configured accordingly. The chamber was equipped with a stage with threaded rod and slider (Velmex, Bloomfield, N.Y.; part number MA2512K2-S2.5) to move an optics bracket, which was also constructed from aluminum using standard methods. A motor was connected via cables fed through the rear of the chamber. A VXM-1 Prog Controller was used to provide an interface to a computer for controlling operation of the motor. The sidewalls of the chamber were equipped with gas inlet ports to provide for control over gas concentration and, optionally, humidity within the chamber. A gasket was included at the top edge of the chamber. Temperature control was provided via a base plate that included a channel manifold to allow flow through of heated water. A thermocouple was provided on the microreactor tray for temperature measurement (New England Temperature Services). The back plate of the chamber contained slits to allow feed through of optical fibers, cables carrying electrical signals, thermocouple wires, etc.

Support structures in the form of posts with an approximately rectangular cross-section were machined from Delrin®. The posts contained depressions on the upper face to hold miniature electromagnetic stirrers (Variomag; Telesystem Mini HP 40 154). A Telemodul 40C controller (HP 90 450 U) equipped with an 8-point distributor box (HP 93 008) was used to interface with the computer. The support structures were fixed to an aluminum insert that can be screwed into the base of the chamber interior. Small flat panels containing holes on either side were attached to the back of the posts. Rods extended through the holes from the front of the chamber to a stopper bar that extended across the chamber on the opposite side of the posts. The rods were threaded through springs that extended from the panels to the front of the chamber. Motion of the optics bracket brings it into contact with the posts, forcing them toward the front of the chamber and compressing the springs. When the optics bracket moves out of the way, spring force restores the posts to their initial position. Movement of the posts allows the optics bracket to be appropriately positioned so that an optical fiber threaded through an aperture in the bracket either from above or below can come within millimeters of a microreactor mounted in a tray. The optics bracket and posts were appropriately contoured for smooth operation when in contact. FIG. 36 shows a photograph of the apparatus with the microreactor tray removed. FIG. 37 shows a photograph of the apparatus with a mounted microreactor tray. The support structures were removed to allow better visualization of the microreactor tray and transparent microreactor structures.

The aluminum insert also contained structural supports on which to place a microreactor tray. The supports had holes to allow the microreactor tray to be securely mounted yet easily removed. The microreactor trays themselves were machined out of aluminum. They contained either four or eight openings in a row that extended across the chamber, when mounted, parallel to the rod on which the optics bracket moves. Since the microreactor vessel (and substrate, if any) is transparent, measurements can be taken from above and/or below the microreactors. Optical fibers were used to transmit excitation light and detect emission and transmitted light as described in the example above. Control over operation of the system components was achieved through a computer running the LabVIEW software suite. FIG. 40B shows a screen shot illustrating the graphical user interface allowing parameters such as run name, length of total run, sampling interval, number of reactors, etc., to be set by the user.

To test the system, $E.$ $coli$ FB 21591 were cultured in LB medium as described in the previous example. Microreactors with a vessel volume of 80 ul containing optical sensors for DO and pH as described above and a magnetic stirbar for active mixing were inoculated with bacteria at an $OD_{600}$ of 0.05-0.07. The microreactors were attached via a channel to a reservoir containing water which was provided to the microreactor vessels using evaporative pumping as described above, at a rate such that evaporating water was replaced. The microreactors were mounted in the chamber, which was maintained at 37 degrees and optically monitored over time. FIGS. 47A-47C shows graphs of dissolved oxygen (DO), raw (uncorrected) optical density (OD), and pH for four microreactors operating in parallel in an apparatus of the invention. The results demonstrate the successful collection of values for three different bioprocess parameters in four microreactors operating simultaneously using a single optical excitation and detection system. The parameters were monitored in parallel over a culture period of 8 hours. The time courses obtained for microreactors R1, R2, and R4 resemble each other more closely than they resemble the time course for microreactor R3, with respect to each of the three parameters measured. While not wishing to be bound by any theory, this suggests that the culture in microreactor R3 differed from the others in a way that affected multiple bioprocess parameters. While these results are preliminary, the data confirm the utility of using the apparatus to select preferred cell strains, culture conditions, etc., by comparing bioprocess parameters among a plurality of cultures growing in parallel.

Example 11

Gene Expression Analysis on Cells Cultured in a Microbioreactor Using Microarrays DNA microarrays were utilized for a comparative gene expression analysis of $E.$ $coli$ FB21591 (purchased at the University of Wisconsin) grown in 50 ul batch-culture microbioreactors in either LB or Defined Medium (Table 6) without stirring. The microbioreactors were constructed of PDMS as described above (Example 1) and contained a PDMS oxygenation membrane. Microarrays utilized were purchased at the BioMicro Center at MIT and contained about 4,400 opening reading frames (ORFs). The ORFs, a set of 50 mer oligonucleotides, were purchased from MWJG-Biotech Inc (High Point, N.C.). The clones were spotted on Corning GAPS slides with a Biorobotics Microgrid Two printer. All kits used in the protocol described herein were used in accordance with the instructions of the manufacturer.

Cultures were inoculated at a starting $OD_{600}$ of 0.05 as described in Example 8 and were grown until they reached an $OD_{600}$ of about 1.0 (typically between about $8 \times 10^9$ and $10^9$ cells/ml culture fluid. Thus the total number of cells used was about 4-5 and $10^7$ cells. The cells reached $OD_{600}$~1 in 60-70 min when grown on LB medium and in 180-240 min when grown in Defined Medium. Total RNA was isolated from 3 independent culture fermentations grown in either LB or in Defined Medium (Table 6). FIGS. 48A and 48B show OD, DO and pH curves of E.coli grown in LB and Defined Medium in the 50 ul microbioreactors. Total RNA was isolated using a combination of enzymatic and mechanical cell disruption and Qiagen RNeasy columns. When $E.$ $coli$ cultures reached OD=1, the microbioreactor incubation chamber was opened, and the culture was immediately withdrawn from the microbioreactors with a 20-200 ul Pipetman. The culture was then transferred to two volumes of RNAprotect™ Bacteria (Qiagen) for RNA stabilization. After 5 minutes of incubation cells were precipitated by centrifugation and resuspended in 200 ul of TE containing 15mg/ml lysozyme. After 20 minutes of incubation cells were transferred in a 2 ml tubes containing 50 mg of acid washed 0.1 mm zirconia/silica beads (Biospec Products Inc. Bartesville, Okla.). Cells were then beaten in a FastPrep FP120 (Qbiogene, Inc. Calif.) for 1.5 min at maximum speed. Total RNA isolation then proceeded by following the Rneasy protocol. After isolation, total RNA concentration and purity was analyzed with an Agilent 2100 Bioanalyzer.

Microarray hybridizations were performed with the Qiagen Highlight Dual-Color Array Detection system which is based on Resonance Light Scattering (RLS) technology.

From each fermentation two pools of 500ng of total RNA were used to generate cDNA labeled with Biotin-16-dUTP or Fluorescin-12-dUTP (Roche, Indianapolis, Ind.) using the Qiagen LabelStar™ system.

We performed a total of 6 hybridizations comparing an LB versus a Defined Medium fermentation on a single array in triplicate and then we performed dye swap hybridizations of the same experiments. After cDNA hybridiazations microarrays were incubated with anti-biotin-gold (Highlight RLS particles Au) and anti-fluorescin-silver (Highlight RLS particles Ag) and archived. Spot intensities were obtained with a GSD-501 RLS detection and imaging scanner and the software MolecularWare.

From these experiments we found that 90 and 108 genes were upregulated when E.coli was grown in LB and Defined Medium respectively (Tables 7 and 8). Intensity data were normalized by the rank invariant lowess and genes were considered upregulated if the log10 ratio of Defined Medium intensity over LB intensity for each ORF was $\geqq 2$ (Tables 7 and 8). These experiments demonstrate the feasibility of performing gene expression analysis on large numbers of genes in cells cultured in microbioreactors. Future experiments utilizing the GeneChips™ system (Affymetrix, Santa Clara, Calif.) are planned in addition to experiments using actively stirred microbioreactors, and fed-batch and continuous microbioreactors such as those described above. Monitoring bioprocess parameters in conjunction with gene expression profiling will greatly expand the number of criteria that can be used in selecting optimal strains, culture conditions, etc.

TABLE 6

Media composition.

| Defined Medium | Substrate | Final Concentration |
| --- | --- | --- |
| | $K_2HPO_4$ | 60 mM |
| | $NaH_2PO_4$ | 35 mM |
| | $(NH_4)_2SO_4$ | 15 mM |
| | $NH_4Cl$ | 70 mM |
| | $MgSO_4 \cdot 7H_2O$ | 0.8 mM |
| | $Ca(NO_3)_2 \cdot 4H_2O$ | 0.06 mM |
| | $FeCl_3$ | 2 mM |
| | Glucose | 44 mM (0.8%) |
| | MES (2M) pH 6.9 | 0.1 M |
| | Thiamine (0.1 M) | 0.1 mM |
| | Kananycin (100 mg/ml) | 100 µg/ml |
| | Trace Minerals* | 1 ml/L | pH adjusted to 7.0 with NaOH

| Trace Minerals* | Substrate | Final Concentration |
| --- | --- | --- |
| | $(NH_4)_6Mo_7O_{24} \cdot 4H_2O$ | 0.003 µM |
| | $H_3BO_3$ | 0.4 µM |
| | $CaSO_4 \cdot 2H_2O$ | 0.01 µM |
| | $MnCl_2 \cdot 4H_2O$ | 0.08 µM |
| | $ZnSO_4 \cdot 7H_2O$ | 0.01 µM |

| LB Medium | Substrate | Composition/l |
| --- | --- | --- |
| | Bactotryptone | 10 g |
| | Yeast extract | 5 g |
| | Nacl | 5 g |
| | Glucose | 44 mM (0.8%) |
| | MES (2M) pH 6.9 | 0.1 M |

TABLE 7 upregulated genes in E. coli FB21591 growing in LB

| Gene ID | Gene product | Fold change[a] |
| --- | --- | --- |
| b1973 | orf, hypothetical protein | 5.3 |
| fliC | lagellar biosynthesis; flagellin, filament structural protein | 4.6 |
| motB | flagellar motor rotation, linking torque machinery to cell wall | 4.4 |
| ydaU | orf, hypothetical protein | 4.0 |
| flgC | flagellar biosynthesis, cell-proximal portion of basal-body rod | 3.5 |
| guaA | GMP synthetase (glutamine-hydrolyzing) | 3.5 |
| yfiA | putative yhbH sigma 54 modulator | 3.3 |
| flgE | flagellar biosynthesis, hook protein | 3.2 |
| srlA | PTS system, glucitol/sorbitol-specific IIC component | 3.2 |
| yejE | putative transport system permease protein | 3.1 |
| fliO-4 | replicated spot flagelar biosynthesis | 3.1 |
| ychF | putative GTP-binding protein | 3.1 |
| lexA | regulator for SOS(lexA) regulon | 3.1 |
| yedW | putative 2-component transcriptional regulator | 3.1 |
| gcvT | aminomethyltransferase of glycine cleavage system | 3.0 |
| malF | part of maltose permease, periplasmic | 3.0 |
| b2345 | orf, hypothetical protein | 2.9 |
| flgG | flagellar biosynthesis, cell-distal portion of basal-body rod | 2.9 |
| yehQ | orf, hypothetical protein | 2.9 |
| b1503 | putative fimbrial-like protein | 2.8 |
| fecA | outer membrane receptor; citrate-dependent iron transport | 2.8 |
| flgM | anti-FliA (anti-sigma) factor; also known as RflB protein | 2.8 |
| yeeS | putative DNA repair protein, RADC family | 2.8 |
| yqhH | orf, hypothetical protein | 2.7 |
| yafU | orf, hypothetical protein | 2.7 |
| fliA | flagellar biosynthesis; alternative sigma factor 28 | 2.7 |
| yeaD | orf, hypothetical protein | 2.7 |
| tar | methyl-accepting chemotaxis protein II | 2.7 |
| yjdA | putative vimentin | 2.7 |
| flgD | flagellar biosynthesis, initiation of hook assembly | 2.6 |
| gmhA | phosphoheptose isomerase | 2.6 |
| mopA | GroEL, chaperone Hsp60, peptide-dependent ATPase | 2.6 |
| cheW | positive regulator of CheA protein activity | 2.6 |
| ydgB | putative oxidoreductase | 2.5 |
| tdk | thymidine kinase | 2.5 |

TABLE 7-continued upregulated genes in *E. coli* FB21591 growing in LB

| Gene ID | Gene product | Fold change[a] |
|---|---|---|
| gcvP | glycine decarboxylase, P protein of glycine cleavage system | 2.5 |
| recN | protein used in recombination and DNA repair | 2.5 |
| ycjQ | putative oxidoreductase | 2.5 |
| purD | phosphoribosylglycinamide synthetase = GAR synthetase | 2.5 |
| alpA | prophage CP4-57 regulatory protein alpA | 2.5 |
| napG | ferredoxin-type protein: electron transfer | 2.5 |
| gcvH | glycine cleavage complex, carrier of aminomethyl moiety | 2.5 |
| b2247 | putative racemase | 2.5 |
| ybiP | putative enzyme | 2.5 |
| b2352 | putative ligase | 2.4 |
| yneB | orf, hypothetical protein | 2.4 |
| yeaJ | orf, hypothetical protein | 2.4 |
| ycfL | orf, hypothetical protein | 2.4 |
| flgK | flagellar biosynthesis, hook-filament junction protein 1 | 2.4 |
| lysU | lysine tRNA synthetase, inducible; heat shock protein | 2.3 |
| recA | DNA strand exchange and renaturation | 2.3 |
| rplR | 50 S ribosomal subunit protein L18 | 2.3 |
| b2291 | putative alpha helix protein | 2.3 |
| yeaH | orf, hypothetical protein | 2.3 |
| selD | selenophosphate synthase, H(2)Se added to acrylyl-tRNA | 2.3 |
| fliN | flagellar biosynthesis, component of motor | 2.3 |
| carB | carbamoyl-phosphate synthase large subunit | 2.3 |
| b1976 | orf, hypothetical protein" | 2.3 |
| fliD | flagellar biosynthesis; filament capping protein | 2.3 |
| flgA | flagellar biosynthesis | 2.2 |
| fdoG | formate dehydrogenase-O, major subunit | 2.2 |
| araH_A | partial high-affinity L-arabinose transport system | 2.2 |
| yhjH | orf, hypothetical protein" | 2.2 |
| cheY | chemotaxis regulator transmits chemoreceptor signals | 2.2 |
| b2506 | putative membrane protein | 2.2 |
| guaB | IMP dehydrogenase | 2.2 |
| metC | cystathionine beta-lyase (beta-cystathionase) | 2.2 |
| Ara23-9 | Arabidopsis Control Oligonucleotide | 2.2 |
| b4250 | orf, hypothetical protein | 2.1 |
| b2080 | orf, hypothetical protein | 2.1 |
| yqjB | orf, hypothetical protein | 2.1 |
| b1903 | orf, hypothetical protein | 2.1 |
| fliG | flagellar biosynthesis, component of motor | 2.1 |
| fecB | citrate-dependent iron transport, periplasmic protein | 2.1 |
| ygfG | putative enzyme | 2.1 |
| lar | restriction alleviation protein encoded by prophage CP-933R | 2.1 |
| clpP | ATP-dependent proteolytic subunit of clpA-clpP | 2.1 |
| fliS | flagellar biosynthesis | 2.0 |
| yecP | putative enzyme | 2.0 |
| tdh-r | threonine dehydrogenase | 2.0 |
| b1448 | putative resistance protein | 2.0 |
| yeeX | putative alpha helix protein | 2.0 |
| grpE | phage lambda replication; host DNA synthesis | 2.0 |
| yieE | orf, hypothetical protein" | 2.0 |
| caiF | transcriptional regulator of cai operon | 2.0 |
| rpA | helicase, ATP-dependent" | 2.0 |
| gpmA | phosphoglyceromutase 1 | 2.0 |
| elaA | orf, hypothetical protein | 2.0 |
| flgH | flagellar biosynthesis, basal-body outer-membrane L | 2.0 |
| yaiA | orf, hypothetical protein | 2.1 |
| yjfH | orf, hypothetical protein | 2.1 |
| b2083 | orf, hypothetical protein | 2.1 |
| dps | global regulator, starvation conditions | 2.1 |
| ycbP | NAD(P)H-dependent FMN reductase | 2.0 |
| hdeA | orf, hypothetical protein" | 2.0 |
| gadB | glutamate decarboxylase isozymes | 2.0 |
| pntA | pyridine nucleotide transhydrogenase, alpha subunit" | 2.0 |
| frdC | fumarate reductase, anaerobic, membrane anchor polypeptide" | 2.0 |
| stpA | DNA-binding protein; H—NS-like protein | 2.0 |
| tsf | protein chain elongation factor EF-Ts | 2.0 |
| b1674 | putative oxidoreductase, Fe—S subunit | 2.0 |
| uidB | glucuronide permease | 2.0 |
| yciR | orf, hypothetical protein | 2.0 |
| ilvN | acetolactate synthase I, valine sensitive, small subunit | 2.0 |
| ycdF | orf, hypothetical protein | 2.0 |

[a] Genes were considered differentially expressed when the log10 ratio was ≧2.

TABLE 8 upregulated genes in *E. coli* FB21591 growing in Defined Medium

| Gene ID | Gene product | Fold change[a] |
|---|---|---|
| yfjM | orf, hypothetical protein | 15.8 |
| b1978 | putative factor | 8.1 |
| proX | high-affinity transport system for glycine betaine and proline | 5.9 |
| leuC | 3-isopropylmalate isomerase (dehydratase) subunit | 5.5 |
| aceB | malate synthase A | 4.8 |
| otsA | trehalose-6-phosphate synthase | 4.7 |
| proV | ATP-binding component of transport system for glycine | 4.6 |
| none | orf; Unknown function; internal control | 4.5 |
| osmY | hyperosmotically inducible periplasmic protein | 4.4 |
| cspG | homolog of Salmonella cold shock protein | 4.3 |
| oppA | oligopeptide transport; periplasmic binding protein | 4.3 |
| nrfC | formate-dependent nitrite reductase; Fe—S centers | 4.2 |
| gatY | tagatose-bisphosphate aldolase 1 | 4.2 |
| yicM | putative transport protein | 4.0 |
| thrB | homoserine kinase | 3.8 |
| ybgD | putative fimbrial-like protein | 3.8 |
| aceA | isocitrate lyase | 3.7 |
| proW | high-affinity transport system for glycine betaine and proline | 3.6 |
| gatA | galactitol-specific enzyme IIA of phosphotransferase system | 3.6 |
| ompT | outer membrane protein 3b (a), protease VII | 3.5 |
| cysP | thiosulfate binding protein | 3.4 |
| thrC | threonine synthase | 3.4 |
| b1721 | orf, hypothetical protein | 3.3 |
| b1481 | orf, hypothetical protein | 3.3 |
| gltD | glutamate synthase, small subunit | 3.2 |
| spr | putative lipoprotein | 3.1 |
| gatZ | putative tagatose 6-phosphate kinase 1 | 3.1 |
| leuB | 3-isopropylmalate dehydrogenase | 3.1 |
| gltB | glutamate synthase, large subunit" | 3.1 |
| b2250 | orf, hypothetical protein | 3.0 |
| bax | putative ATP-binding protein | 3.0 |
| dppA | dipeptide transport protein | 3.0 |
| gapC_1 | glyceraldehyde 3-phosphate dehydrogenase C, interrupted | 2.9 |
| rpsV | 30 S ribosomal subunit protein S22 | 2.9 |
| osmE | activator of ntrL gene | 2.8 |
| ybdU | orf, hypothetical protein | 2.8 |
| b1643 | orf, hypothetical protein | 2.8 |
| ybhO | putative synthetase | 2.8 |
| b1372 | putative membrane protein | 2.8 |
| metE | tetrahydropteroyltriglutamate methyltransferase | 2.7 |
| trpC | N-(5-phosphoribosyl)anthranilate isomerase | 2.7 |
| b1374 | putative transposon resolvase; orf, hypothetical protein | 2.7 |
| none | hypothetical protein; internal control | 2.7 |
| sucC | succinyl-CoA synthetase, beta subunit | 2.6 |
| ycfJ | orf, hypothetical protein | 2.6 |
| b1506 | orf, hypothetical protein | 2.6 |
| b0235 | orf, hypothetical protein | 2.6 |
| gatY-r | tagatose-bisphosphate aldolase 1 | 2.6 |
| b1724 | orf, hypothetical protein" | 2.5 |
| gatC | PTS system galactitol-specific enzyme IIC | 2.5 |
| yrbL | orf, hypothetical protein | 2.5 |
| ivbL | ilvB operon leader peptide | 2.5 |
| ybiC | putative dehydrogenase | 2.5 |
| livJ | high-affinity amino acid transport system | 2.5 |
| yafP | orf, hypothetical protein | 2.4 |
| elaB | orf, hypothetical protein | 2.4 |
| dniR | transcriptional regulator for nitrite reductase (cytochrome c552) | 2.4 |
| trpC-r | N-(5-phosphoribosyl)anthranilate isomerase | 2.4 |
| hisF | imidazole glycerol phosphate synthase subunit | 2.4 |
| narG | nitrate reductase 1, alpha subunit | 2.4 |
| yecM | orf, hypothetical protein | 2.4 |
| aroF | 3-deoxy-D-arabinoheptulosonate-7-phosphate synthase | 2.4 |
| cysM | cysteine synthase B, O-acetylserine sulfhydrolase B | 2.4 |
| b2862 | orf, hypothetical protein | 2.3 |
| aroL | shikimate kinase II | 2.3 |
| osmB | osmotically inducible lipoprotein | 2.3 |
| rpoS | RNA polymerase, sigma S (sigma38) factor | 2.3 |
| yaeG | orf, hypothetical protein | 2.3 |
| ygaM | orf, hypothetical protein | 2.3 |
| slpA | probable FKBX-type 16 KD peptidyl-prolyl cis-trans isomerase | 2.3 |
| oppD | homolog of Salmonella ATP-binding ABC transport system | 2.3 |
| cysJ | sulfite reductase (NADPH), flavoprotein beta subunit | 2.2 |
| cmk | cytidylate kinase | 2.2 |
| yeaW | orf, hypothetical protein | 2.2 |
| narJ | nitrate reductase 1, delta subunit, assembly function | 2.2 |

TABLE 8-continued upregulated genes in *E. coli* FB21591 growing in Defined Medium

| Gene ID | Gene product | Fold change[a] |
|---|---|---|
| murG | UDP-N-acetylglucosamine: N-acetylmuramyl-(pentapeptide) | 2.2 |
| rplE | 50 S ribosomal subunit protein L5 | 2.2 |
| leuA | 2-isopropylmalate synthase | 2.2 |
| sdhA-r | succinate dehydrogenase, flavoprotein subunit | 2.2 |
| b2085 | orf, hypothetical protein | 2.2 |
| malT | positive regulator of mal regulon | 2.2 |
| b1588 | putative oxidoreductase, major subunit | 2.1 |
| wcaA | putative regulator | 2.1 |
| ychK | orf, hypothetical protein" | 2.1 |
| ybcZ | putative 2-component sensor protein | 2.1 |
| aroM | protein of aro operon, regulated by aroR | 2.1 |
| gapC_2 | glyceraldehyde-3-phosphate dehydrogenase (second fragment) | 2.1 |
| cspH | cold shock-like protein; cold shock protein | 2.1 |
| glgX | part of glycogen operon, a glycosyl hydrolase" | 2.1 |
| racC | defective prophage rac; contains recE and oriJ | 2.1 |
| yaiA | orf, hypothetical protein | 2.1 |
| yjfH | orf, hypothetical protein | 2.1 |
| b2083 | orf, hypothetical protein | 2.1 |
| dps | global regulator, starvation conditions | 2.1 |
| ycbP | NAD(P)H-dependent FMN reductase | 2.0 |
| hdeA | orf, hypothetical protein | 2.0 |
| gadB | glutamate decarboxylase isozymes | 2.0 |
| pntA | pyridine nucleotide transhydrogenase, alpha subunit | 2.0 |
| frdC | fumarate reductase, anaerobic, membrane anchor polypeptide" | 2.0 |
| stpA | DNA-binding protein; H—NS-like protein; | 2.0 |
| tsf | protein chain elongation factor EF-Ts | 2.0 |
| b1674 | putative oxidoreductase, Fe—S subunit | 2.0 |
| uidB | glucuronide permease | 2.0 |
| yciR | orf, hypothetical protein | 2.0 |
| ilvN | acetolactate synthase I, valine sensitive, small subunit | 2.0 |
| ycdF | orf, hypothetical protein | 2.0 |

[a]Genes were considered differentially expressed when the log10 ratio was $\geq 2$

REFERENCES

1. D. M. Disley, P. R. Morrill, K. Sproule, C. R. Lowe, "An optical biosensor for monitoring recombinant proteins in process media," 14, 481-493 (1999).
2. D. E. Cane, C. T. Walsh, C. Khosla, "Harnessing the biosynthetic code: combinations, permutations, and mutations," *Science* 282, 63-68 (1998).
3. M. Kleerebezemab, P. Hols, J. Hugenholtz, "Lactic acid bacteria as a cell factory: rerouting of carbon metabolism in Lactococcus lactis by metabolic engineering," *Enzyme Microb Technol.* 26, 840-848 (2000).
4. D. C. Cameron, N. E. Altaras, M. L. Hoffman, A. J. Shaw, "Metabolic engineering of propanediol pathways," *Biotechnol Prog.* 14, 116-25 (1998).
5. D. H. Pieper, W. Reineke, "Engineering bacteria for bioremediation," *Curr. Opin. Biotechnol.* 11 262-70 (2000).
6. J. Ohlrogge, "Plant metabolic engineering: are we ready for phase two?," *Curr. Opin. Plant Biol.* 2, 121-122.
7. S. Guillouet, A. A. Rodal, G.-H. An, P. A. Lessard, and A. J. Sinskey "Expression of the Escherichia coli catabolic threonine dehydratase, in *Corynebacterium glutamicum* and its effect on isoleucine production," *Applied and Environmental Microbiology* 6, 3100-3107 (1999).
8. M. W Losey, M. A., Schmidt, and K. F. Jensen, "A micro packed-bed reactor for chemical synthesis", In *Microreaction Technology: Industrial Prospects*(Ed, Ehrfeld, W.) Springer, Berlin, pp. 277-286 (2000).
9. R. Srinivasan, I.-M.Hsing, P. E. Berger, K. F. Jensen, S. L Firebaugh, M. A. Schmidt, M. P Harold, J. J. Lerou, and J. F Ryley. "Micromachined reactors for catalytic partial oxidation reactions". *AIChE Journal,* 43, 3059-3069 (1997).
10. T. M Floyd, M. W. Losey, S. L. Firebaugh, K. F. Jensen and M. A Schmidt. "Novel liquid phase microreactors for safe production of hazardous specialty chemicals," In *Microreaction Technology: Industrial Prospects* (Ed. Ehrfeld, W.) Springer, Berlin, pp. 171-180 (2000).
11. S. L Firebaugh, K. F. Jensen and M. A. Schmidt, "Miniaturization and integration of photoacoustic detection with a microfabricated chemical reactor system," In *Micro Total Analysis Systems* 2000 (Eds, Berg, A. v. d., Olthuis, W. and Berveld, P.) Kluwer Academic Publishers, Dordrecht, pp. 49-52 (2000).
12. M. W Losey, M. A., Schmidt, and K.F.Jensen, "Microfabricated multiphase packed-bed reactors: characterization of mass transfer and reactions," I&EC Research submitted (2000).
13. J. J Jackmann, T. Floyd, M. A. Schmidt, and K. F. Jensen, "Development of methods for on-line chemical detection with liquid-phase microchemical reactors using conventional and unconventional techniques," In *Micrototal Analysis Systems* 2000 (Eds, Berg, A. v. d., Olthuis, W. and Bergveld, P.) Kluwer Academic Publishers, Dordrecht, pp. 155-159 (2000).
14. S. W. Lee, P. E. Laibinis, "Protein resistant coatings for glass and metal oxide surfaces derived from oligo(ethylene glycol)-terminated alkyltrichlorosilanes." *Biomaterials* 19, 1669-1675 (1998).
16. N. Y. Kim, P. E. Laibinis,. "Covalent modification of hydrogen-terminated silicon surfaces," In *New Directions in Materials Synthesis,* C. H. Winter, Ed.; *ACS Symposium Series,* 727, 157-168 (1999).
17. Y. K. Namyong, N. L. Jeon, I. S. Choi, S. Takami, Y. Harada, K. R, Finnie, G. S. Girolami, R. G. Nuzzo, G. M. Whitesides, and P. E. Laibinis, "Surface-initiated ring-opening metathesis polymerization on silicon," *Macromolecules*, 33, 2793-2795 (2000).

18. J. J. Hickman, D. Ofer, C. Zou, M. S. Wrighton, P. E. Laibinis, G. M. Whitesides, "Selective functionalization of gold microstructures with ferrocenyl derivatives via reaction with thiols or disulfides: Characterization by electrochemistry and auger electron spectroscopy," *J. Am. Chem. Soc.*, 113, 1128-1132 (1991).

19. J. J. Hickman, D. Ofer, M. S. Wrighton, P. E. Laibinis, G. M. Whitesides, "Molecular self-assembly of two-terminal, voltammetric microsensors with an internal reference," *Science*, 252, 688-691 (1991).

20. R. Michalitsch; P. E. Laibinis, "Electrochemical halide detection by gold electrodes exposing a layer of silver atoms," *Angewandte Chemie* (submitted).

21. Q.-Y. Li, L. M. Davis, "Rapid and efficient detection of single chromophore molecules in aqueous solution," *Applied Optics*, 34, 3208-3217 (1995).

22. A. G. Mignani, F. Baldini, "In-vivo biomedical monitoring by fiber-optic systems," *J. of Lightwave Tech.*, 13, 1396-1406 (1995).

23. I.-Y. Li, L. M. Davis, *Applied Optics*, 34, 3208-3217 (1995)

24. C.-M. Chun, W. Lo, K.-Y. Wong, "Application of a luminescence-based pH optrode to monitoring of fermentation by Klebsiella pneumoniae," *Biosensors and Bioactuators*, 15, 7-11 (2000).

25. M. E. Lippitsch, S. Draxler, D. Kieslinger, *Sensors and Actuators B*, 38-39, 96-102 (1997).

26. S. Draxler, M. E. Lippitsch, "pH sensors using fluorescence decay time," *Sensors and Acutators B*, 29, 199-203 (1995).

27. B. J. Feilmeier, G. Iseminger, D. Schroeder, H. Webber, G. J. Phillips, "Green fluorescent protein functions as a reporter for protein localization in *escherichia coli*," *J. Bacteriol.*, 182, 4068-4076 (2000).

28. D. H. Edwards, H. B. Thomaides, J. Errington "Promiscuous targeting of *bacillus subtilis* cell division protein DivIVA to division sites in *Escherichia coli* and fission yeast," *Embo. J.*, 19, 2719-27 (2000).

29. D. Aldon, B. Brito, C. Boucher, S. Genin, "A bacterial sensor of plant cell contact controls the transcriptional induction of *Ralstonia solanacearum* pathogenicity genes," *Embo J.* 19, 2304-14 (2000).

30. K. R. Finer, J. J. Finer "Use of *Agrobacterium* expressing green fluorescent protein to evaluate colonization of sonication-assisted *Agrobacterium*-mediated transformation-treated soybean cotyledons" *Lett Appl Microbiol.* 30, 406-410 (2000).

31. M. F. Garcia-Parajo, G. M. Segers-Nolten, J. Veerman, J. Greve, N. F. van Hulst "Real-time light-driven dynamics of the fluorescence emission in single green fluorescent protein molecules," *Proc Natl Acad Sci U.S.A.*, 97, 7237-7242 (2000).

32. A. K. Dunn, J. Handelsman, "A vector for promoter trapping in *Bacillus cereus*," *Gene*, 226, 297-305 (1999).

33. J. N. Demas and B. A. DeGraff, "Design and Applications of Highly Luminescent Transition Metal Complexes", *Analytical Chemistry*, vol. 63, ppl 829-837, 1991.

34. S. B. Bamobt, et al., "Phase Fluorometric Sterilizable Optical Oxygen Sensor", *Biotechnology and Bioengineering*, vol. 43, ppl 1139-1145, 1994.

35. A. K. McEvoy, et al., "Dissolved oxygen sensor based on fluorescence quenching of oxygen-sensitive ruthenium complexes immobilized in sol-gel derived porous silicon coatings", *Analyst*, vol. 121, pp. 785-788, 1996.

36. Z. Zhujun, et al., "A Carbon Dioxide sensor Based on Fluorescence", *Analytica Chimica Acta*, 160: 305-309 (1984).

37. Y. Kawabata, et al., "Fiber-Optic Sensor for Carbon Dioxide with a pH Indicator Dispersed in a Poly (Ethylene Glycol) Membrane", *Analytica Chimica Acta*, 219:223-229 (1989).

38. B. Weigl, et al., "Chemically and mechanically resistant carbon dioxide optrode based on a covalently immobilized pH indicator", *Analytica Chimica Acta*, 282:335-343 (1993).

39. Y. Kostov, et al., "Low-cost Microbioreactor for High Throughput Bioprocessing", *Biotechnology and Bioengineering*, vol. 72, pp. 346-352, 2001.

40. S. DeWitt, "Microreactors for Chemical Synthesis", *Curr. Op. in Biotechnology*, 3:350-356, 1999.

41. F. Neidhardt, (ed.), "*Escherichia Coli* and *Salmonella*: Cellular and Molecular Biology, CD-ROM edition, September 1999, Amer Society for Microbiology; ISBN: 1555811647.

42. E. Winzeler, "Functional characterization of the *S. cerevisiae* genome by gene deletion and parallel analysis", *Science* 1999 Aug 6;285(5429):901-6.

43. J. Sambrook, et al., *Molecular Cloning—A Laboratory Manual*, $2^{nd}$ ed.: Cold Spring Harbor Laboratory Press, 1989.

44. T. C. Merkel, et al., "Gas sorption, diffusion, and permeation in poly(dimethylsiloxane)", *J. of Polymer Science, Part B—Polymer Physics*, vol. 38, ppl 415-434, 2000.

45. *Perry's Chemical Engineering Handbook:* R. R. Donnelley & Sons Company, 1984.

46. B. Atkinson and F. Mavituva, *Biochemical Engineering and Biotechnology Handbook.* New York: The Nature Press, 1983.

47. Rooney, M. T. V. and W. R. Seitz, An optically sensitive membrane for pH based on swellable polymer microspheres in a hydrogel. *Analytical Communications*, 1999. 36(7): p. 267-270.

48. Vacik, J., et al., *The Effect of Ph and Temperature on the Electrical-Conductivity of Membranes Made of Methacrylic-Acid Co-Polymers.* Collection of Czechoslovak Chemical Communications, 1983. 48(11): p. 3071-3078.

49. Vacik, J. and J. Kopecek, Specific Resistances of Hydrophilic Membranes Containing Ionogenic Groups. *Journal of Applied Polymer Science*, 1975. 19(11): p. 3029-3044.

50. Sheppard, N. F., R. C. Tucker, and S. Salehihad, Design of a Conductimetric Ph Microsensor Based on Reversibly Swelling Hydrogels. *Sensors and Actuators B-Chemical*, 1993. 10(2): p. 73-77.

51. Sheppard, N. F., M. J. Lesho, and P. McNally, Microfabricated Conductimetric Ph Sensor. *Sensors and Actuators B-Chemical*, 1995. 28(2): p. 95-102.

52. Zabriskie, D, et al. "Estimation of fermentation biomass concentration by measuring culture fluorescence", *Appl. Eur. Microbiol.* 1978, Vol. 35(2), pp. 337-343;

53. Marose, S., et al. "Two-dimensional fluorescence spectroscopy: A new tool for online bioprocess monitoring", *Biotechnology Progress*, 1998, 14, pp. 63-74).

54. Stephanopolous, G., ed. *Bioprocessing.* Second ed. *Biotechnology*, ed. H.-J. Rehm, et al. Vol. 3. 1993, VCH Publishers Inc.: New York.

55. Bailey, J. E. and D. F. Ollis, *Biochemical Engineering Fundamentals.* Second ed. McGraw-Hill chemical engineering series. 1986: McGraw-Hill, Inc.

56. Demas, J., et al., "Applications of luminescent transition platinum group metal complexes to sensor technology and molecular probes", *Coordination Chemistry Reviews*, 211, 2001, pp. 317-351.
57. Demas, J., et al. "Oxygen sensors based on luminescence quenching", *Analytical Chemistry News and Features*, Dec. 1, 1999, pp. 793A-800A.
58. Duffy, D., et al., "Rapid prototyping of microfluidic systems in poly(dimethylsiloxane)," *Analytical Chemistry*, vol. 70, pp. 4974-4984, 1998.
59. Mulder, M., *Basic Principles of Membrane Technology*. Second ed. 1996: Kluwer Academic Publishers.
60. Tamai, Y., H. Tanaka, and K. Nakanishi, *Molecular Simulation of Permeation of Small Penetrants through Membranes .1. Diffusion-Coefficients*. Macromolecules, 1994. 27(16): p. 4498-4508.
61. Tamai, Y., H. Tanaka, and K. Nakanishi, *Molecular Simulation of Permeation of Small Penetrants through Membranes .2. Solubilities*. Macromolecules, 1995. 28(7): p. 2544-2554.
62. Watson, J. M. and M. G. Baron, *The behaviour of water in poly(dimethylsiloxane)*. Journal of Membrane Science, 1996. 110(1): p. 47-57.
63. Fritz, L. and D. Hofmann, *Molecular dynamics simulations of the transport of water-ethanol mixtures through polydimethylsiloxane membranes*. Polymer, 1997. 38(5): p. 1035-1045.
64. Merkel, T. C., et al., Gas sorption, diffusion, and permeation in poly(dimethylsiloxane) *Journal of Polymer Science Part B—Polymer Physics*, 2000. 38(3): p. 415-434.
65. Stem, S. A., V. M. Shah, and B. J. Hardy, Structure-Permeability Relationships in Silicone Polymers. *Journal of Polymer Science Part B—Polymer Physics*, 1987. 25(6): p. 1263-1298.
66. Pinnau, I. and L. G. Toy, *Gas and vapor transport properties of amorphous perfluorinated copolymer membranes based on 2,2-bistrifluoromethyl-4,5-difluoro-1,3-dioxole/tetrafluoroethylene*. Journal of Membrane Science, 1996. 109(1): p. 125-133.
67. C. McDonagh, et al., "Tailoring of sol-gel films for optical sensing of oxygen in gas and aqueous phase", *Analytical Chemistry*, Vol. 70(1), Jan. 1, 1998, pp. 45-50.
68. S. Parekh, et al., "Improvement of microbial strains and fermentation processes", *Appl. Microbiol. Technol.*, 54:287-301, 2000.
69. A. L. Demain and J. E. Davis, *Manual of industrial microbiology and technology*, 2$^{nd}$ ed., Am. Soc. Microbiol. Press, Washington, D.C., 1998.
70. Swarz, J. R., "Advances in *Escherichia coli* production of therapeutic proteins", *Current Opinion in Biotechnology*, 2001. 12: p. 195-201.
71. Baneyx, F., "Recombinant protein expression in *Escherichia coli*", *Current Opinion in Biotechnology*, 1999. 10(5): p. 411-421.
72. Cereghino G P, Cregg J M., "Applications of yeast in biotechnology: protein production and genetic analysis", *Curr Opin Biotechnol.* 1999 Oct;10(5):422-7.
73. S. Hashimoto and A. Ozaki, "Whole microbial cell processes for manufacturing amino acids, vitamins or ribonucleotides", *Curr Opin Biotechnol.* 1999 Dec;10(6):604-8.
74. Tanaka, H., J. Takahashi, and K. Ueda, "Studies on Effect of Agitation on Mycelia in Submerged Mold Culture .3. Standard for Intensity of Agitation Shock on Mycelia on Agitation of Mycelial Suspensions", *Journal of Fermentation Technology*, 1975. 53(1): p. 18-26.
75. Oldshue, Y., "Fermentation mixing scale-up techniques", *Biotechnology and Bioengineering*, 1966. 8: p. 3-24.
76. Hauser, H., et al. (eds.), *Mammalian Cell Biotechnology in Protein Production*, W de Gruyter, 1997.
77. Campbell, S., *The Science and Engineering of Microelectronic Fabrication*, 2nd Ed., Oxford: 2001.
78. Madou, M., *Fundamentals of Microfabrication*, Boca Raton: CRC Press, 1997.
79. Lahann, J., "Reactive Polymer Coatings: A Platform for Patterning Proteins and Mammalian Cells onto a Broad Range of Materials", Langmuir, May 2002.
80. Ferraro, J. R., et al., *Introductory Raman Spectroscopy*, Academic Press; 2nd edition (Oct. 28, 2002).
81. Lasema, J. J. (Ed.) Modern Techniques in Raman Spectroscopy, John Wiley & Son Ltd; 1 edition (Aug. 28, 1996).
82. Pramanik, J. & Keasling, J. D. Stoichiometric model of Escherichia coli metabolism: incorporation of growth-rate dependent biomass composition and mechanistic energy requirements. *Biotechnology and Bioengineering* 56, 398-421, 1997.
83. Wolfbeis, O. S., "Fiber-Optic Chemical Sensors and Biosensors", *Anal. Chem.* 74: 2663-2678, 2002.
84. Anderlei T, Buchs J. 2001. Device for sterile online measurement of the oxygen transfer rate in shaking flasks. *Biochemical Engineering Journal* 7(2):157-162.
85. Ausubel F M, Brent R, Kingston R E, Moore D D, Seidman J G, Smith J A, Struhl K, editors. 1995. *Short Protocols in Molecular Biology*. Third ed: John Wiley & Sons, Inc.
86. Bacon J R, Demas J N. 1987. Determination of oxygen concentrations by luminescence quenching of a polymer-immobilized transition-metal complex. *Analytical Chemistry* 59(23):2780-5.
87. Bauer S, Shiloach J. 1974. Maximal exponential growth rate and yield of *E. coli* obtainable in a bench-scale fermentor. Biotechnology and Bioengineering 16(7):933-41.
88. Brunker R L, Brown O R. 1971. Effects of hyperoxia on oxidized and reduced NAD and NADP concentrations in *Escherichia coli*. Microbios 4(15): 193-203.
89. Carraway E R, Demas J N, DeGraff B A, Bacon J R. 1991. Photophysics and photochemistry of oxygen sensors based on luminescent transition-metal complexes. Analytical Chemistry 63(4):337-42.
90. Chartrain M, Salmon PM, Robinson DK, Buckland BC. 2000. Metabolic engineering and directed evolution for the production of pharmaceuticals. Current Opinion in Biotechnology 11(2):209-214.
91. Demas J N, DeGraff B A. 1991. Design and applications of highly luminescent transition metal complexes. Analytical Chemistry 63(17):829-837.
92. Demas J N, DeGraff B A, Coleman P B. 1999. Oxygen sensors based on luminescence quenching. Analytical Chemistry 71(23):793A-800A.
93. Demas JN, DeGraff BA, Xu W. 1995. Modeling of luminescence quenching-based sensors: comparison of multisite and nonlinear gas solubility models. Analytical Chemistry 67(8):1377-80.
94. Ge X, Kostov Y, Rao G. 2003. High-stability non-invasive autoclavable naked optical CO2 sensor. Biosensors & Bioelectronics 18(7):857-865.
95. Gottlieb SF. 1971. Effect of hyperbaric oxygen on microorganisms. Annual Review of Microbiology 25:111-152.
96. Gram A. 1997. Biochemical engineering and industry. Journal of Biotechnology 59(1-2):19-23.
97. Gupta A, Rao G. 2003. A study of oxygen transfer in shake flasks using a non-invasive oxygen sensor. Biotechnology and Bioengineering 84(3):351-358.

98. Hermann R, Lehmann M, Buchs J. 2003. Characterization of gas-liquid mass transfer phenomena in microtiter plates. Biotechnology and Bioengineering 81(2): 178-186.
99. John G T, Goelling D, Klimant I, Schneider H, Heinzle E. 2003a. pH-Sensing 96-well microtitre plates for the characterization of acid production by dairy starter cultures. Journal of Dairy Research 70(3):327-333.
100. John GT, Klimant I, Wittmann C, Heinzle E. 2003b. Integrated optical sensing of dissolved oxygen in microtiter plates: A novel tool for microbial cultivation. Biotechnology and Bioengineering 81(7):829-836.
101. Kim J W, Lee Y H. 1998. Development of microfermenter chip. Journal of the Korean Physical Society 33:S462-S466.
102. Klimant I, Wolfbeis O S. 1995. Oxygen-sensitive luminescent materials based on silicone-soluble ruthenium diimine complexes. Analytical Chemistry 67(18):3160-6.
103. Konz J O, King J, Cooney C L. 1998. Effects of oxygen on recombinant protein expression. Biotechnology Progress 14(3):393-409.
104. Kosch U, Klimant I, Werner T, Wolfbeis OS. 1998. Strategies to design pH optodes with luminescence decay times in the microsecond time regime. Analytical Chemistry 70(18):3892-3897.
105. Kostov Y, Harms P, Randers-Eichhorn L, Rao G. 2001. Low-cost microbioreactor for high-throughput bioprocessing. Biotechnology and Bioengineering 72(3):346-352.
106. Lakowicz J R, editor. 1999. Principles of Fluorescence Spectroscopy. 2nd edition ed: Plenum Publishing Corporation.
107. Lamping S R, Zhang H, Allen B, Shamlou P A. 2003. Design of a prototype miniature bioreactor for high throughput automated bioprocessing. Chemical Engineering Science 58(3-6):747-758.
108. Lide D R, editor. 2001. CRC Handbook of Chemistry and Physics. 82nd ed: CRC Press.
109. Liebsch G, Klimant I, Krause C, Wolfbeis OS. 2001. Fluorescent imaging of pH with optical sensors using time domain dual lifetime referencing. Analytical Chemistry 73(17):4354-4363.
110. Lin J. 2000. Recent development and applications of optical and fiber-optic pH sensors. Trac-Trends in Analytical Chemistry 19(9):541-552.
111. Maharbiz M M, Holtz W J, Howe R T, Keasling J D. 2004. Microbioreactor arrays with parametric control for high-throughput experimentation. Biotechnology and bioengineering 85(4):376-81.
112. Maharbiz M M, Holtz W J, Sharifzadeh S, Keasling J D, Howe R T. 2003. A microfabricated electrochemical oxygen generator for high-density cell culture arrays. Journal of Microelectromechanical Systems 12(5):590-599.
113. Maier U, Buchs J. 2001. Characterisation of the gas-liquid mass transfer in shaking bioreactors. Biochemical Engineering Journal 7(2):99-106.
114. Merkel T C, Bondar V I, Nagai K, Freeman B D, Pinnau I. 2000. Gas sorption, diffusion, and permeation in poly (dimethylsiloxane). Journal of Polymer Science Part B-Polymer Physics 38(3):415-434.
115. Monod J. 1949. The growth of bacterial cultures. Annual Review of Microbiology 3:371-394.
116. Onken U, Liefke E. 1989. Effect of total and partial pressure (oxygen and carbon dioxide) on aerobic microbial processes. Advances in Biochemical Engineering/Biotechnology 40(Bioprocesses Eng.): 137-69.
117. Parekh S, Vinci V A, Strobel R J. 2000. Improvement of microbial strains and fermentation processes. Applied Microbiology and Biotechnology 54(3):287-301.
118. Perry R H, Green D, editors. 1984. Perry's Chemical Engineering Handbook: R. R. Donnelley & Sons Company.
119. Randers-Eichhorn L, Bartlett R A, Frey D D, Rao G. 1996. Noninvasive oxygen measurements and mass transfer considerations in tissue culture flasks. Biotechnology and Bioengineering 51(4):466-478.
120. Schmid R D, Hammelehle R. 2003. Pocket Guide to Biotechnology and Genetic Engineering: Wiley-VCH.
121. Shanks J V, Stephanopoulos G. 2000. Biochemical engineering—bridging the gap between gene and product. Current Opinion in Biotechnology 11:169-170.
122. Stitt D T, Nagar M S, Haq T A, Timmins M R. 2002. Determination of growth rate of microorganisms in broth from oxygen-sensitive fluorescence plate reader measurements. BioTechniques 32(3):684, 686, 688-689.
123. Tolosa L, Kostov Y, Harms P, Rao G. 2002. Noninvasive measurement of dissolved oxygen in shake flasks. Biotechnology and Bioengineering 80(5):594-597.
124. Van Suijdam J C, Kossen N W F, Joha A C. 1978. Model for oxygen transfer in a shake flask. Biotechnology and Bioengineering 20(11):1695-709.
125. Verhulst P-F. 1838. Notice sur la loi que la population suit dans son accroissement. Correspondance Mathematique et Physique(10): 113-121.
126. Weuster-Botz D, Altenbach-Rehm J, Arnold M. 2001. Parallel substrate feeding and pH-control in shaking-flasks. Biochemical Engineering Journal 7(2):163-170.
127. Wittmann C, Kim H M, John G, Heinzle E. 2003. Characterization and application of an optical sensor for quantification of dissolved $O_2$ in shake-flasks. Biotechnology Letters 25(5):377-380.

The invention claimed is:

1. An apparatus for parallel operation of a plurality of microreactors comprising:
   a chamber equipped with at least one element that supports or secures a microreactor tray inside the chamber, wherein the microreactor tray holds a plurality of microreactors;
   a supporting component that holds a signal transmission device, wherein the supporting component and microreactor tray are controllably movable with respect to one another;
   a plurality of support structures that contain or support an actuating device, wherein the support structures are movable with respect to the microreactor tray and wherein movement of the supporting component brings the supporting component into contact with a support structure, thereby moving the support structure so as to allow the supporting component to position a sensing device held by the supporting component into operably close proximity to microreactors mounted in or on a microreactor tray installed in the chamber; and
   at least one spring that extends from the support structure to a wall of the chamber, and wherein movement of the support structure resulting from contact with the supporting component compresses the at least one spring.

2. The apparatus of claim 1, wherein termination of contact between the support structure and the supporting component releases compression of the at least one spring, thereby resulting in movement of the supporting structure to its previous position.

* * * * *